(12) United States Patent
Frankard

(10) Patent No.: US 7,872,172 B2
(45) Date of Patent: Jan. 18, 2011

(54) PLANTS HAVING IMPROVED YIELD AND METHOD FOR MAKING THE SAME

(75) Inventor: Valerie Frankard, Sint-Genesius-Rode (BE)

(73) Assignee: CropDesign N.V. (BE)

( * ) Notice: Subject to any disclaimer, the term of this patent is extended or adjusted under 35 U.S.C. 154(b) by 0 days.

(21) Appl. No.: 10/592,277

(22) PCT Filed: Mar. 8, 2005

(86) PCT No.: PCT/EP2005/051033

§ 371 (c)(1), (2), (4) Date: Sep. 8, 2006

(87) PCT Pub. No.: WO2005/085452

PCT Pub. Date: Sep. 15, 2005

(65) Prior Publication Data

US 2007/0118932 A1    May 24, 2007

Related U.S. Application Data

(60) Provisional application No. 60/553,418, filed on Mar. 16, 2004.

(30) Foreign Application Priority Data

Mar. 10, 2004    (EP) .................................. 04100991

(51) Int. Cl.
*C12N 15/82* (2006.01)
*A01H 5/00* (2006.01)
*A01H 5/10* (2006.01)

(52) U.S. Cl. ..................... 800/289; 435/320.1; 800/287; 800/298; 800/320; 800/320.1; 800/320.2; 800/320.3

(58) Field of Classification Search ........................ None
See application file for complete search history.

(56) References Cited

FOREIGN PATENT DOCUMENTS

| WO | WO 98/42851 | * | 10/1998 |
| WO | WO-98/42851 A1 | | 10/1998 |
| WO | WO-02/50292 A2 | | 6/2002 |

OTHER PUBLICATIONS

Sunilkumar G. et al. Developmental and tissue-specific expression of CaMV 35S promoter in cotton as revealed by GFP. Plant Mol Biol. Oct. 2002;50(3):463-74.*
Lee Y. et al. Expansins: ever-expanding numbers and functions. Curr Opin Plant Biol. Dec. 2001;4(6):527-32.*
GenBank Accession No. X83371, A. thaliana mRNA for cyclin delta-3, Mar. 25, 1998.*
Bargues, M. et al., "Cyclin D3-like protein (AT3g50070/F3A4_150)," *Uniprot Accession No.* Q9SN11, May 1, 2000.
Dewitte, W. et al., "Altered Cell Cycle Distribution, Hyperplasia, and Inhibited Differentiation in *Arabidopsis* Caused by the D-Type Cyclin CYCD3," *The Plant Cell*, Jan. 2003, vol. 15, No. 1, pages 79-92.
Kim, C., et al., "*Arabidopsis thaliana* AT3g50070/F3A4_150 mRNA, complete cds.," *EMBL Accession No.* AY063729, Dec. 9, 2001.
Lee, Y. et al., "Expansins: ever-expanding numbers and functions," *Current Opinion in Plant Biology*, 2001, vol. 4, pages 527-532.
Riou-Khamlichi, C. et al., "Cytokinin Activation of *Arabidopsis* Cell Division Through a D-Type Cyclin," *Science*, Mar. 5, 1999, vol. 283, pages 1541-1544.
Swaminathan K. et al., "An Enhancer Trap Line Associated with a D-Class Cyclin Gene in *Arabidopsis*," *Plant Physiology*, Dec. 2000, vol. 124, pages 1658-1667.
Rose, J.K.C., et al., "The XTH Family of Enzymes Involved in Xyloglucan Endotransglucosylation and Endohydrolysis: Current Perspectives and a New Unifying Nomenclature", Plant Cell Physiol., vol. 43, No. 12, (2002), pp. 1421-1435.
Rose, J.K.C., et al., "Cooperative Disassembly of the Cellulose-Xyloglucan Network of Plant Cell Walls: Parallels Between Cell Expansion and Fruit Ripening", Trends in Plant Science, vol. 4, No. 5, (1999), pp. 176-183.

* cited by examiner

*Primary Examiner*—Cynthia Collins
(74) *Attorney, Agent, or Firm*—Connolly Bove Lodge & Hutz LLP

(57) ABSTRACT

The present invention concerns a method for improving the yield of plants by introducing into a plant a nucleic acid encoding a cyclin D3 protein under the control of a promoter capable of preferentially expressing the nucleic acid in shoots. The invention also relates to transgenic plants comprising a nucleic acid encoding a cyclin D3 protein under the control of a promoter capable of preferentially expressing the nucleic acid in shoots, which plants have improved yield relative to corresponding wild type plants. The invention also concerns constructs useful in the methods of the invention.

27 Claims, 11 Drawing Sheets

| blosum60 | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 1. Antma_cycD3a | | 50.5 | 42.5 | 42.9 | 46 | 49 | 44.7 | 47.6 | 49.2 | 46.7 | 46.9 | 48.9 | 39.3 | 52.1 | 40.6 | 53.2 | 40.3 | 48.6 | 49.5 | 57.7 | 46.4 | 56.2 |
| 2. Antma_cycD3b | 68.4 | | 43 | 44.3 | 45.7 | 51.6 | 41.1 | 46.9 | 48.6 | 46.4 | 46.5 | 52.5 | 38.8 | 43.7 | 36.7 | 45.4 | 38.7 | 55.2 | 47.3 | 44.7 | 55.5 | 49.1 |
| 3. Arath_CYCD3_1 | 59.8 | 62.2 | | 46.5 | 44.2 | 47.6 | 44.1 | 50.5 | 51.3 | 52.2 | 48.5 | 47.7 | 35.1 | 42.7 | 40.2 | 41.9 | 37.9 | 46.4 | 50 | 43.7 | 44.6 | 46.3 |
| 4. Arath_CYCD3_2 | 59.1 | 65.4 | 65.7 | | 67.9 | 54.4 | 44.1 | 44.1 | 49.7 | 50.7 | 43.3 | 54.6 | 36.4 | 41.6 | 38.9 | 42.9 | 33.9 | 50 | 48.3 | 40.6 | 51.6 | 43.2 |
| 5. Arath_CYCD3_3 | 63.2 | 67 | 63 | 80.1 | | 52.9 | 41.8 | 43.6 | 48.4 | 51.5 | 43.3 | 52 | 36.3 | 44.7 | 36 | 45.7 | 36 | 46.4 | 47 | 43 | 47.6 | 43.9 |
| 6. Eupes_cycD | 67.6 | 69 | 64.4 | 72.5 | 72 | | 48.5 | 51.2 | 55.2 | 55.8 | 49.4 | 70.1 | 38.1 | 47.1 | 42.5 | 49.3 | 39.7 | 55.6 | 55.1 | 45 | 56 | 48.2 |
| 7. Heltu_cycD3;1 | 62.7 | 61.2 | 65.2 | 65.7 | 62.3 | 70.6 | | 48.6 | 51.2 | 53.1 | 46.8 | 46.6 | 33.8 | 42.2 | 67.4 | 45.8 | 41 | 44.7 | 52.3 | 41.6 | 43.7 | 45.9 |
| 8. Medsa_cycD3 | 64.8 | 64 | 67.4 | 63.5 | 63.7 | 68.1 | 66.3 | | 60.7 | 56.1 | 85.4 | 53.4 | 38.2 | 50 | 42.1 | 49.6 | 40.6 | 48.5 | 57.8 | 47.1 | 47.7 | 51.3 |
| 9. Nicta_cycD3;1 | 64.1 | 68.1 | 69.7 | 70 | 67.6 | 72.7 | 68.1 | 72.5 | | 69.6 | 57.3 | 57.7 | 38.9 | 48.1 | 43.1 | 47.1 | 40.8 | 50.3 | 79.5 | 47.4 | 50 | 51.7 |
| 10. Nicta_cycD3;3 | 64.7 | 67.4 | 71.8 | 71.2 | 69.8 | 74.7 | 71.2 | 71.8 | 84.2 | | 55.7 | 57.5 | 38.8 | 47.3 | 43.4 | 49.3 | 39.1 | 49.6 | 68.4 | 47.3 | 51.2 | 51.4 |
| 11. Pissa_cycD3 | 61.7 | 62.8 | 67.4 | 61.2 | 61.7 | 66.9 | 64.3 | 91.7 | 72.7 | 72.1 | | 53.1 | 36 | 49 | 39.7 | 48.8 | 40.9 | 46.9 | 54.8 | 47.8 | 48.2 | 51.3 |
| 12. Popal_cycD | 65 | 70.9 | 66.5 | 71.7 | 72.2 | 80.1 | 64.4 | 67.1 | 73.2 | 73.9 | 66.9 | | 39.9 | 49.7 | 38.7 | 52.5 | 38.8 | 56.1 | 55.9 | 45.5 | 56.4 | 50.4 |
| 13. Cheru_cycD3 | 60.6 | 60.1 | 56.9 | 55 | 59 | 58.9 | 55.7 | 54.4 | 58.4 | 55.4 | 55.5 | 59.6 | | 37.2 | 33.7 | 36.7 | 32 | 38.1 | 39.6 | 37.2 | 36.2 | 36.9 |
| 14. Eupes_cycD3;1 | 72.6 | 63.4 | 63.8 | 63.5 | 63.7 | 66.5 | 65.5 | 64.8 | 66.2 | 67.1 | 84.6 | 64.7 | 59.1 | | 38.5 | 56.9 | 38.3 | 46.8 | 48.6 | 49.7 | 45.1 | 56.9 |
| 15. Helan_cycD3 | 58.6 | 55.7 | 57.4 | 55.9 | 53.2 | 62.3 | 75.6 | 59.3 | 60.3 | 61.4 | 58.6 | 56.9 | 54.8 | 58.9 | | 40.5 | 36.9 | 39.4 | 45.4 | 39.4 | 39.3 | 41.6 |
| 16. Lagsi_cycD3;1 | 69.9 | 64.3 | 61.7 | 61.9 | 62.6 | 66.2 | 66.1 | 64 | 65.1 | 66.6 | 63.5 | 65.5 | 56 | 74.1 | 59.4 | | 40.6 | 49.7 | 49.2 | 48 | 48.1 | 53.6 |
| 17. Lagsi_cycD3;2 | 60 | 57.4 | 59.2 | 54.5 | 56.8 | 59.7 | 60.3 | 60.9 | 63.4 | 58.9 | 60.7 | 58.7 | 51.3 | 60.3 | 53.4 | 57.9 | | 37.5 | 41.8 | 39.9 | 38.2 | 39.9 |
| 18. Lyces_cycD3;1 | 66.6 | 72.3 | 65.2 | 70 | 67.9 | 73.3 | 65.5 | 67.1 | 67.8 | 70.4 | 65.9 | 72.8 | 55.7 | 65.5 | 56.8 | 68 | 60.3 | | 49.5 | 44.7 | 81.9 | 50.4 |
| 19. Lyces_cycD3;2 | 64.6 | 65.9 | 66 | 69.8 | 67.3 | 72.5 | 70.1 | 69.9 | 87.4 | 81 | 68.5 | 70.6 | 58.5 | 67 | 61.8 | 67 | 61.3 | 69 | | 45.3 | 50.7 | 50.3 |
| 20. Lyces_cycD3;3 | 71.1 | 63.2 | 60.9 | 58 | 60.9 | 63.4 | 58.5 | 61.7 | 62.7 | 63 | 62.5 | 61.7 | 54.2 | 68 | 56 | 65.6 | 57.6 | 64.6 | 59.9 | | 42.9 | 52.8 |
| 21. Nicta_cycD3;2 | 63.5 | 73 | 65.7 | 71.9 | 68.4 | 72.8 | 65.4 | 66.6 | 69.2 | 72.8 | 66.9 | 72.2 | 54.2 | 64.3 | 56.1 | 65.1 | 60.3 | 88.6 | 69.2 | 62.4 | | 49.7 |
| 22. Poptr_cycD | 69.1 | 67.6 | 68.6 | 64.1 | 62.5 | 66.8 | 64.4 | 69.7 | 70.7 | 70.7 | 69.3 | 68.4 | 56.4 | 75 | 58.2 | 71.3 | 63.4 | 67.6 | 67.6 | 67.6 | 67.6 | |

Upper right: IDENTITY / Lower left: SIMILARITY

FIGURE 3

SEQ ID NO 1: cyclin D3;3 cDNA atggctttagaagaggaggaagagagtcaaaacgcaccgttttgtgttcttgatggtct
tttctgtgaggaagagagtgagtttcacgaacaagtagatttgtgcgacgagagtgttg
aaaagtttcctttttaaatctgggtttgtctgatcatgatatgttgtgggatgatgat
gagttatcaactttgatttcgaaacaagaaccgtgtctttatgacgaaatcttagatga
tgagtttctggttttgtgtcgtgaaaaggctcttgattggatttttaaagtgaaatctc
attatgggtttaattcattgacggctcttttagctgttaattacttcgataggtttatt
acaagcaggaagtttcagacagataagccatggatgtctcagcttactgctttggcttg
tctgtctttagctgctaaggttgaagagatccgtgttccttttctcttagattttcaag
tggaagaagcaagatatgtctttgaagctaagactatacagagaatggagcttcttgtt
ctgtctactcttgactggaggatgcatcctgtgactccaatctcgttttcgatcacat
tattcgacgatacagctttaaatctcatcatcaattggagttcttgagtagatgtgaat
ctttattactctccattattcctgattcgagatttctgagttttagtccttctgtgtta
gccactgcaataatggtctctgttattagagatttgaagatgtgtgacgaagctgtata
ccaatctcagctcatgactctactcaaagttgattcggagaaggtaaataaatgctatg
agttagtgttagaccacagtccaagcaagaaaaggatgatgaattggatgcaacaaccc
gctagtccgatcggtgtgtttgatgcgtcattcagttctgatagctcgaatgagtcgtg
ggttgtgtctgcttctgcttcagtgtcgtcttcaccatcttcagagcctttgctcaaga
ggagaagagtgcaagagcagcagatgaggctatcttcaataaaccgaatgttttcgat
gtgcttagtagtagtcctcgctaa

SEQ ID NO 2: cyclin D3;3 protein

MALEEEEESQNAPFCVLDGLFCEEESEFHEQVDLCDESVEKFPFLNLGLSDHDMLWDDD
ELSTLISKQEPCLYDEILDDEFLVLCREKALDWIFKVKSHYGFNSLTALLAVNYFDRFI
TSRKFQTDKPWMSQLTALACLSLAAKVEEIRVPFLLDFQVEEARYVFEAKTIQRMELLV
LSTLDWRMHPVTPISFFDHIIRRYSFKSHHQLEFLSRCESLLLSIIPDSRFLSFSPSVL
ATAIMVSVIRDLKMCDEAVYQSQLMTLLKVDSEKVNKCYELVLDHSPSKKRMMNWMQQP
ASPIGVFDASFSSDSSNESWVVSASASVSSSPSSEPLLKRRRVQEQQMRLSSINRMFFD
VLSSSPR

FIGURE 6

**SEQ ID NO 3: beta-expansin promoter of *Oryza sativa*** aaaaccaccgagggacctgatctgcaccggttttgatagttgagggacccgttgtgtct
ggttttccgatcgagggacgaaaatcggattcggtgtaaagttaagggacctcagatga
acttattccggagcatgattgggaagggaggacataaggcccatgtcgcatgtgtttgg
acggtccagatctccagatcactcagcaggatcggccgcgttcgcgtagcacccgcggt
ttgattcggcttcccgcaaggcggcggccggtggccgtgccgccgtagcttccgccgga
agcgagcacgccgccgccgccgacccggctctgcgtttgcaccgccttgcacgcgatac
atcgggatagatagctactactctccgtttcacaatgtaaatcattctactattttc
cacattcatattgatgttaatgaatatagacatatatatctatttagattcattaacat
caatatgaatgtaggaaatgctagaatgacttacattgtgaattgtgaaatggacgaag
tacctacgatggatggatgcaggatcatgaaagaattaatgcaagatcgtatctgccgc
atgcaaaatcttactaattgcgctgcatatatgcatgacagcctgcatgcgggcgtgta
agcgtgttcatccattaggaagtaaccttgtcattacttataccagtactacatactat
atagtattgatttcatgagcaaatctacaaaactggaaagcaataaggaatacgggact
ggaaaagactcaacattaatcaccaaatatttcgccttctccagcagaatatatatctc
tccatcttgatcactgtacacactgacagtgtacgcataaacgcagcagccagcttaac
tgtcgtctcaccgtcgcacactggccttccatctcaggctagctttctcagccacccat
cgtacatgtcaactcggcgcgcgcacaggcacaaattacgtacaaaacgcatgaccaaa
tcaaaaccaccggagaagaatcgctcccgcgcgcggcggcggcgcacgtacgaatgc
acgcacgcacgcccaaccccacgacacgatcgcgcgcgacgccggcgacaccggccatc
cacccgcgccctcacctcgccgactataaatacgtaggcatctgcttgatcttgtcatc
catctcaccaccaaaaaaaaggaaaaaaaaacaaaacacaccaagccaaataaaagcg
acaa

SEQ ID NO 4: primer prm0360 ggggacaagtttgtacaaaaaagcaggcttcacaatggctttagaagaggagga

SEQ ID NO 5: primer prm0361 ggggaccactttgtacaagaaagctgggtttagcgaggactactataagca

PLANTS HAVING IMPROVED YIELD AND METHOD FOR MAKING THE SAME

RELATED APPLICATIONS

This application is a national stage application (under 35 U.S.C. 371) of PCT/EP2005/051033 filed Mar. 8, 2005, which claims benefit to European application 04100991.1 filed Mar. 10, 2004 and U.S. provisional application 60/553,418 filed Mar. 16, 2004.

SEQUENCE LISTING SUBMISSION

The Sequence Listing associated with this application is filed in electronic format via EFS-Web and hereby incorporated by reference into the specification in its entirety. The name of the text file containing the Sequence Listing is Revised_Sequence_List__14546__00002_US. The size of the text file is 139 KB, and the text file was created on Jan. 19, 2009.

FIELD OF THE INVENTION

The present invention relates generally to the field of molecular biology and concerns a method for improving plant yield relative to that of corresponding wild type plants. More specifically, the present invention concerns a method for improving yield, by introducing into a plant a nucleic acid encoding a cyclin D3, which nucleic acid is under the control of a promoter preferentially expressed in shoots. The present invention also concerns plants comprising an isolated cyclin D3 nucleic acid under the control of a promoter preferentially expressed in shoots, which plants have improved yield relative to corresponding wild type plants. The invention also concerns constructs for use in the methods according to the invention.

BACKGROUND OF THE INVENTION

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance are also important factors in determining yield. Crop yield may be increased by optimizing one of the abovementioned factors, which may be done by modifying the inherent growth mechanisms of a plant.

The inherent growth mechanisms of a plant reside in a highly ordered sequence of events collectively known as the 'cell cycle'. Progression through the cell cycle is fundamental to the growth and development of all multicellular organisms and is crucial to cell proliferation. The major components of the cell cycle are highly conserved in yeast, mammals, and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase can be stimulated to renter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The expression of genes necessary for DNA synthesis at the G1/S boundary is regulated by the E2F family of transcription factors in mammals and plant cells (La Thangue, 1994; Muller et al., 2001; De Veylder et al., 2002). Entry into the cell cycle is regulated/triggered by an E2F/Rb complex that integrates signals and allows activation of transcription of cell cycle genes. The transition between the different phases of the cell cycle, and therefore progression through the cell cycle, is driven by the formation and activation of different heterodimeric serine/threonine protein kinases, generally referred to as cyclin-dependent kinases (CDK). A prerequisite for activity of these kinases is the physical association with a specific cyclin, the timing of activation being largely dependent upon cyclin expression. Cyclin binding induces conformational changes in the N-terminal lobe of the associating CDK and contributes to the localisation and substrate specificity of the complex. Monomeric CDKs are activated when they are associated with cyclins and thus have a kinase activity. Cyclin protein levels fluctuate in the cell cycle and therefore represent a major factor in determining timing of CDK activation. The periodic activation of these complexes containing cyclins and CDK during cell cycle mediates the temporal regulation of cell-cycle transitions (checkpoints).

Cyclins can be grouped into mitotic cyclins (designated A- and B-type cyclins in higher eukaryotes and CLBs in budding yeast) and G1-specific cyclins (designated D-type cyclins in mammals and CLNs in budding yeast). H-type cyclins regulate the activity of the CAKs (CDK-activating kinases). All four types of cyclins known in plants were identified mostly by analogy to their human counterparts. In *Arabidopsis*, ten A-type, nine B-type, ten D-type and one H-type cyclin have been described (Vandepoele et al., 2002).

The 10 D-type cyclins are subdivided into seven subclasses, D1 to D7, which reflect their lack of high sequence similarity to each other, which is in contrast to the A-type and B-type cyclins.

Only the D3 and D4 subclasses have different members, respectively three and two. Redundancy of the D3-type cyclins has been proposed previously as an explanation for the failure to observe mutant phenotypes upon knocking out of a single D3-type cyclin (Swaminathan et al., 2000). The two D3-type cyclins are linked via a recent segmental duplication, which suggests that these are functionally redundant. A similar hypothesis could hold for D4-type cyclins, because two out of three are located in a duplicated block.

The much larger divergence seen for D-type cyclins compared with A- and B-type cyclins might reflect the presumed role of D-type cyclins in integrating developmental signals and environmental cues into the cell cycle. For example, D3-type cyclins have been shown to respond to plant hormones, such as cytokinins and brassinosteroids, whereas CYCD2 and CYCD4 are activated earlier in G1 and react to sugar availability (for review, see Stals and Inzé, 2001).

Overexpression of the CYCD2; 1 gene in tobacco was reported to increase cell division and increase overall plant growth rate with no morphological alterations (Cockcroft et al., 2000).

Overexpression in *Arabidopsis* of the CYCD3; 1 gene under the control of a CaMV 35S promoter was reported to give plants with enlarged cotyledons, a dramatically reduced final plant size and distorted development. At a cellular level, cells are pushed from G1, causing ectopic cell divisions in both meristematic regions and in regions in which cell division normally is absent or limited. This increase of cell numbers is coupled to a decrease in cell size (Dewitte et al., 2003).

The ability to more accurately influence the cell cycle of a plant, and to thereby more accurately modify various growth characteristics of a plant, would have many applications in areas such as crop enhancement, plant breeding, in the production of ornamental plants, aboriculture, horticulture, forestry, the production of algae for use in bioreactors (for the biotechnological production of substances such as pharmaceuticals, antibodies, or vaccines, or for the bioconversion of organic waste) and other such areas.

It is an object of the present invention to overcome some of the problems associated with the prior art expression of cyclin D3 in plants.

SUMMARY OF THE INVENTION

It has now been found that introducing into a plant a nucleic acid encoding a cyclin D3 under the control of a promoter capable of preferentially expressing the nucleic acid in shoots gives plants having improved yield. Therefore according to the present invention there is provided a method for improving yield in a plant, comprising introducing into a plant a nucleic acid encoding a cyclin D3 under the control of a promoter capable of preferentially expressing the nucleic acid in shoots.

BRIEF DESCRIPTION OF THE FIGURES

FIG. 2 is an alignment of known cyclin D3 protein sequences. The following amino acid sequences are depicted: Antma_cycD3a (SEQ ID NO: 6), Antma_cycD3b (SEQ ID NO: 7), Arath_CYCD3$_{-1}$ (SEQ ID NO: 8), Arath_CYCD3$_{-2}$ (SEQ ID NO: 9), Arath_CYCD3$_{-3}$ (SEQ ID NO: 10), Eupes_cycD3 like (SEQ ID NO: 11), Heltu_cycD3; 1 (SEQ ID NO: 12), Medsa_cycD3 (SEQ ID NO: 13), Nicta_cycD3; 1 (SEQ ID NO: 14), Nicta_cycD3; 3 (SEQ ID NO: 15), Pissa_CycD3 (SEQ ID NO: 16), Popal_cycD3 (SEQ ID NO: 17), Cheru_cycD3 (SEQ ID NO: 18), Eupes_cycD3; 1 (SEQ ID NO: 19), Helan_cycD3 (SEQ ID NO: 20), Lagsi_cycD3; 1 (SEQ ID NO: 21), Lagsi_cycD3; 2 (SEQ ID NO: 22), Lyces_cycD3; 1 (SEQ ID NO: 23), Lyces_cycD3; 2 (SEQ ID NO: 24), Lyces_cycD3; 3 (SEQ ID NO: 25), Nicta_cycD3; 2 (SEQ ID NO: 26), Orysa_cycD3 (SEQ ID NO: 27), Poptr_cycD3 (SEQ ID NO: 28), Arath_CYCD1__1 (SEQ ID NO: 29), Arath_CYCD2$_{-1}$ (SEQ ID NO: 30), Arath_CYCD4__1 (SEQ ID NO: 31), Arath_CYCD4$_{-2}$ (SEQ ID NO: 32), Arath_CYCD5$_{-1}$ (SEQ ID NO: 33), Arath_CYCD6__1 (SEQ ID NO: 34), Arath_CYCD7$_{-1}$ (SEQ ID NO: 35), Heltu_cycD1; 1 (SEQ ID NO: 36), Nicta_cycD2; 1 (SEQ ID NO: 37), Orysa_cycD5 like 3 (SEQ ID NO: 38), Triae_cycD2 (SEQ ID NO: 39), Zcama_cycD2 (SEQ ID NO: 40), Medsa_cycD1 (SEQ ID NO: 41), Orysa_cycD2/4 like 4 (SEQ ID NO: 42), Orysa_cycD2/4 like 1 (SEQ ID NO: 43), Orysa_cycD2/4 like 2 (SEQ ID NO: 44), Orysa_cycD2/4 like 3 (SEQ ID NO: 45), Orysa_cycD1 (SEQ ID NO: 46), Orysa_cycD5 like 1 (SEQ ID NO: 47), Orysa_cycD5 like 2 (SEQ ID NO: 48), Orysa_cycD6 (SEQ ID NO: 49), Sacof_cycD2/4 like (SEQ ID NO: 50).

FIG. 3 is a similarity/identity matrix prepared using MatGAT (Matrix Global Alignment Tool) which calculates the similarity and identity between every pair of sequences in a given data set without requiring pre-alignment of the data. The sequence of SEQ ID NO: 2 is indicated as number 5 in the matrix. Sequences having at least 30% sequence identity to the sequence of SEQ ID NO: 2 encompass cyclin D3s.

FIG. 6 details examples of sequences useful in performing the methods according to the present invention.

DETAILED DESCRIPTION OF THE INVENTION

Figure 1:
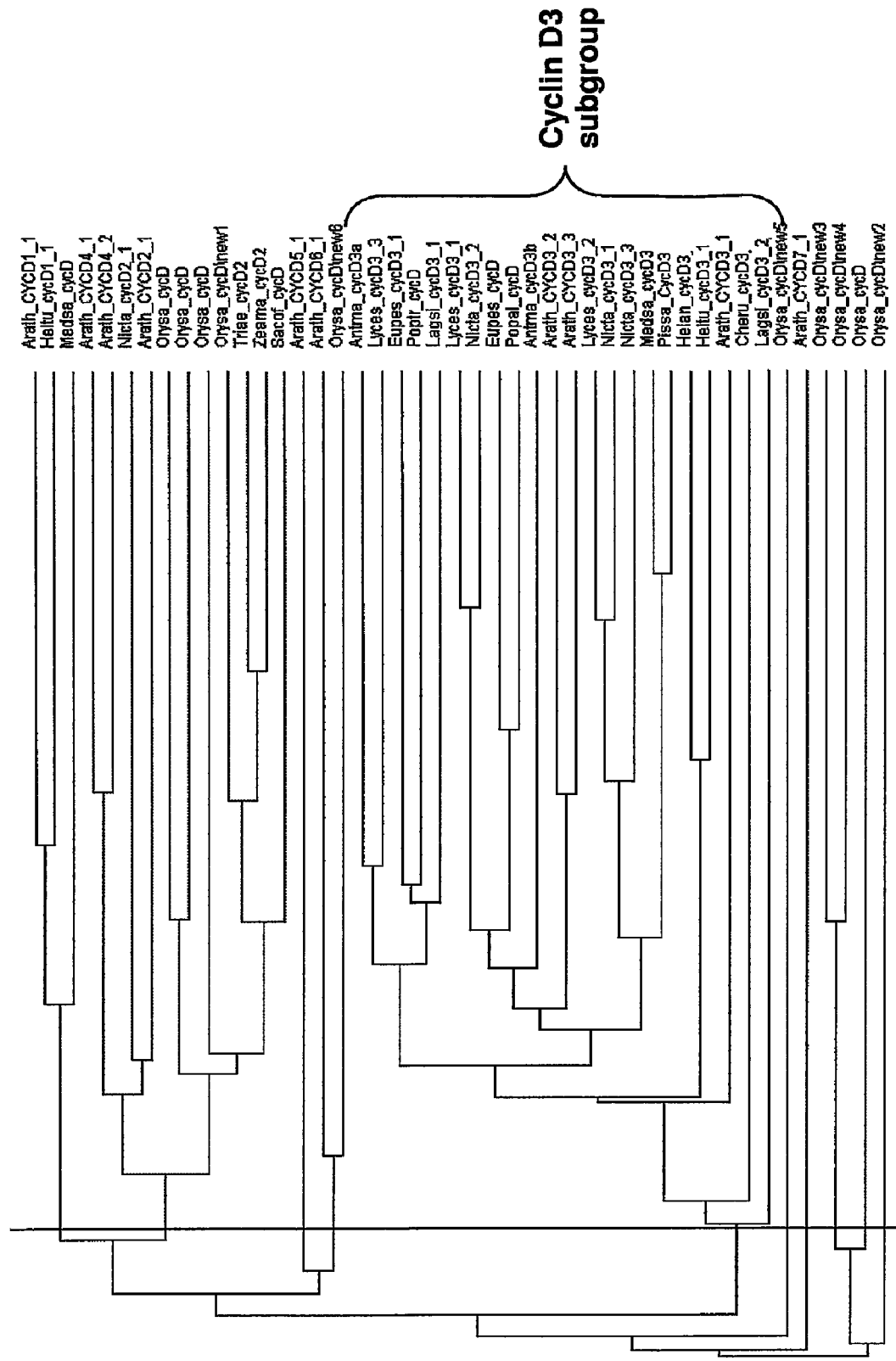
FIG. 1 is a multiple alignment showing the cyclin D3 cluster prepared using ClustalW and default values, followed by average distance tree computation.

The term "increased yield" as defined herein is taken to mean an increase in any one or more of the following, each relative to corresponding wild type plants: (i) increased biomass (weight) of one or more aboveground (harvestable) parts of a plant; (ii) increased seed yield, which may result from an increase in the biomass of the seed (seed weight) and which may be an increase in the seed weight per plant or on an individual seed basis, and which increase in seed weight may be due to altered seed dimensions, such as seed length and/or seed width and/or seed area; (iii) increased number of (filled) seeds; (iv) increased seed size, which may also influence the composition of seeds; (v) increased seed volume, which may also influence the composition of seeds; (vi) increased harvest index, which is expressed as a ratio of the yield of harvestable parts, such as seeds, over the total biomass; and (vii) increased thousand kernel weight (TKW), which is extrapolated from the number of filled seeds counted and their total weight. An increased TKW may result from an increased seed size and/or seed density.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur as a result of modified architecture.

According to a preferred feature of the present invention, performance of the methods of the invention result in plants having improved yield which is manifested by at least one of: increased aboveground area, increased total seed number, increased number of (filled) seeds, increased seed weight and increased harvest index, each relative to corresponding wild type plants. Therefore, according to the present invention, there is provided a method for increasing plant yield, particularly seed yield, which method comprises introducing into a plant a nucleic acid encoding a cyclin D3 under the control of a promoter capable of preferentially expressing the nucleic acid in shoots.

Performance of the methods of the invention give improved yield in plants whether the plant (having introduced therein a cyclin D3 gene under the control of a promoter capable of preferentially expressing the nucleic acid in shoots) is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

Further advantageously, the methods of the may be performed on any plant.

The term "plant" as used herein encompasses whole plants, ancestors and progeny of the plants and plant parts, including seeds, shoots, stems, leaves, roots (including tubers), plant cells, tissues and organs, wherein each of the aforementioned preferably comprise the gene of interest. The term "plant" also encompasses suspension cultures, embryos, meristematic regions, callus tissue, gametophytes, sporophytes, pollen, and microspores, again wherein each of the aforementioned preferably comprise the gene of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaea* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissolute, Indigo incamata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Omithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* Spp., *Rhaphiolepsis umbellate, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugarcane. More preferably the plant is a cereal, such as rice, maize, wheat, barley, millet, rye, oats or sorghum.

A cyclin D3 may be identified using different methods. For example, the query protein sequence may be blasted (for example, using blast default parameters for the gap opening penalty and the gap extension penalty) against a translated *Arabidopsis* nucleic acid sequence database. In the case where the query sequence is a cyclin D3, the first hit from the blast result will be an *Arabidopsis* cyclin D3. Another method for identifying a cyclin D3 is by aligning the query sequence with known cyclin D3 protein sequences, using for example the AlignX program from Vector NTI suite (InforMax, Bethesda, Md.). Multiple alignments may then be carried out with a gap opening penalty of 10 and a gap extension of 0.01. Minor manual editing of the alignment may also be necessary in order to better position some conserved regions. If the query sequence is a cyclin D3, it will align with the known cyclin D3 sequences.

A "cyclin D3" as defined herein refers to any amino acid sequence which, when used in the construction of a cyclin or cyclin D phylogenetic tree, such as the one depicted in FIG. 1, falls into a group which includes cyclin D3s (and not other D-type cyclins, such as cyclin D1, D2, D4, D5, D6 and D7). Reference herein to a nucleic acid encoding a cyclin D3 is to a nucleic acid encoding a cyclin D3 amino acid as defined above.

A person skilled in the art could readily determine whether any amino acid sequence in question falls within the aforementioned definition using known techniques and software for the making of such a phylogenetic tree, such as a GCG, EBI or CLUSTAL package, using default parameters. Upon construction of such a phylogenetic tree, sequences clustering in the cyclin D3 group will be considered to fall within the definition of a "cyclin D3". Nucleic acids encoding such sequences will be useful in performing the methods of the invention.

Figure 2:
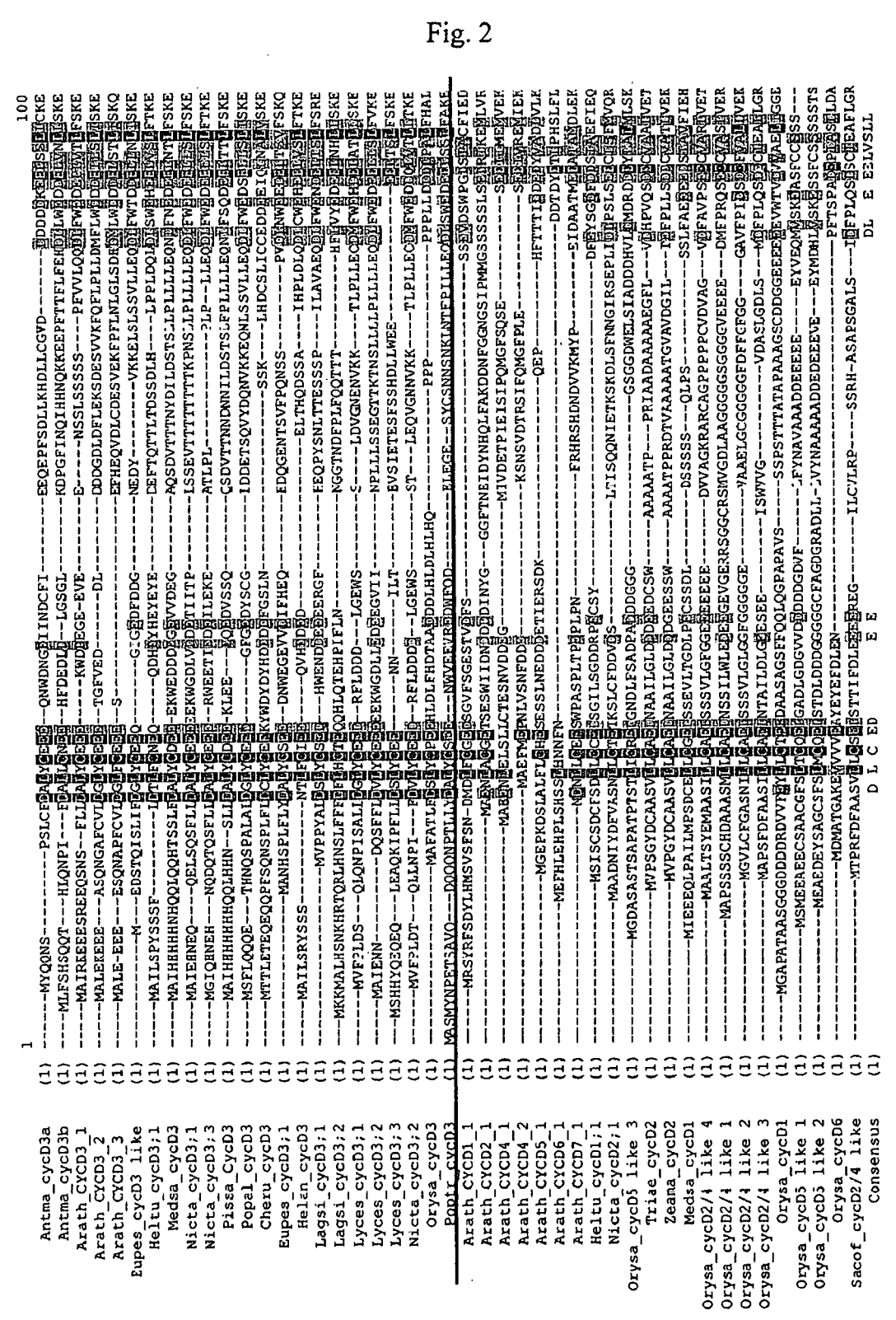
Figure 2:
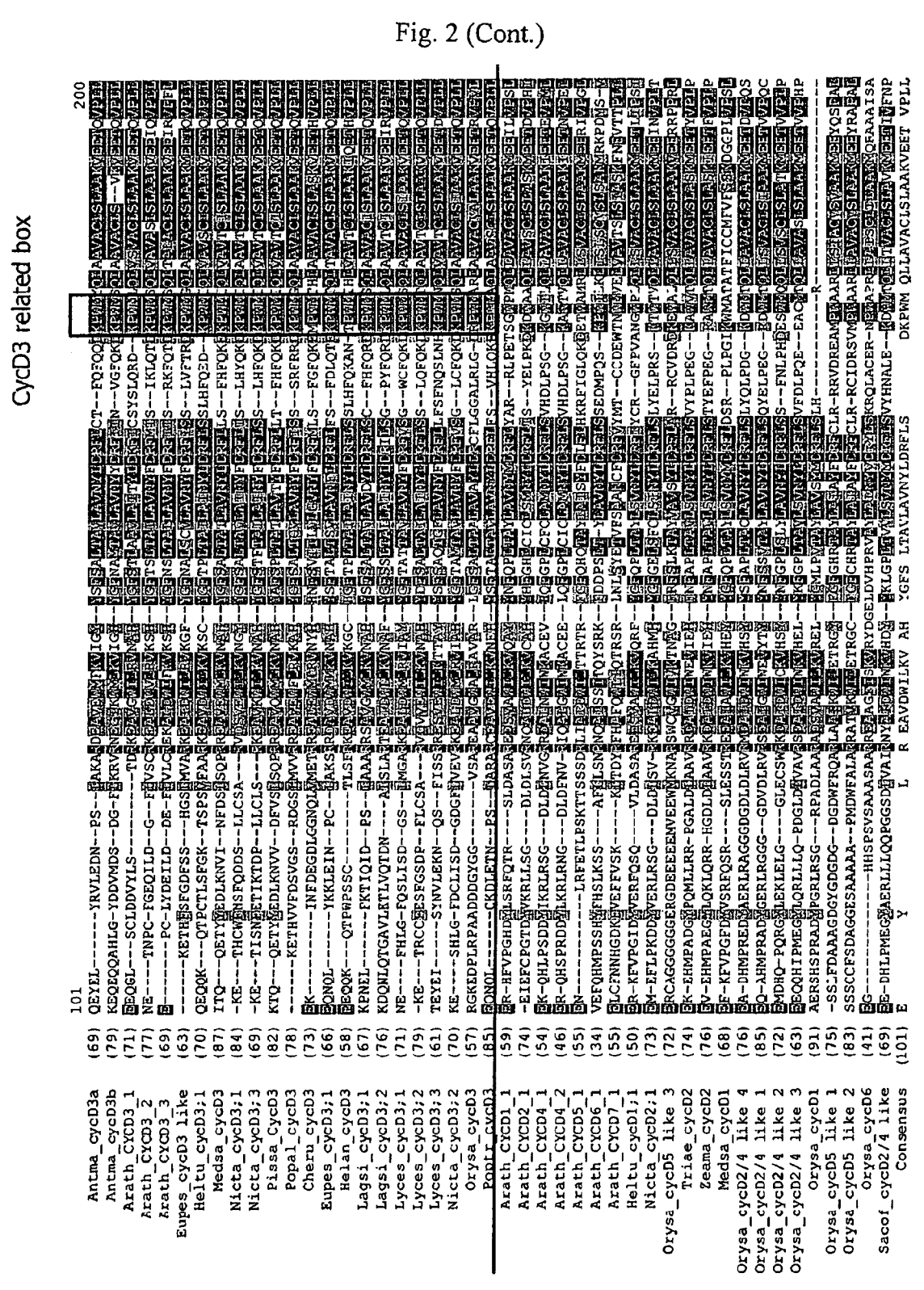
Figure 2:
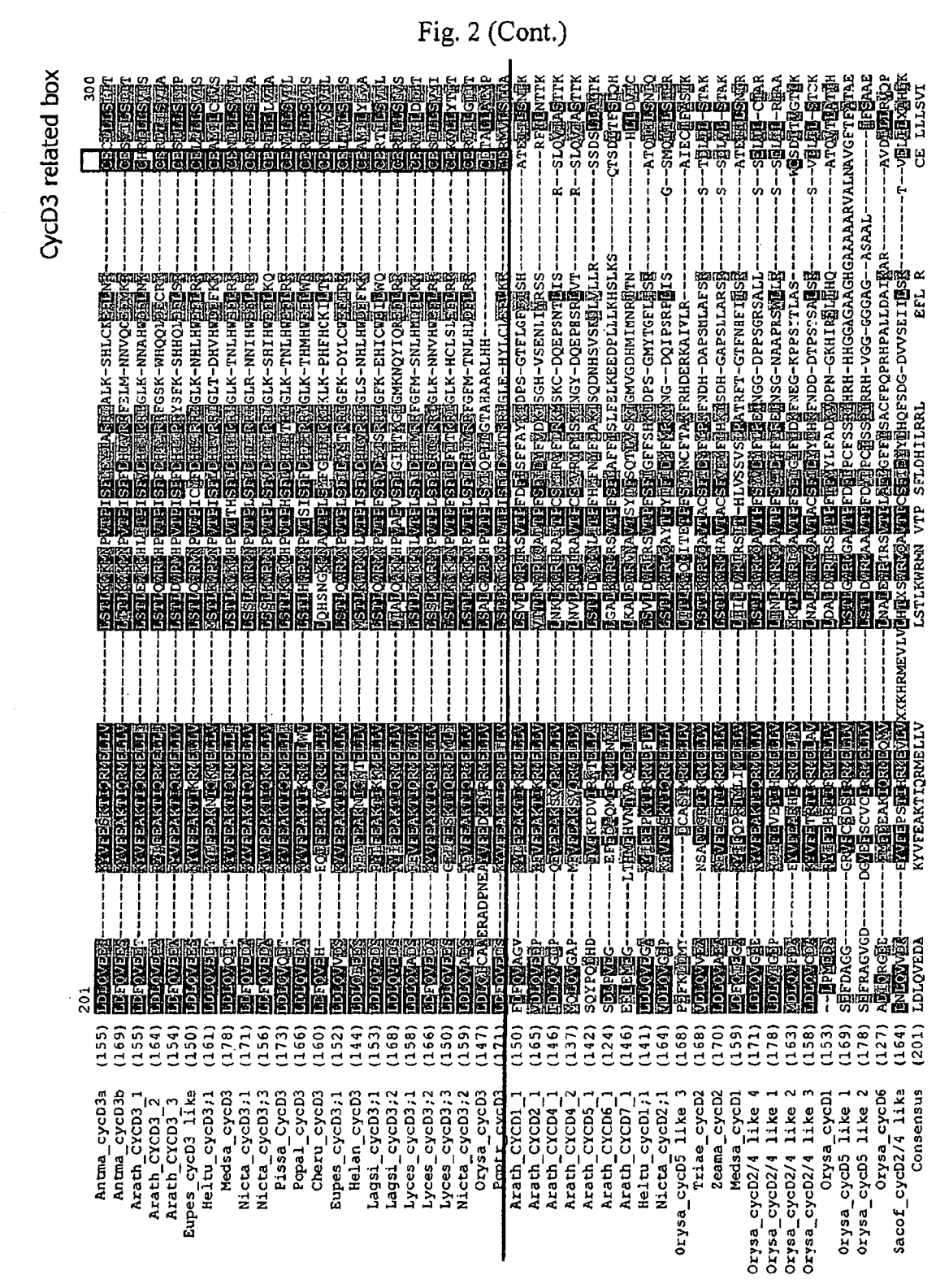
Figure 2:
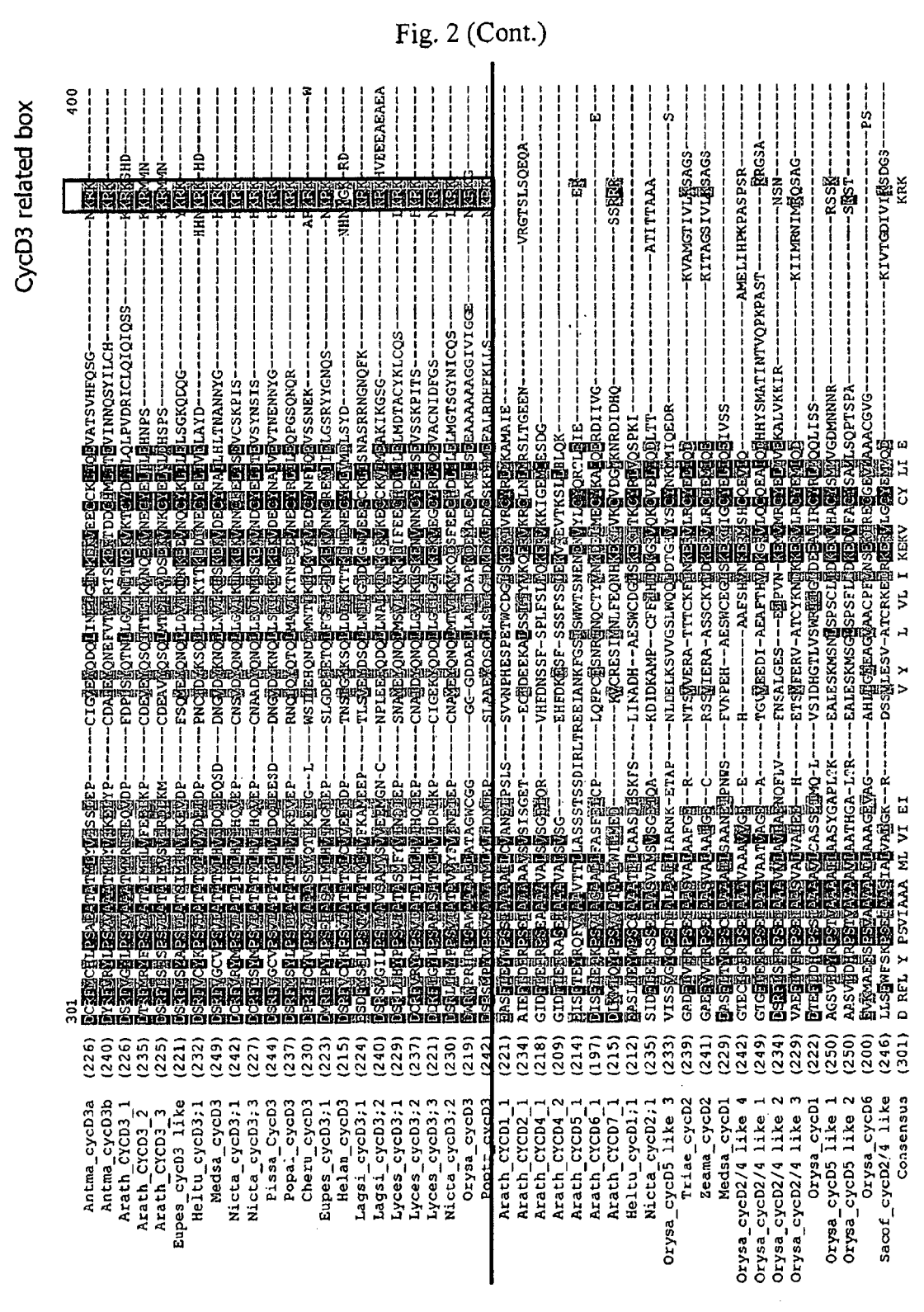
Figure 2:
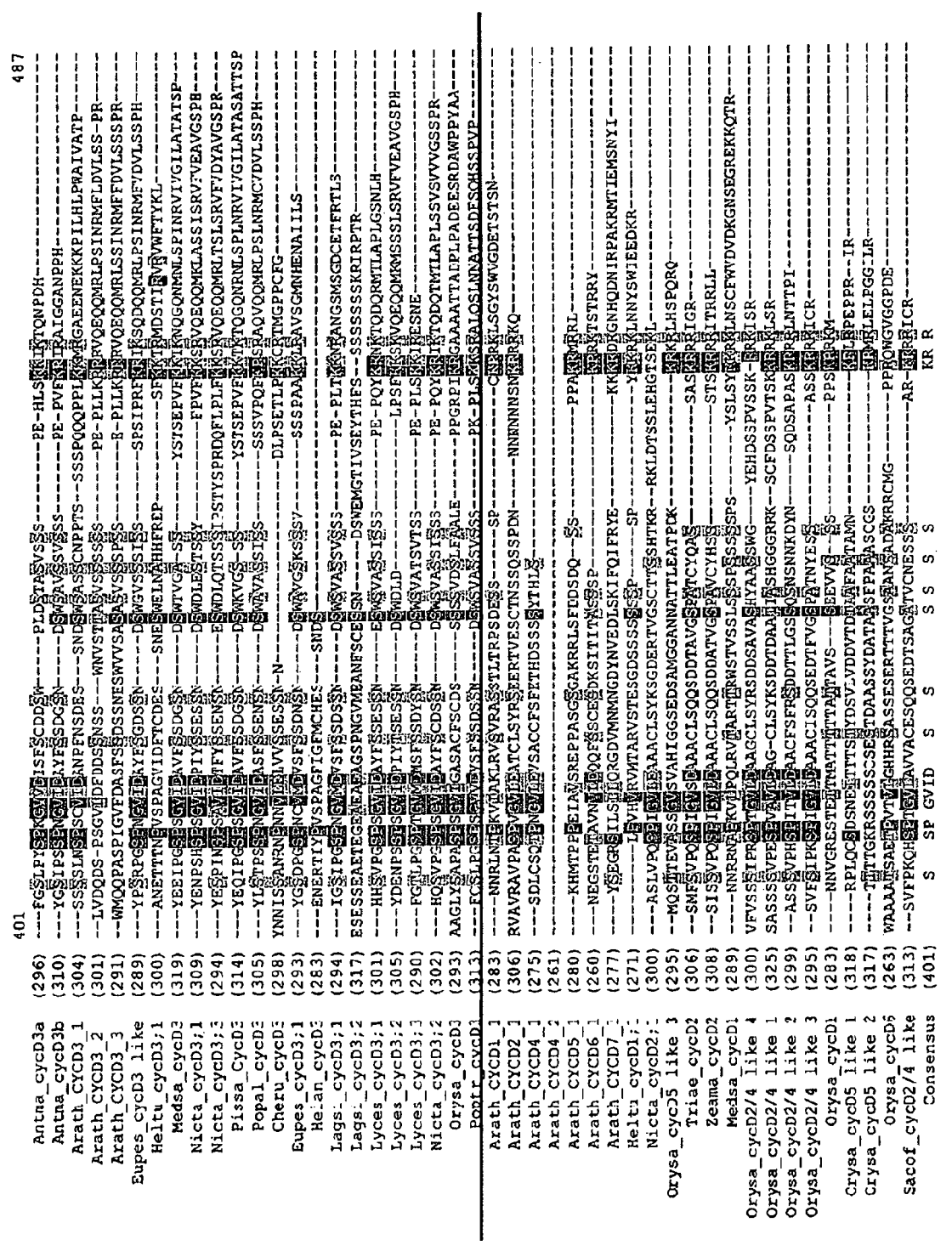

Cyclin D3s typically have the ability to bind and activate plant CDKs and Rb. In addition, cyclin D3s may comprise one or more and preferably all of the following: (i) a cyclin box; (ii) an LxCxE motif (SEQ ID NO: 51) within the first 40 or so amino acids (which is characteristic of most cyclin Ds); and (iii) one or more and preferably all of the conserved regions identified by the boxes shown in FIG. 2 (as shown in FIG. 2, one mismatch within the boxes is allowed).

Examples of nucleic acids encoding cyclin D3s falling under the aforementioned definition of a cyclin D3 are given in Table 1 below. The cyclin D3-encoding nucleic acids shown in the table may be useful in performing the methods of the invention, i.e. to obtain plants having improved yield relative to corresponding wild type plants by introducing and expressing any one of these nucleic acids under the control of a promoter capable of preferentially expressing the nucleic acids in shoots. The nucleic acid encoding a cyclin D3 is preferably the nucleic acid represented by SEQ ID NO: 1 or is a functional variant of SEQ ID NO: 1, as described hereinafter.

TABLE 1

Examples of cyclin D3-encoding nucleic acids

| Name | NCBI nucleic acid accession number | Source |
| --- | --- | --- |
| Antma_cycD3a | AJ250397 | *Antirrhinum majus* |
| Antma_cycD3b | AJ250398 | *Antirrhinum majus* |
| Arath_CYCD3_1 | NM_119579.2 | *Arabidopsis thaliana* |
| Arath_CYCD3_2 | NM_126126.2 | *Arabidopsis thaliana* |
| Arath_CYCD3_3 | NM_114867.2 | *Arabidopsis thaliana* |
| Eupes_cycD3 like | AY340588 | *Euphorbia esula* |
| Eupes_cycD3; 1 | AY340589 | *Euphorbia esula* |
| Helan_cycD3 | AY033440 | *Helianthus annuus* |
| Heltu_cycD3; 1 | AY063461 | *Helianthus tuberosus* |
| Lagsi_cycD3; 1 | AF519810 | *Lagenaria siceraria* |
| Lagsi_cycD3; 2 | AF519811 | *Lagenaria siceraria* |
| Lyces_cycD3; 1 | AJ002588 | *Lycopersicum esculentum* |
| Lyces_cycD3; 2 | AJ002589 | *Lycopersicum esculentum* |
| Lyces_cycD3; 3 | AJ002590 | *Lycopersicum esculentum* |
| Medsa_cycD3 | X88864 | *Medicago sativa* |
| Nicta_cycD3; 1 | AJ011893 | *Nicotiana tabacum* |
| Nicta_cycD3; 2 | AJ011894 | *Nicotiana tabacum* |
| Nicta_cycD3; 3 | AB015222 | *Nicotiana tabacum* |
| Orysa_cycD3-like | AK103499.1 | *Oryza sativa* |
| Pissa_CycD3 | AB008188 | *Pisum sativum* |
| Popal_cycD3 | AY230139 | *Populus alba* |
| Poptr_cycD3 | AF181993 | *Populus tremula x Populus tremuloides* |

According to the invention, enhanced or increased expression of the cyclin D3 nucleic acid in shoots is envisaged. Methods for obtaining enhanced or increased expression of genes or gene products is well documented in the art and include, for example, overexpression driven by promoters, the use of transcription enhancers or translation enhancers.

The nucleic acid encoding a cyclin D3 is operably linked to a promoter capable of preferentially expressing the nucleic acid in shoots. An example of such a promoter is a promoter having a comparable expression profile to the beta expansin promoter. It should be clear that the applicability of the present invention is not restricted to the cyclin D3 represented by SEQ ID NO: 1, nor is the applicability of the invention restricted to the use of the beta-expansin promoter in the methods of the invention.

The nucleic acid encoding a cyclin D3 may be derived from any source. The nucleic acid/gene encoding a cyclin D3 may be isolated from a microbial source, such as yeast or fungi, or from a plant, algae or animal (including human) source. This nucleic acid may be modified from its native form in composition and/or genomic environment through deliberate human manipulation. The nucleic acid is preferably a homologous nucleic acid, i.e. a nucleic acid obtained from a plant, whether from the same plant species in which it is to be introduced or whether from a different plant species. The nucleic acid may be isolated from a dicotyledonous species, preferably from the family Brassicaceae, further preferably from *Arabidopsis thaliana*. More preferably, the cyclin D3 isolated from *Arabidopsis thaliana* is a D3-type cyclin, such as a cyclin D3; 1, cyclin D3; 2 or a cyclin D3; 3. Most preferably, the cyclin D3 is cyclin D3; 3 from *Arabidopsis thaliana*, particularly the nucleic acid sequence as represented by SEQ ID NO: 1 and the amino acid sequence as represented by SEQ ID NO: 2.

The sequence represented by SEQ ID NO: 1 depicts a cyclin D3; 3 from *Arabidopsis thaliana*, with SEQ ID NO: 2 being the corresponding amino acid sequence. Advantageously, the applicability of the present invention is not restricted to the use of a cyclin D3; 3 from *Arabidopsis* as represented by SEQ ID NO: 1. The methods according to the present invention may also be practised using functional variants of a cyclin D3-encoding nucleic acid or using functional variants of the encoded polypeptide. Especially useful in the methods of the invention are functional variants of the nucleic acid represented by SEQ ID NO: 1 or functional variants of the amino acid represented by SEQ ID NO: 2.

The term "functional variant" as defined herein is a cyclin D3 which retains the ability to bind and activate a plant CDK (see for example Healy et al. (2001, J. Biol. Chem. 276(10): 7041-7047)). Functional variants will in most cases also complement yeast mutants deficient of CLNs (the term for D-type cyclins in yeast), see for example, Swaminathan et al. (2000, Plant Phys 124: 1658-1667), particularly page 1663. The functional variant is a cyclin D3 in the sense that it is an amino acid sequence which, when used in the construction of a cyclin or cyclin D phylogenetic tree, such as the one depicted in FIG. 1, falls into a group which includes cyclin D3s (and not other D-type cyclins, such as cyclin D1, D2, D4, D5, D6 and D7). Reference herein to a nucleic acid encoding a cyclin D3 is to a nucleic acid encoding a cyclin D3 amino acid as defined above. In addition, the functional variant may comprise one or more and preferably all of the following: (i) a cyclin box; (ii) an LxCxE motif (SEQ ID NO: 51) within the first 40 or so amino acids (which is characteristic of most cyclin Ds); and (iii) one or more and preferably all of the conserved regions identified by the boxes shown in FIG. 2 (as shown in FIG. 2, one mismatch within the boxes is allowed). Furthermore, a person skilled in the art may also readily determine whether a particular cyclin D3 is a functional variant (in the sense of whether it is able to improve plant yield) by simply substituting the sequence described in the Examples section below with the variant to be tested for function.

Suitable functional variant nucleic acid and amino acid sequences useful in practising the methods according to the invention, include:
(i) Portions of a cyclin D3-encoding nucleic acid, preferably a portion of a cyclin D3-encoding nucleic acid as represented by the sequence of SEQ ID NO: 1;
(ii) Alternative splice variants of a cyclin D3-encoding nucleic acid, preferably an alternative splice variant of a cyclin D3-encoding nucleic acid as represented by the sequence of SEQ ID NO: 1;
(iii) Allelic variants of a cyclin D3-encoding nucleic acid, preferably an allelic variant of a cyclin D3-encoding nucleic acid as represented by the sequence of SEQ ID NO: 1; and
Homologues, derivatives and active fragments of a cyclin D3 amino acid sequence, preferably a cyclin D3 as represented by the sequence of SEQ ID NO: 2.

It will be apparent to a person skilled in the art that the use of a full length cyclin D3-encoding DNA sequence would not be a prerequisite to carrying out the methods according to the invention. The methods according to the invention may advantageously be practised using functional portions of a cyclin D3-encoding DNA/nucleic acid, particularly a functional portion of a cyclin D3-encoding nucleic acid as represented by SEQ ID NO: 1. A portion refers to a piece of DNA derived or prepared from an original (larger) DNA molecule. A portion may be prepared, for example, by making one or more deletions to, for example, the nucleic acid sequence of SEQ ID NO: 1 using techniques well known in the art.

Therefore according to the invention, there is provided, a method for improving plant yield, comprising introducing into a plant a functional portion of a nucleic acid as represented by SEQ ID NO: 1, which functional portion is under the control of a promoter capable of preferentially expressing the functional portion in shoots.

Another functional variant useful in the methods of the invention is an alternative splice variant of a cyclin D3-encoding nucleic acid, particularly an alternative splice variant of a cyclin D3-encoding nucleic acid as represented by the sequence of SEQ ID NO: 1. The term "alternative splice variant" as used herein encompasses variants of a nucleic acid sequence in which selected introns and/or exons have been excised, replaced or added. Such variants will be ones in which the biological activity of the protein remains unaffected, which can be achieved by selectively retaining functional segments of the protein. Such splice variants may be found in nature or may be manmade. Methods for making such splice variants are well known in the art.

Therefore, the invention also provides a method for improving yield in plants, comprising introducing into a plant an alternative splice variant of a cyclin D3-encoding nucleic acid, particularly an alternative splice variant of a cyclin D3-encoding nucleic acid as represented by SEQ ID NO: 1, which alternative splice variant is under the control of a promoter capable of preferentially expressing the splice variant in shoots.

Another variant useful in the methods of the invention is an allelic variant of a cyclin D3-encoding nucleic acid, particularly an allelic variant of a cyclin D3-encoding nucleic acid as represented by the sequence of SEQ ID NO: 1. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Therefore, the invention also provides a method for improving yield in plants, comprising introducing into a plant an allelic variant of a cyclin D3-encoding nucleic acid, particularly an allelic variant of a cyclin D3-encoding nucleic acid as represented by SEQ ID NO: 1, which allelic variant is under the control of a promoter capable of preferentially expressing the allelic variant in shoots.

Further advantageously, the methods according to the present invention may also be practised using homologues, derivatives or active fragments of a cyclin D3, preferably using homologues, derivatives or active fragments of a cyclin D3 as represented by SEQ ID NO: 2. Nucleic acids encoding homologues, derivatives or active fragments of an amino acid as represented by SEQ ID NO: 2 may readily be determined using routine techniques well known to persons skilled in the art.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues useful in the method according to the invention are those falling under the definition of a functional variant, i.e, having the ability to bind and activate a plant CDK and being a cyclin D3, as defined hereinabove. Additionally, the homologues may be characterised in terms of having in increasing order of preference at least 30%, 35%, 40%, 45%, 50%, 55%, 60%, 65%, 70%, 75%, 80%, 85%, 90%, 95% sequence identity to the amino acid sequence as represented by SEQ ID NO: 2 (see FIG. 3 which illustrates that cyclin D3s have a low percentage identity to each other, but nevertheless 30% identity to SEQ ID NO: 2 is sufficient to identify other cyclin D3s). In addition, the homologue may comprise one or more and preferably all of the following: (i) a cyclin box; (ii) an LxCxE motif (SEQ ID NO: 51) within the first 40 or so amino acids (which is characteristic of most cyclin Ds); and (iii) one or more and preferably all of the conserved regions identified by the boxes shown in FIG. 2 (as shown in FIG. 2, one mismatch within the boxes is allowed).

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to ancestral relationship.

Othologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database which may be found at: [[http://]] www.ncbi.nlm.nih.gov. If orthologues in rice were sought, the sequence in question would be blasted against, for example, the 28,469 full-length cDNA clones from *Oryza sativa* Nipponbare available at NCBI. BLASTn may be used when starting from nucleotides or TBLASTX when starting from the protein, with standard default values (expectation 10, alignment 50). The blast results may be filtered. The full-length sequences of either the filtered results or the non-filtered results are then blasted back (second blast) against the sequence in question (SEQ ID NO: 1 or 2). The results of the first and second blasts are then compared. In the case of large families, ClustalW is used followed by a neighbour joining tree to help visualize the clustering.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalenuly or non-covalently bound to the amino acid sequence, such as a reporter molecule which is bound to facilitate its detection, and non-naturally occurring amino acid residues relative to the amino acid sequence of a naturally-occurring protein.

"Active fragments" of a cyclin D3 protein encompasses at least five contiguous amino acid residues of a protein, which residues retain similar biological and/or functional activity to the naturally occurring protein. In any case, "homologues, derivatives and active fragments" are those falling under the definition of "functional variant" as defined hereinabove.

Methods for the search and identification of cyclin D3 homologues would be well within the realm of a person skilled in the art. Methods for the alignment of sequences for comparison are well known in the art, such methods include GAP, BESTFIT, BLAST, FASTA, ALIGN X (from vector NTI) and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. Homologues suitable for use in the methods of the invention, i.e. those having at least 30% sequence identity to the amino acid sequence represented by SEQ ID NO: 2, may be identified by taking full length cyclin D3 protein sequences and using a similarity/identity matrix generator, such as MatGAT (Matrix Global Alignment Tool) which calculates the similarity and identity between every pair of sequences in a given data set without requiring pre-alignment of the data. The program performs a series of pairwise alignments using the Myers and Miller global alignment algorithm (with a gap opening penalty of 12, and a gap extension penalty of 2). It then calculates similarity and identity using, for example, Blosum 60 as scoring matrix, and then places the results in a distance matrix.

Therefore, the invention also provides a method for improving plant yield, comprising introducing into a plant a nucleic acid encoding a homologue, derivative or active fragment of a cyclin D3, such as a homologue, derivative or active fragment of a cyclin D3 as represented by SEQ ID NO: 2, which homologue, derivative or active fragment is under the control of a promoter capable of preferentially expressing the nucleic acid in shoots.

The invention also provides genetic constructs and vectors to facilitate introduction and/or expression of the nucleotide sequences useful in the methods according to the invention.

Therefore, there is provided a gene construct comprising:
(i) a cyclin D3-encoding nucleic acid or functional variant thereof, preferably a cyclin D3-encoding nucleic acid as represented by SEQ ID NO: 1 or a functional variant thereof (as defined hereinabove), which nucleic acid encodes a cyclin D3 polypeptide or functional variant thereof, preferably a cyclin D3 polypeptide as represented by SEQ ID NO: 2 or a functional variant thereof;
(ii) a promoter capable of preferentially expressing the nucleic acid of (i) in shoots, particularly in the cell expansion zone of vegetative (aboveground) shoots; and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a nucleic acid encoding a cyclin D3 or a functional variant thereof (as defined hereinbefore), for example a cyclin D3-encoding nucleic acid as represented by SEQ ID NO: 1 or a functional variant thereof (as defined hereinabove)). The sequence of interest is operably linked to a promoter capable of preferentially expressing the sequence of interest in shoots. The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ.

The term "operably linked" as used herein refers to a functional linkage between the promoter sequence and the gene of interest, such that the promoter sequence is able to initiate transcription of the gene of interest.

Figure 5:
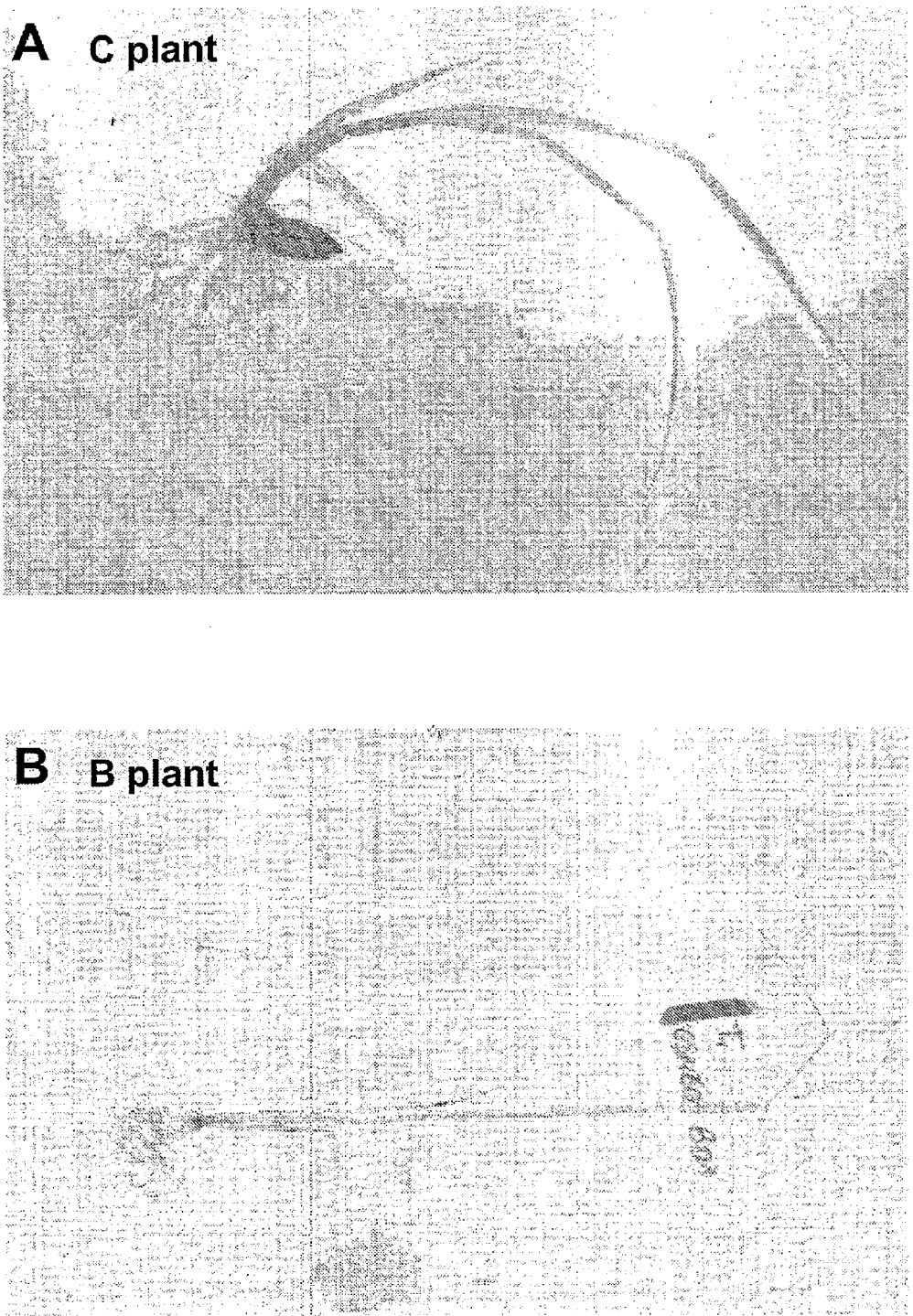
FIG. 5 shows photographs of GUS expression driven by a beta expansin promoter.

The nucleic acid encoding a cyclin D3 or a functional variant thereof, such as a cyclin D3-encoding nucleic acid as represented by SEQ ID NO: 1 or a functional variant thereof, is operably linked to a promoter capable of preferentially expressing the nucleic acid in shoots. Preferably, the promoter capable of preferentially expressing the nucleic acid in shoots has a comparable expression profile to a beta-expansin promoter, for example as shown in FIG. 5. A person skilled in the art will readily be able to identify promoters having a comparable expression profile to a beta-expansin promoter using routine techniques. More specifically, the promoter capable of preferentially expressing the nucleic acid in shoots is a promoter capable of driving expression in the cell expansion zone of a shoot, particularly in vegetative (aboveground) shoots. Most preferably, the promoter capable of preferentially expressing the nucleic acid in shoots is the beta-expansin promoter (SEQ ID NO: 3).

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of interest. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

The present invention also encompasses plants obtainable by the methods according to the present invention. The present invention therefore provides plants obtainable by the method according to the present invention, which plants comprise a nucleic acid encoding a cyclin D3 or functional variant thereof operably linked to a promoter capable of preferentially expressing the nucleic acid in shoots.

The invention also provides a method for the production of transgenic plants having improved yield, comprising introduction into a plant of a cyclin D3-encoding nucleic or functional variant thereof, particularly a cyclin D3-encoding nucleic acid as represented by SEQ ID NO: 1 or a functional variant thereof (as defined hereinabove), which nucleic acid is operably linked to a promoter capable of preferentially expressing the nucleic acid in shoots.

More specifically, the present invention provides a method for the production of transgenic plants having improved yield relative to corresponding wild type plants, which method comprises:
  (i) introducing into a plant or plant cell a cyclin D3-encoding nucleic acid or a functional variant thereof, preferably a cyclin D3-encoding nucleic acid as represented by SEQ ID NO: 1 or a functional variant thereof, which nucleic acid or functional variant thereof encodes a cyclin D3 polypeptide or functional variant thereof, which polypeptide is preferably as represented by SEQ ID NO: 2 or is a functional variant thereof and which nucleic acid or functional variant thereof is under the control of a promoter capable of preferentially expressing the nucleic acid in shoots, particularly in the cell expansion zone of vegetative (aboveground) shoots;
  (ii) cultivating the plant cell under conditions promoting regeneration and mature plant growth.

The nucleic acid or functional variant may be introduced directly into a plant cell or into the plant itself (including introduction into a tissue, organ or any other part of a plant). According to a preferred feature of the present invention, the nucleic acid is preferably introduced into a plant by transformation.

The term "introducing into a plant" refers principally to transformation of a plant with the particular nucleic acid in question (a cyclin D3-encoding nucleic acid or functional variant thereof), however the term also refers to other methods which result in the introduction into a plant of the particular nucleic acid in question, such as breeding techniques. Breeding techniques are well known to persons skilled in the art.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A., et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing a cyclin D3-encoding nucleic acid or functional variant thereof are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et aL (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 Jun.; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The methods according to the invention may also be performed without introducing a nucleic acid encoding a cyclin D3 or functional variant thereof into a plant. This may be achieved by introducing a genetic modification, preferably in the locus of a cyclin D3-encoding gene, so as to allow for expression of the gene preferentially in shoots. The locus of a gene as defined herein is taken to mean a genomic region, which includes the gene of interest and 10 KB up- or down stream of the coding region.

The genetic modification may be introduced, for example, by any one (or more) of the following methods: T-DNA activation, TILLING, mutagenesis, homologous recombination or, as discussed hereinabove, by introducing and expressing in a plant (cell) a cyclin D3-encoding nucleic acid or functional variant thereof, the nucleic acid being under the control of a promoter capable of preferentially expressing that nucleic acid in shoots.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. In order to achieve improved yield, the promoterto be introduced would be any promoter capable of preferentially expressing in shoots.

A genetic modification may also be introduced in the locus of a cyclin D3-encoding nucleic acid/gene using the technique of TILLING (Targeted Induced Local Lesions IN Genomes). This is a mutagenesis technology useful to generate and/or identify, and to eventually isolate mutagenised variants of a cyclin D3-encoding nucleic acid capable of exhibiting cyclin D3 biological activity. TILLING also allows selection of plants carrying such mutant variants. These mutant variants may even exhibit higher cyclin D3 activity than that exhibited by the gene in its natural form. TILLNG combines high-density mutagenesis with high-throughput screening methods. The steps typically followed in TILLING are: (a) EMS mutagenesis (Redei and Koncz, 1992; Feldmann et al, 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 Apr. 18(4):455-7, reviewed by Stemple 2004 (TILLING-a high-throughput harvest for functional genomics. Nat Rev Genet. February 2004; 5(2):145-50).

Mutagenesis may be used to generate variants of cyclin D3-encoding nucleic acids. Methods for generating mutant variants are well known in the art.

TDNA activation, TILLING and site-directed mutagenesis are examples of technologies that enable the generation of novel alleles and cyclin D3 variants.

Homologous recombination allows introduction in a genome of a selected nucleic acid at a defined selected position. Homologous recombination is a standard technology used routinely in biological sciences for lower organisms such as yeast or the moss physcomitrella. Methods for performing homologous recombination in plants have been described not only for model plants (Offringa et al. Extrachromosomal homologous recombination and gene targeting in plant cells after *Agrobacterum*-mediated transformation. 1990 EMBO J. 1990 October; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15(2):132-8). The nucleic acid to be targeted (which may be a cyclin D3-encoding nucleic acid or variant thereof as hereinbefore defined) need not be targeted to the locus of a cyclin D3-encoding gene, but may be introduced in, for example, regions of high expression. The nucleic acid to be targeted may be an improved allele used to replace the endogenous gene or may be introduced in addition to the endogenous gene.

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid molecule encoding a cyclin D3 operably linked to a promoter capable of expressing the nucleic acid in shoots. Preferred host cells according to the invention are plant cells. The invention also extends to harvestable parts of a plant such as but not limited to seeds, leaves, fruits, flowers, stem cultures, rhizomes, tubers and bulbs.

The present invention also encompasses the use of nucleic acids encoding cyclin D3s and the use of cyclin D3 polypeptides.

One such use of course relates to the use of a cyclin D3-encoding nucleic acid, operably linked to a promoter capable of preferentially expressing the nucleic acid in shoots, in improving the yield of plants, in particular in increasing aboveground area, increasing total seed number, increasing number of (filled) seeds, increasing seed weight and increasing harvest index, among others. The cyclin D3-encoding nucleic acid or functional variant thereof are as defined hereinabove. Preferred is a nucleic acid as represented by SEQ ID NO: 1, or a functional variant thereof as hereinbefore defined.

Nucleic acids encoding cyclin D3s and cyclin D3 polypeptides may also find use in breeding programmes. The cyclin D3 may be a nucleic acid as represented by SEQ ID NO: 1, or a functional variant thereof as hereinbefore defined; or the cyclin D3 may be an amino acid as represented by SEQ ID NO: 2 or a functional variant thereof as hereinbefore defined. For example, the cyclin D3-encoding nucleic acid or a part thereof may be on a chromosome (or a part thereof), preferably together with one or more related family members. In an example of such a breeding programme, a DNA marker is identified which may be genetically linked to a nucleic acid encoding a cyclin D3 protein in a plant, which gene may be a gene encoding the cyclin D3 protein itself or any other gene which may directly or indirectly influence expression of a gene encoding a cyclin D3 protein and/or activity of the cyclin D3 protein itself. This DNA marker may then be used in breeding programs to select plants having improved yield relative to corresponding wild type plants.

Allelic variants of a cyclin D3 may also be used in conventional breeding programmes, such as in marker-assisted breeding. Such breeding programmes sometimes require the introduction of allelic variations in the plants by mutagenic treatment of a plant. One suitable mutagenic method is EMS mutagenesis. Identification of allelic variants then takes place by, for example, PCR. This is followed by a selection step for selection of superior allelic variants of the sequence in question and which give improved yield in a plant relative to corresponding wild type plants. Selection is typically carried out by monitoring the yield in plants containing different allelic variants of the sequence in question, for example, different allelic variants of SEQ ID NO: 1. Monitoring yield can be done in a greenhouse or in the field. Further optional steps include crossing plants, in which the superior allelic variant was identified, with another plant. This could be used, for example, to make a combination of interesting phenotypic features.

Nucleic acids encoding cyclin D3s and cyclin D3 polypeptides may also find use as growth regulators. The cyclin D3 may be a nucleic acid as represented by SEQ ID NO: 1, or a functional variant thereof as hereinbefore defined; or the cyclin D3 may be an amino acid as represented by SEQ ID NO: 2 or a functional variant thereof as hereinbefore defined. Since these cyclin D3s are useful in improving yield in plants, the cyclin D3s would also be useful growth regulators, such as herbicides or growth stimulators. The present invention therefore provides a composition comprising a cyclin D3, together with a suitable carrier, diluent or excipient, for use as a growth regulator.

The methods according to the present invention result in plants having improved yield, as described hereinbefore. These advantageous characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 1 is a multiple alignment prepared using ClustalW and default values, followed by average distance tree computation. The cyclin D3 cluster is shown.

FIG. 2 is an alignment of known cyclin D3 protein sequences. The sequences were aligned using AlignX program from Vector NTI suite (InforMax, Bethesda, Md.). Multiple alignment was done with a gap opening penalty of 10 and a gap extension of 0.01. Minor manual editing was also carried out where necessary to better position some conserved regions. The line shown indicates the separation of cyclin D3s from other cyclins Ds. A number of motifs specific to cyclin D3s are boxed.

FIG. 3 is a similarity/identity matrix prepared using MatGAT (Matrix Global Alignment Tool) which calculates the similarity and identity between every pair of sequences in a given data set without requiring pre-alignment of the data. The program performs a series of pairwise alignments using the Myers and Miller global alignment algorithm (with a gap opening penalty of 12, and a gap extension penalty of 2). It then calculates similarity and identity using, for example, Blosum 60 as scoring matrix, and then places the results in a distance matrix. Sequence similarity is shown in the bottom half of the dividing line and sequence identity is shown in the top half of the dividing line. The sequence of SEQ ID NO: 2 is indicated as number 5 in the matrix. Sequences having at least 30% sequence identity to the sequence of SEQ ID NO: 2 encompass cyclin D3s.

Figure 4:
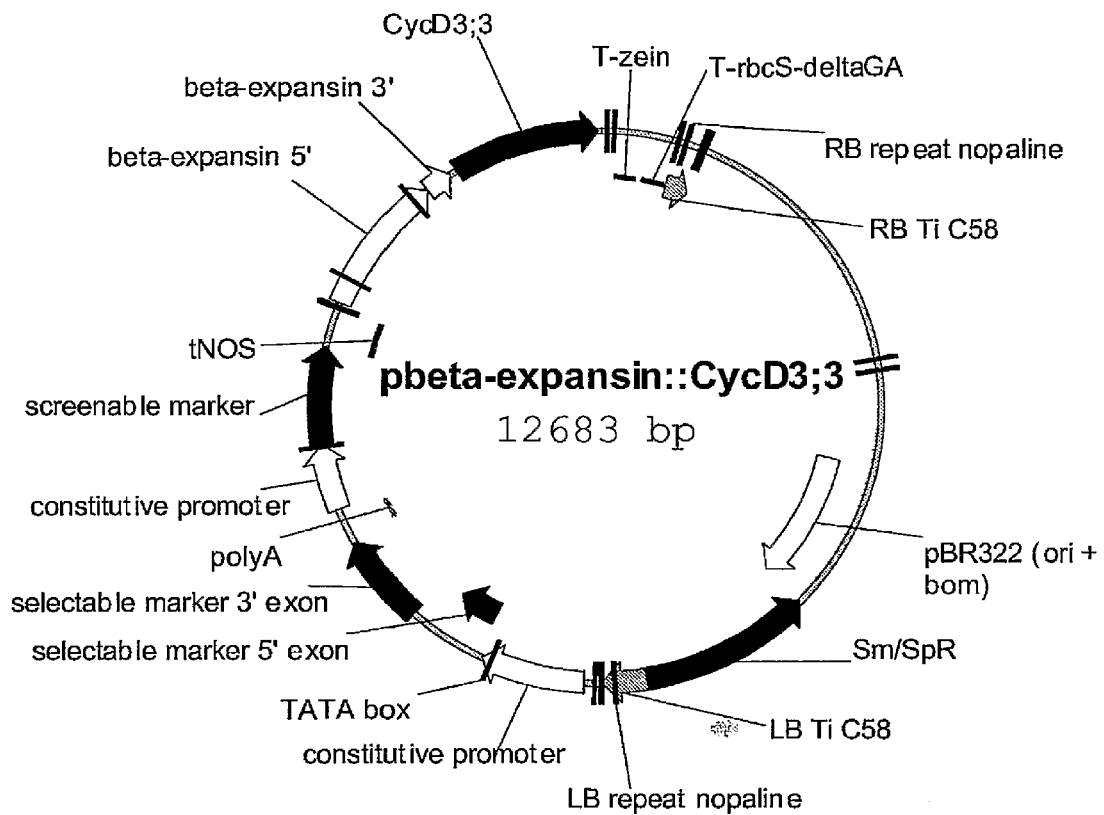
FIG. 4 is a binary vector for expression in *Oryza sativa* of the *Arabidopsis thaliana* Cyclin D3; 3 gene under the control of the beta-expansin promoter.

FIG. 4 is a binary vector for expression in *Oryza sativa* of the *Arabidopsis thaliana* CyclinD3; 3 gene under the control of the beta-expansin promoter.

FIG. 5 shows photographs of GUS expression driven by a beta expansin promoter. The photograph of the "C plant" is of a rice plant GUS stained when it had reached a size of about 5 cm. The photograph of the "B plant" is of a rice plant GUS stained when it had reached a size of about 10 cm. Promoters with comparable expression profiles may also be useful in the methods of the invention.

FIG. 6 details examples of sequences useful in performing the methods according to the present invention.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

The *Arabidopsis* Cyclin D3; 3 (internal reference CDS0018) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb and original number of clones was of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 μl PCR mix. Primers prm0360 (sense, start codon in bold, AttB1 site in italic: 5' GGGACAAGTTTGTACAAAAAAG-CAGGCTTCACAATGGCTTTAGAAGAGGAGGA 3' SEQ ID NO: 4) and prm0361 (reverse, complementary, stop codon in bold, AttB2 site in italic: 5' GGGGACCACTTTGTACAA-GAAAGCTGGGTTTAGCGAGGACTACTATAAGCA 3' SEQ ID NO: 5), which include the AttB sites for Gateway recombination, were used for PCR amplification. PCR was performed using Hifi Taq DNA polymerase in standard conditions. A PCR fragment of 1086 by was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p0443. Plasmid pDONR201 was purchased from Invitrogen, as part of the Gateway® technology.

Example 2

Vector Construction

The entry clone p0443 was subsequently used in an LR reaction with p3169, a destination vector used for *Oryza sativa* transformation. This vector contains as functional elements within the T-DNA borders: a plant selectable marker; a plant screenable marker; and a Gateway cassette intended for LR in vivo recombination with the sequence of interest already cloned in the entry clone. A beta-expansin promoter for expression in the expansion zone of vegetative (aboveground) shoots is located upstream of this Gateway cassette.

After the LR recombination step, the resulting expression vector (see FIG. 4) was transformed into *Agrobacterium* strain LBA4404 and subsequently to *Oryza sativa* plants. Transformed rice plants were allowed to grow and were then examined for the parameters described in Example 3.

Example 3

Evaluation and Results

Approximately 15 to 20 independent T0 rice transformants were generated. The primary transformants were transferred from tissue culture chambers to a greenhouse for growing and harvest of T1 seed. 5 events, of which the T1 progeny segregated 3:1 for presence/absence of the transgene, were retained. For each of these events, approximately 10 T1 seedlings containing the transgene (hetero- and homo-zygotes), and approximately 10 T1 seedlings lacking the transgene (nullizygotes), were selected by monitoring visual marker expression. The best T1 events were further evaluated in the T2 generation following the same procedure as for the T1 generation, but with more individuals per event.

Statistical Analysis: t-test and F-test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

3.1 Vegetative Growth Measurements:

The selected T1 plants (approximately 10 with the transgene and approximately 10 without the transgene) were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity each plant was passed several times through a digital imaging cabinet and imaged. At each time point digital images (2048×1536 pixels, 16 million colours) were taken of each plant from at least 6 different angles. The parameters described below were derived in an automated way from all the digital images of all the plants, using image analysis software.

3.1.1 Aboveground Plant Area

Plant aboveground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The results of the T1 and T2 evaluation are shown in Table 1 below. The percentage difference between transgenic plants and corresponding nullizygotes is shown. The p value of the F test was significant in both the T1 and T2 evaluation indicating an overall effect of the presence of the transgene on aboveground area.

TABLE 2

| | Aboveground area Aboveground area | |
|---|---|---|
| | % Difference | P value |
| T1 Overall | 15 | 0.001 |
| T2 Overall | 18 | 0.0003 |

3.2 Seed-Related Parameter Measurements

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

3.2.1 Total Number of Seeds

Total seed number per plant: was measured by counting the number of husks harvested from a plant. The results of the T1 and T2 evaluations are shown in Table 2 below. The percentage difference between transgenic plants and corresponding nullizygotes is shown. The p value of the F test was significant for both the T1 and T2 evaluation indicating that the presence of the transgene has a significant effect on the total number of seeds produced.

TABLE 3

| | Total Number of Seeds Total number of seeds | |
|---|---|---|
| | % Difference | P value |
| T1 Overall | 27 | 0.0039 |
| T2 Overall | 19 | 0.0096 |

3.2.2 Number of Filled Seeds

The number of filled seeds was determined by counting the number of filled husks that remained after the separation step. The results of the T1 and T2 evaluations are shown in Table 3 below. The percentage difference between transgenic plants and corresponding nullizygotes is shown. The p value of the F test was significant in both the T1 and T2 evaluations indicating that the presence of the transgene significantly increases the number of filled seeds produced.

TABLE 4

| | Number of Filled Seeds Total number of filled seeds | |
|---|---|---|
| | % Difference | P value |
| T1 Overall | 52 | 0.0002 |
| T2 Overall | 35 | 0.0007 |

3.2.3 Total Seed Weight

The total seed yield was measured by weighing all filled husks harvested from a plant. The results of the T1 and the T2 evaluations are shown in Table 4 below. The percentage difference between transgenic plants and corresponding nullizygotes is shown. The p value of the F test was significant for both the T1 and T2 evaluations indicating that the presence of the transgene significantly increases seed weight.

TABLE 5

| | Total Seed Weight Total Seed Weight | |
|---|---|---|
| | % difference | P value |
| T1 Overall | 42 | 0.0017 |
| T2 Overall | 38 | 0.0005 |

3.2.4 Harvest Index of Plants

The harvest index in the present invention is defined as the ratio between the total seed yield and the above ground area ($mm^2$), multiplied by a factor $10^6$. The results of the T1 and T2 evaluation are shown in Table 5 below. The percentage difference between transgenic plants and corresponding nullizygotes is shown. The p value of the F test was significant for both the T1 and T2 evaluations indicating that the presence of the transgene significantly increases the harvest index.

TABLE 6

| | Harvest Index Harvest index | |
|---|---|---|
| | % Difference | P value |
| T1 Overall | 28 | 0.0022 |
| T2 Overall | 20 | 0.0086 |

Example 4

Comparative Data pOleosin::Cyclin D3; 3

Plants containing the above construct were produced and evaluated using the same procedures as described above for pBeta-expansin::cyclin D3; 3. The results of the T1 evaluation are shown in tables 6 to 8 below. The percentage difference between transgenic plants and corresponding nullizygotes is shown in each of the tables. The p value of the F test is also shown.

TABLE 7

| Aboveground Area | | |
|---|---|---|
| Aboveground area | | |
| | % Difference | P value |
| T1 Overall | −12 | 0.0083 |

The p value of the F test was significant indicating that the expression of the transgene driven by this promoter significantly decreases aboveground area.

TABLE 8

| Total Seed Weight | | |
|---|---|---|
| Total Seed Weight | | |
| | % difference | P value |
| T1 Overall | −15 | 0.0858 |

The results show that the total weight of the seeds of transgenic plants was lower than the total seed weight of corresponding nullizygotes.

TABLE 9

| Number of Filled Seeds | | |
|---|---|---|
| Number of Filled Seeds | | |
| | % difference | P value |
| T1 Overall | −17 | 0.0572 |

The results show that the number of filled seeds of transgenic plants was lower than the number of filled seeds of corresponding nulllizygotes.

Example 5

GUS Expression Driven by Beta Expansin Promoter

The beta-expansin promoter was cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests.

In order to clone the promoter in front of a reporter gene, each entry clone was subsequently used in an "LR recombination reaction" (Gateway™) with a destination vector. This destination vector was designed to operably link the promoter to the *Escheichia coli* beta-glucuronidase (GUS) gene via the substitution of the Gateway recombination cassette in front of the GUS gene. The resulting reporter vectors, comprising the promoter operably linked to GUS were are subsequently transformed into *Agrobacterium* strain LBA4044 and subsequently into rice plants using standard transformation techniques.

Transgenic rice plants were generated from transformed cells. Plant growth was performed under normal conditions.

The plants or plant parts to be tested were covered with 90% ice-cold acetone and incubated for 30 min at 4° C. After 3 washes of 5 min with Tris buffer [15.76 g Trizma HCl (Sigma T3253)+2,922 g NaCl in 1 litre bi-distilled water, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

The invention claimed is:

1. A method for improving plant yield, comprising introducing into a plant a nucleic acid encoding a cyclin D3 under the control of a promoter which preferentially directs expression of said nucleic acid in shoots and selecting a plant having improved yield relative to a corresponding wild type plant.

2. The method according to claim 1, wherein said improved yield is increased seed yield.

3. The method according to claim 1, wherein said improved yield is increased aboveground area.

4. The method according to claim 2, wherein said increased seed yield is selected from the group consisting of (i) increased seed biomass; (ii) increased number of (filled) seeds; (iii) increased seed size; (iv) increased seed volume; (v) increased harvest index; and (vi) increased thousand kernel weight.

5. The method according to claim 1, wherein the nucleic acid is obtained from a plant.

6. The method according to claim 1, wherein the cyclin D3 comprises an amino acid sequence comprising (a) a cyclin box; (b) an LXCXE motif (SEQ ID NO: 51) within about the first 40 amino acids; and (c) one or more of the conserved regions (K/M/T/R)PWM (SEQ ID NO: 52), C(E/H/D), or K(R/G)(K/M).

7. A method for the production of a transgenic plant having improved yield relative to a corresponding wild type plant, which method comprises:
   (i) introducing into a plant or plant cell a cyclin D3-encoding nucleic acid which comprises a nucleic acid which encodes a cyclin D3 which cyclin D3 comprises an amino acid sequence comprising (i) a cyclin box, (ii) an LXCXE motif (SEQ ID NO: 51) within about the first 40 amino acids, and (iii) one or more of the conserved regions (KIM/T/R)PWM (SEQ ID NO: 52), C(E/H/D), or K(R/G)(K/M); and which nucleic acid is operably linked to a promoter which preferentially directs expression of said nucleic acid in shoots;
   (ii) cultivating the plant cell under conditions promoting regeneration and mature plant growth; and
   (iii) selecting a plant having improved yield relative to a corresponding wild type plant.

8. The method according to claim 7, wherein said improved yield is increased seed yield.

9. The method according to claim 8, wherein said increased yield comprises increased aboveground area and wherein said increased seed yield is selected from: (i) increased seed biomass; (ii) increased number of (filled) seeds; (iii) increased seed size; (iv) increased seed volume; (v) increased harvest index; and (iv) increased thousand kernel weight.

10. A plant obtained by the method of claim 1.

11. A construct comprising:
(i) a cyclin D3-encoding nucleic acid which comprises a nucleic acid encoding a cyclin D3 polypeptide comprising an amino acid sequence comprising (i) a cyclin box, (ii) an LXCXE motif (SEQ ID NO: 51) within about the first 40 amino acids, and (iii) one or more of the conserved regions (K/M/T/R)PWM (SEQ ID NO: 52), C(E/H/D), or K(R/G)(K/M);
(ii) a promoter which preferentially directs expression of the nucleic acid of (i) in shoots; and optionally
(iii) a transcription termination sequence.

12. A plant transformed with the construct according to claim 11.

13. A transgenic plant having improved yield relative to a corresponding wild type plant comprising a nucleic acid encoding a cyclin D3 which cyclin D3 comprises an amino acid sequence comprising (a) a cyclin box; (b) an LXCXE motif (SEQ ID NO: 51) within about the first 40 amino acids; and (c) one or more of the conserved regions (K/M/T/R)PWM (SEQ ID NO: 52), C(E/H/D), or K(R/G)(K/M) under the control of a promoter which preferentially directs expression of said nucleic acid in shoots.

14. The transgenic plant according to claim 10, wherein said plant is a monocotyledonous plant.

15. Harvestable parts of a transgenic plant according to claim 10, wherein the harvestable parts comprise the introduced nucleic acid.

16. Harvestable parts according to claim 15, wherein said harvestable parts are seeds.

17. The method according to claim 1, wherein said nucleic acid comprises the nucleic acid sequence of SEQ ID NO: 1, a nucleic acid encoding a cyclin D3 comprising the amino acid of SEQ ID NO: 2, or a nucleic acid encoding a cyclin D3 polypeptide comprising an amino acid sequence comprising (i) a cyclin box, (ii) an LXCXE motif (SEQ ID NO: 51) within about the first 40 amino acids, and (iii) one or more of the conserved regions (K/M/T/R)PWM (SEQ ID NO: 52), C(E/H/D), or K(R/G)(K/M).

18. The transgenic plant according to claim 14, wherein said plant is selected from the group consisting of sugar cane, cereal, rice, maize, wheat, barley, millet, rye oats, and sorghum.

19. Harvestable parts of a transgenic plant according to claim 12, wherein the harvestable parts comprise the construct.

20. Harvestable parts according to claim 19, wherein said harvestable parts are seeds.

21. The method of claim 7, wherein the nucleic acid comprises the nucleic acid sequence of SEQ ID NO: 1 or a nucleic acid sequence encoding a cyclin D3 polypeptide comprising the amino acid sequence of SEQ ID NO: 2.

22. The method according to claim 7, wherein the promoter comprises the nucleic acid sequence of SEQ ID NO: 3.

23. The construct of claim 11, wherein the nucleic acid comprises the nucleic acid sequence of SEQ ID NO: 1 or a nucleic acid sequence encoding a cyclin D3 polypeptide comprising the amino acid sequence of SEQ ID NO: 2.

24. The plant of claim 13, wherein the promoter comprises the nucleic acid sequence of SEQ ID NO: 3.

25. The plant of claim 13, wherein the nucleic acid comprises the nucleic acid sequence of SEQ ID NO: 1 or a nucleic acid sequence encoding a cyclin D3 polypeptide comprising the amino acid sequence of SEQ ID NO: 2.

26. The method of claim 1, wherein the promoter comprises the nucleic acid sequence of SEQ ID NO: 3.

27. The construct of claim 11, wherein the promoter comprises the nucleic acid sequence of SEQ ID NO: 3.

* * * * *

UNITED STATES PATENT AND TRADEMARK OFFICE
CERTIFICATE OF CORRECTION

PATENT NO. : 7,872,172 B2  Page 1 of 1
APPLICATION NO. : 10/592277
DATED : January 18, 2011
INVENTOR(S) : Valerie Frankard It is certified that error appears in the above-identified patent and that said Letters Patent is hereby corrected as shown below:

In claim 7, at column 116, line number 52, "regions (KIM/T/R)PWM (SEQ ID NO: 52), C(E/H/D)," should read -- regions (K/M/T/R)PWM (SEQ ID NO: 52), C(E/H/D), --

In claim 18, at column 118, line number 7, "cereal, rice, maize, wheat, barley, millet, rye oats, and sor-" should read -- cereal, rice, maize, wheat, barley, millet, rye, oats, and sor- --

Signed and Sealed this
Fourteenth Day of June, 2011

David J. Kappos
*Director of the United States Patent and Trademark Office*

SEQUENCE LISTING

<160> NUMBER OF SEQ ID NOS: 52

<210> SEQ ID NO 1
<211> LENGTH: 1086
<212> TYPE: DNA
<213> ORGANISM: Arabidopsis thaliana

<400> SEQUENCE: 1

```
atggctttag aagaggagga agagagtcaa aacgcaccgt tttgtgttct tgatggtctt      60
ttctgtgagg aagagagtga gtttcacgaa caagtagatt tgtgcgacga gagtgttgaa     120
aagtttcctt ttttaaatct gggtttgtct gatcatgata tgttgtggga tgatgatgag     180
ttatcaactt tgatttcgaa acaagaaccg tgtctttatg acgaaatctt agatgatgag     240
tttctggttt tgtgtcgtga aaaggctctt gattggattt ttaaagtgaa atctcattat     300
gggtttaatt cattgacggc tcttttagct gttaattact tcgataggtt tattacaagc     360
aggaagtttc agacagataa gccatggatg tctcagctta ctgctttggc ttgtctgtct     420
```

-continued

```
ttagctgcta aggttgaaga gatccgtgtt ccttttctct tagattttca agtggaagaa    480
gcaagatatg tctttgaagc taagactata cagagaatgg agcttcttgt tctgtctact    540
cttgactgga ggatgcatcc tgtgactcca atctcgtttt tcgatcacat tattcgacga    600
tacagcttta aatctcatca tcaattggag ttcttgagta gatgtgaatc tttattactc    660
tccattattc ctgattcgag atttctgagt tttagtcctt ctgtgttagc cactgcaata    720
atggtctctg ttattagaga tttgaagatg tgtgacgaag ctgtatacca atctcagctc    780
atgactctac tcaaagttga ttcggagaag gtaaataaat gctatgagtt agtgttagac    840
cacagtccaa gcaagaaaag gatgatgaat tggatgcaac aacccgctag tccgatcggt    900
gtgtttgatg cgtcattcag ttctgatagc tcgaatgagt cgtgggttgt gtctgcttct    960
gcttcagtgt cgtcttcacc atcttcgagg cctttgctca agaggagaag agtgcaagag   1020
cagcagatga ggctatcttc aataaaccga atgtttttcg atgtgcttag tagtagtcct   1080
cgctaa                                                              1086
```

<210> SEQ ID NO 2
<211> LENGTH: 361
<212> TYPE: PRT
<213> ORGANISM: Arabidopsis thaliana

<400> SEQUENCE: 2

```
Met Ala Leu Glu Glu Glu Glu Ser Gln Asn Ala Pro Phe Cys Val
1               5                   10                  15

Leu Asp Gly Leu Phe Cys Glu Glu Ser Glu Phe His Glu Gln Val
            20                  25                  30

Asp Leu Cys Asp Glu Ser Val Glu Lys Phe Pro Phe Leu Asn Leu Gly
        35                  40                  45

Leu Ser Asp His Asp Met Leu Trp Asp Asp Glu Leu Ser Thr Leu
    50                  55                  60

Ile Ser Lys Gln Glu Pro Cys Leu Tyr Asp Glu Ile Leu Asp Asp Glu
65                  70                  75                  80

Phe Leu Val Leu Cys Arg Glu Lys Ala Leu Asp Trp Ile Phe Lys Val
                85                  90                  95

Lys Ser His Tyr Gly Phe Asn Ser Leu Thr Ala Leu Leu Ala Val Asn
            100                 105                 110

Tyr Phe Asp Arg Phe Ile Thr Ser Arg Lys Phe Gln Thr Asp Lys Pro
        115                 120                 125

Trp Met Ser Gln Leu Thr Ala Leu Ala Cys Leu Ser Leu Ala Ala Lys
    130                 135                 140

Val Glu Glu Ile Arg Val Pro Phe Leu Leu Asp Phe Gln Val Glu Glu
145                 150                 155                 160

Ala Arg Tyr Val Phe Glu Ala Lys Thr Ile Gln Arg Met Glu Leu Leu
                165                 170                 175

Val Leu Ser Thr Leu Asp Trp Arg Met His Pro Val Thr Pro Ile Ser
            180                 185                 190

Phe Phe Asp His Ile Ile Arg Arg Tyr Ser Phe Lys Ser His His Gln
        195                 200                 205

Leu Glu Phe Leu Ser Arg Cys Glu Ser Leu Leu Ser Ile Ile Pro
    210                 215                 220

Asp Ser Arg Phe Leu Ser Phe Ser Pro Ser Val Leu Ala Thr Ala Ile
225                 230                 235                 240

Met Val Ser Val Ile Arg Asp Leu Lys Met Cys Asp Glu Ala Val Tyr
                245                 250                 255
```

Gln Ser Gln Leu Met Thr Leu Leu Lys Val Asp Ser Glu Lys Val Asn
        260                 265                 270

Lys Cys Tyr Glu Leu Val Leu Asp His Ser Pro Ser Lys Lys Arg Met
        275                 280                 285

Met Asn Trp Met Gln Gln Pro Ala Ser Pro Ile Gly Val Phe Asp Ala
        290                 295                 300

Ser Phe Ser Ser Asp Ser Ser Asn Glu Ser Trp Val Ser Ala Ser
305                 310                 315                 320

Ala Ser Val Ser Ser Pro Ser Ser Glu Pro Leu Leu Lys Arg Arg
            325                 330                 335

Arg Val Gln Glu Gln Gln Met Arg Leu Ser Ser Ile Asn Arg Met Phe
        340                 345                 350

Phe Asp Val Leu Ser Ser Ser Pro Arg
        355                 360

```
<210> SEQ ID NO 3
<211> LENGTH: 1243
<212> TYPE: DNA
<213> ORGANISM: Oryza sativa

<400> SEQUENCE: 3
aaaaccaccg agggacctga tctgcaccgg ttttgatagt tgagggaccc gttgtgtctg      60
gttttccgat cgagggacga aaatcggatt cggtgtaaag ttaagggacc tcagatgaac     120
ttattccgga gcatgattgg aagggagga cataaggccc atgtcgcatg tgtttggacg     180
gtccagatct ccagatcact cagcaggatc ggccgcgttc gcgtagcacc cgcggtttga     240
ttcggcttcc cgcaaggcgg cggccggtgg ccgtgccgcc gtagcttccg ccggaagcga     300
gcacgccgcc gccgccgacc cggctctgcg tttgcaccgc cttgcacgcg atacatcggg     360
atagatagct actactctct ccgtttcaca atgtaaatca ttctactatt ttccacattc     420
atattgatgt taatgaatat agacatatat atctatttag attcattaac atcaatatga     480
atgtaggaaa tgctagaatg acttacattg tgaattgtga atggacgaa gtacctacga     540 tggatggatg caggatcatg aaagaattaa tgcaagatcg tatctgccgc atgcaaaatc     600
ttactaattg cgctgcatat atgcatgaca gcctgcatgc gggcgtgtaa gcgtgttcat     660
ccattaggaa gtaaccttgt cattacttat accagtacta catactatat agtattgatt     720
tcatgagcaa atctacaaaa ctggaaagca ataaggaata cgggactgga aaagactcaa     780
cattaatcac caaatatttc gccttctcca gcagaatata tatctctcca tcttgatcac     840
tgtacacact gacagtgtac gcataaacgc agcagccagc ttaactgtcg tctcaccgtc     900
gcacactggc cttccatctc aggctagctt tctcagccac ccatcgtaca tgtcaactcg     960
gcgcgcgcac aggcacaaat tacgtacaaa acgcatgacc aaatcaaaac caccggagaa    1020
gaatcgctcc cgcgcgcggc ggcggcgcgc acgtacgaat gcacgcacgc acgcccaacc    1080
ccacgacacg atcgcgcgcg acgccggcga caccggccat ccaccccgcgc cctcacctcg   1140 ccgactataa atacgtaggc atctgcttga tcttgtcatc catctcacca ccaaaaaaaa    1200
aggaaaaaaa aacaaaacac accaagccaa ataaaagcga caa                      1243

<210> SEQ ID NO 4
<211> LENGTH: 54
<212> TYPE: DNA
<213> ORGANISM: Artificial sequence
<220> FEATURE:
<223> OTHER INFORMATION: primer prm0360
```

```
<400> SEQUENCE: 4
ggggacaagt ttgtacaaaa aagcaggctt cacaatggct ttagaagagg agga        54

<210> SEQ ID NO 5
<211> LENGTH: 51
<212> TYPE: DNA
<213> ORGANISM: Artificial sequence
<220> FEATURE:
<223> OTHER INFORMATION: primer prm0361

<400> SEQUENCE: 5
ggggaccact ttgtacaaga aagctgggtt tagcgaggac tactataagc a           51

<210> SEQ ID NO 6
<211> LENGTH: 343
<212> TYPE: PRT
<213> ORGANISM: Antirrhinum majus

<400> SEQUENCE: 6
```

Met Tyr Gln Gln Asn Ser Pro Ser Leu Cys Phe Asp Ala Leu Tyr Cys
1               5                   10                  15

Glu Glu Glu Gln Asn Trp Asp Asn Gly Glu Ile Ile Asn Asp Cys Phe
            20                  25                  30

Ile Glu Glu Gln Glu Pro Phe Ser Asp Leu Leu Lys His Asp Leu Leu
        35                  40                  45

Cys Gly Val Asp Asp Asp Asp Asp Lys Glu Glu Leu Ser Ser Leu
    50                  55                  60

Leu Cys Lys Glu Gln Glu Tyr Glu Leu Tyr Arg Val Leu Glu Asp Asn
65                  70                  75                  80

Pro Ser Leu Ala Lys Ala Arg Asp Glu Ala Val Glu Trp Met Phe Lys
                85                  90                  95

Val Ile Gly Tyr Tyr Ser Phe Ser Ala Leu Thr Ala Val Leu Ala Val
            100                 105                 110

Asn Tyr Leu Asp Arg Phe Leu Cys Thr Phe Gln Phe Gln Gln Asp Lys
        115                 120                 125

Pro Trp Met Tyr Gln Leu Ala Ala Val Ala Cys Leu Ser Leu Ala Ala
    130                 135                 140

Lys Val Glu Glu Thr Gln Val Pro Leu Leu Leu Asp Leu Gln Val Glu
145                 150                 155                 160

Glu Ser Lys Tyr Val Phe Glu Ser Lys Thr Ile Gln Arg Met Glu Leu
                165                 170                 175

Leu Val Leu Ser Thr Leu Lys Trp Lys Met Asn Pro Val Thr Pro Ile
            180                 185                 190

Ser Phe Leu Glu Tyr Ile Ala Arg Arg Leu Ala Leu Lys Ser His Leu
        195                 200                 205

Cys Lys Glu Phe Leu Asn Arg Cys Glu Cys Leu Leu Leu Ser Leu Ile
    210                 215                 220

Thr Asp Cys Arg Phe Met Cys His Leu Pro Ser Ala Leu Ala Thr Ala
225                 230                 235                 240

Thr Met Leu Tyr Val Ile Ser Ser Leu Glu Pro Cys Ile Gly Val Glu
                245                 250                 255

Tyr Gln Asp Gln Leu Ile Asn Ile Leu Gly Ile Asn Lys Asp Lys Val
            260                 265                 270

Glu Glu Cys Cys Lys Leu Ile Gln Glu Val Ala Thr Ser Val His Phe
        275                 280                 285

```
Gln Ser Gly Asn Lys Arg Lys Phe Gly Ser Leu Pro Tyr Ser Pro Lys
        290                 295                 300

Gly Val Val Asp Ile Ser Phe Ser Cys Asp Asp Ser Trp Pro Leu Asp
305                 310                 315                 320

Ser Thr Ala Ser Val Ser Ser Pro Glu His Leu Ser Lys Lys Ile
                325                 330                 335

Lys Thr Gln Asn Pro Asp His
            340

<210> SEQ ID NO 7
<211> LENGTH: 361
<212> TYPE: PRT
<213> ORGANISM: Antirrhinum majus

<400> SEQUENCE: 7

Met Leu Phe Ser His Ser Gln Gln Thr His Leu Gln Asn Pro Ile Phe
1               5                   10                  15

Asp Ala Leu Leu Cys Asn Glu Glu His Phe Asp Glu Asp Leu Asp Leu
                20                  25                  30

Gly Ser Gly Leu Lys Asp Pro Gly Phe Ile Asn Gln Ile His His Asn
            35                  40                  45

Gln Lys Lys Glu Glu Pro Phe Thr Thr Phe Leu Phe Glu His Asp Leu
50                  55                  60

Leu Trp Glu Asp Asp Glu Leu Val Asn Leu Ser Lys Glu Lys Glu
65                  70                  75                  80

Gln Glu Gln Gln Ala His Leu Gly Tyr Asp Asp Val Met Asp Ser Asp
                85                  90                  95

Gly Phe Leu Lys Arg Val Arg Asn Glu Gly Ile Lys Trp Met Leu Lys
            100                 105                 110

Val Ile Gly His Tyr Gly Phe Asn Ala Met Thr Ala Val Leu Ala Val
        115                 120                 125

Asn Tyr Tyr Asp Arg Phe Ile Thr Asn Val Gly Phe Gln Lys Asp Lys
130                 135                 140

Pro Trp Met Ser Gln Leu Ala Ala Val Ala Cys Leu Ser Val Lys Val
145                 150                 155                 160

Glu Glu Thr Gln Val Pro Leu Leu Asp Phe Gln Val Glu Glu Ser
                165                 170                 175

Lys Tyr Val Phe Glu Ala Lys Thr Ile Gln Arg Met Glu Leu Leu Val
            180                 185                 190

Leu Thr Thr Leu Lys Trp Lys Met Asn Pro Val Thr Pro Ile Ser Phe
        195                 200                 205

Phe Asp His Ile Val Arg Arg Phe Glu Leu Met Asn Asn Val Gln Cys
210                 215                 220

Glu Phe Met Lys Arg Cys Glu Ser Val Ile Leu Ser Ile Ile Thr Asp
225                 230                 235                 240

Tyr Arg Phe Val Arg Tyr Leu Pro Ser Val Ala Ala Ala Thr Met
                245                 250                 255

Ile Tyr Val Ile Lys Glu Leu Tyr Pro Cys Asp Ala Leu Glu Tyr Gln
            260                 265                 270

Asn Glu Phe Val Thr Val Leu Arg Thr Ser Lys Glu Lys Thr Asp Asp
        275                 280                 285

Cys His Met Leu Ile Thr Glu Val Ile Asn Asn Gln Ser Tyr Ile Leu
290                 295                 300

Cys His Lys Arg Lys Tyr Gly Ser Ile Pro Ser Ser Pro Asn Gly Val
305                 310                 315                 320
```

Ile Asp Ala Tyr Phe Ser Ser Asp Gly Ser Asn Asp Ser Trp Ser Ala
              325                 330                 335

Val Ser Ser Val Ser Ser Ser Pro Glu Pro Val Phe Lys Arg Ile Arg
            340                 345                 350

Ala Ile Gly Gly Ala Asn Pro Pro His
        355                 360

<210> SEQ ID NO 8
<211> LENGTH: 376
<212> TYPE: PRT
<213> ORGANISM: Arabidopsis thaliana

<400> SEQUENCE: 8

Met Ala Ile Arg Lys Glu Glu Ser Arg Glu Glu Gln Ser Asn Ser
1               5                  10                  15

Phe Leu Leu Asp Ala Leu Tyr Cys Glu Glu Lys Trp Asp Asp Glu
                20                  25                  30

Gly Glu Glu Val Glu Glu Asn Ser Ser Leu Ser Ser Ser Ser Pro
            35                  40                  45

Phe Val Val Leu Gln Gln Asp Leu Phe Trp Glu Asp Glu Asp Leu Val
        50                  55                  60

Thr Leu Phe Ser Lys Glu Glu Glu Gln Gly Leu Ser Cys Leu Asp Asp
65                  70                  75                  80

Val Tyr Leu Ser Thr Asp Arg Lys Glu Ala Val Gly Trp Ile Leu Arg
                85                  90                  95

Val Asn Ala His Tyr Gly Phe Ser Thr Leu Ala Ala Val Leu Ala Ile
            100                 105                 110

Thr Tyr Leu Asp Lys Phe Ile Cys Ser Tyr Ser Leu Gln Arg Asp Lys
        115                 120                 125

Pro Trp Met Leu Gln Leu Val Ser Val Ala Cys Leu Ser Leu Ala Ala
130                 135                 140

Lys Val Glu Glu Thr Gln Val Pro Leu Leu Leu Asp Phe Gln Val Glu
145                 150                 155                 160

Glu Thr Lys Tyr Val Phe Glu Ala Lys Thr Ile Gln Arg Met Glu Leu
                165                 170                 175

Leu Ile Leu Ser Thr Leu Glu Trp Lys Met His Leu Ile Thr Pro Ile
            180                 185                 190

Ser Phe Val Asp His Ile Ile Arg Arg Leu Gly Leu Lys Asn Asn Ala
        195                 200                 205

His Trp Asp Phe Leu Asn Lys Cys His Arg Leu Leu Leu Ser Val Ile
    210                 215                 220

Ser Asp Ser Arg Phe Val Gly Tyr Leu Pro Ser Val Val Ala Ala Ala
225                 230                 235                 240

Thr Met Met Arg Ile Ile Glu Gln Val Asp Pro Phe Asp Pro Leu Ser
                245                 250                 255

Tyr Gln Thr Asn Leu Leu Gly Val Leu Asn Leu Thr Lys Glu Lys Val
            260                 265                 270

Lys Thr Cys Tyr Asp Leu Ile Leu Gln Leu Pro Val Asp Arg Ile Cys
        275                 280                 285

Leu Gln Ile Gln Ile Gln Ser Ser Lys Lys Arg Lys Ser His Asp Ser
    290                 295                 300

Ser Ser Ser Leu Asn Ser Pro Ser Cys Val Ile Asp Ala Asn Pro Phe
305                 310                 315                 320

Asn Ser Asp Glu Ser Ser Asn Asp Ser Trp Ser Ala Ser Ser Cys Asn

```
                    325                 330                 335
Pro Pro Thr Ser Ser Ser Pro Gln Gln Pro Leu Lys Lys
            340                 345                 350

Met Arg Gly Ala Glu Glu Asn Glu Lys Lys Pro Ile Leu His Leu
            355                 360                 365

Pro Trp Ala Ile Val Ala Thr Pro
    370                 375

<210> SEQ ID NO 9
<211> LENGTH: 367
<212> TYPE: PRT
<213> ORGANISM: Arabidopsis thaliana

<400> SEQUENCE: 9

Met Ala Leu Glu Lys Glu Glu Ala Ser Gln Asn Gly Ala Phe Cys
1               5                   10                  15

Val Leu Asp Gly Leu Tyr Cys Glu Glu Thr Gly Phe Val Glu Asp
                20                  25                  30

Asp Leu Asp Asp Gly Asp Leu Asp Phe Leu Glu Lys Ser Asp Glu
            35                  40                  45

Ser Val Val Lys Phe Gln Phe Leu Pro Leu Leu Asp Met Phe Leu Trp
    50                  55                  60

Asp Asp Asp Glu Ile Leu Ser Leu Ile Ser Lys Glu Asn Glu Thr Asn
65                  70                  75                  80

Pro Cys Phe Gly Glu Gln Ile Leu Asp Gly Phe Leu Val Ser Cys Arg
                85                  90                  95

Lys Glu Ala Leu Asp Trp Val Leu Arg Val Lys Ser His Tyr Gly Phe
            100                 105                 110

Thr Ser Leu Thr Ala Ile Leu Ala Val Asn Tyr Phe Asp Arg Phe Met
        115                 120                 125

Thr Ser Ile Lys Leu Gln Thr Asp Lys Pro Trp Met Ser Gln Leu Val
    130                 135                 140

Ala Val Ala Ser Leu Ser Leu Ala Ala Lys Val Glu Glu Ile Gln Val
145                 150                 155                 160

Pro Leu Leu Leu Asp Leu Gln Val Glu Glu Ala Arg Tyr Leu Phe Glu
                165                 170                 175

Ala Lys Thr Ile Gln Arg Met Glu Leu Leu Ile Leu Ser Thr Leu Gln
            180                 185                 190

Trp Arg Met His Pro Val Thr Pro Ile Ser Phe Phe Asp His Ile Ile
        195                 200                 205

Arg Arg Phe Gly Ser Lys Trp His Gln Gln Leu Asp Phe Cys Arg Lys
    210                 215                 220

Cys Glu Arg Leu Leu Ile Ser Val Ile Ala Asp Thr Arg Phe Met Arg
225                 230                 235                 240

Tyr Phe Pro Ser Val Leu Ala Thr Ala Ile Met Ile Leu Val Phe Glu
                245                 250                 255

Glu Leu Lys Pro Cys Asp Glu Val Glu Tyr Gln Ser Gln Ile Thr Thr
            260                 265                 270

Leu Leu Lys Val Asn Gln Glu Lys Val Asn Glu Cys Tyr Glu Leu Leu
        275                 280                 285

Leu Glu His Asn Pro Ser Lys Lys Arg Met Met Asn Leu Val Asp Gln
    290                 295                 300

Asp Ser Pro Ser Gly Val Leu Asp Phe Asp Asp Ser Ser Asn Ser Ser
305                 310                 315                 320
```

```
Trp Asn Val Ser Thr Thr Ala Ser Val Ser Ser Ser Ser Ser Pro
                325                 330                 335

Glu Pro Leu Leu Lys Arg Arg Val Gln Glu Gln Gln Met Arg Leu
                340                 345                 350

Pro Ser Ile Asn Arg Met Phe Leu Asp Val Leu Ser Ser Pro Arg
                355                 360                 365

<210> SEQ ID NO 10
<211> LENGTH: 361
<212> TYPE: PRT
<213> ORGANISM: Arabidopsis thaliana

<400> SEQUENCE: 10

Met Ala Leu Glu Glu Glu Glu Ser Gln Asn Ala Pro Phe Cys Val
1               5                   10                  15

Leu Asp Gly Leu Phe Cys Glu Glu Ser Glu Phe His Glu Gln Val
                20                  25                  30

Asp Leu Cys Asp Glu Ser Val Glu Lys Phe Pro Phe Leu Asn Leu Gly
                35                  40                  45

Leu Ser Asp His Asp Met Leu Trp Asp Asp Glu Leu Ser Thr Leu
                50                  55                  60

Ile Ser Lys Gln Glu Pro Cys Leu Tyr Asp Glu Ile Leu Asp Glu
65                  70                  75                  80

Phe Leu Val Leu Cys Arg Glu Lys Ala Leu Asp Trp Ile Phe Lys Val
                85                  90                  95

Lys Ser His Tyr Gly Phe Asn Ser Leu Thr Ala Leu Leu Ala Val Asn
                100                 105                 110

Tyr Phe Asp Arg Phe Ile Thr Ser Arg Lys Phe Gln Thr Asp Lys Pro
                115                 120                 125

Trp Met Ser Gln Leu Thr Ala Leu Ala Cys Leu Ser Leu Ala Ala Lys
                130                 135                 140

Val Glu Glu Ile Arg Val Pro Phe Leu Leu Asp Phe Gln Val Glu Glu
145                 150                 155                 160

Ala Arg Tyr Val Phe Glu Ala Lys Thr Ile Gln Arg Met Glu Leu Leu
                165                 170                 175

Val Leu Ser Thr Leu Asp Trp Arg Met His Pro Val Thr Pro Ile Ser
                180                 185                 190

Phe Phe Asp His Ile Ile Arg Arg Tyr Ser Phe Lys Ser His His Gln
                195                 200                 205

Leu Glu Phe Leu Ser Arg Cys Glu Ser Leu Leu Ser Ile Ile Pro
                210                 215                 220

Asp Ser Arg Phe Leu Ser Phe Ser Pro Ser Val Leu Ala Thr Ala Ile
225                 230                 235                 240

Met Val Ser Val Ile Arg Asp Leu Lys Met Cys Asp Glu Ala Val Tyr
                245                 250                 255

Gln Ser Gln Leu Met Thr Leu Leu Lys Val Asp Ser Glu Lys Val Asn
                260                 265                 270

Lys Cys Tyr Glu Leu Val Leu Asp His Ser Pro Ser Lys Lys Arg Met
                275                 280                 285

Met Asn Trp Met Gln Gln Pro Ala Ser Pro Ile Gly Val Phe Asp Ala
                290                 295                 300

Ser Phe Ser Ser Asp Ser Ser Asn Glu Ser Trp Val Val Ser Ala Ser
305                 310                 315                 320

Ala Ser Val Ser Ser Ser Pro Ser Ser Glu Pro Leu Leu Lys Arg Arg
                325                 330                 335
```

Arg Val Gln Glu Gln Gln Met Arg Leu Ser Ser Ile Asn Arg Met Phe
            340                 345                 350

Phe Asp Val Leu Ser Ser Ser Pro Arg
        355                 360

<210> SEQ ID NO 11
<211> LENGTH: 355
<212> TYPE: PRT
<213> ORGANISM: Euphorbia esula

<400> SEQUENCE: 11

Met Glu Asp Ser Thr Gln Ile Ser Leu Ile Phe Asp Gly Leu Tyr Cys
1               5                   10                  15

Glu Glu Gln Gly Ile Gly Glu Asp Phe Asp Asp Gly Asn Glu Asp Tyr
            20                  25                  30

Val Lys Lys Glu Leu Ser Leu Ser Ser Val Leu Leu Glu Gln Asp Leu
        35                  40                  45

Phe Trp Thr Asp Asp Glu Leu Leu Asn Leu Ile Ser Lys Glu Lys Glu
    50                  55                  60

Thr His Phe Ser Phe Gly Asp Phe Ser Ser His Gly Ser Leu Met Val
65                  70                  75                  80

Ala Arg Lys Glu Ala Ile Asp Trp Ile Leu Arg Val Lys Gly Phe Tyr
                85                  90                  95

Gly Phe Asn Ala Leu Ser Cys Val Leu Ala Val Asn Tyr Phe Asp Arg
            100                 105                 110

Phe Ile Ser Ser Leu Val Phe Thr Arg Asp Lys Pro Trp Met Gly Gln
        115                 120                 125

Leu Ala Ala Val Ala Cys Leu Ser Leu Ala Ala Lys Met Glu Glu Thr
    130                 135                 140

Gln Val Pro Leu Leu Leu Asp Leu Gln Val Glu Glu Ser Lys Tyr Val
145                 150                 155                 160

Phe Glu Ala Lys Thr Ile Lys Arg Met Glu Leu Leu Val Leu Ser Thr
                165                 170                 175

Leu Gln Trp Arg Met Asn Pro Val Thr Pro Ile Cys Tyr Phe Asp His
            180                 185                 190

Ile Ile Arg Arg Leu Gly Leu Lys Asn His Leu His Trp Glu Phe Leu
        195                 200                 205

Arg Arg Cys Glu Leu Leu Leu Ser Val Ile Ser Asp Ser Arg Phe
    210                 215                 220

Met Ser Tyr Ala Pro Ser Ile Leu Ala Thr Ser Ile Met Ile His Val
225                 230                 235                 240

Ile Lys Glu Val Asp Pro Phe Ser Gln Met Glu Tyr Gln Asn Gln Leu
                245                 250                 255

Leu Asp Val Ile Lys Ile Asn Lys Glu Glu Val Asn Gln Cys Tyr Lys
            260                 265                 270

Leu Ile Leu Glu Leu Ser Gly Lys Gln Asp Gln Gly Tyr Lys Arg Lys
        275                 280                 285

Tyr Pro Ser Arg Pro Gly Ser Pro Asn Gly Val Ile Asp Ala Tyr Phe
    290                 295                 300

Ser Gly Asp Ser Ser Asn Asp Ser Trp Gly Val Ser Ser Ser Ile Ser
305                 310                 315                 320

Ser Ser Pro Ser Ile Pro Arg Phe Lys Arg Ile Lys Ser Gln Asp Gln
                325                 330                 335

Gln Met Arg Leu Pro Ser Ile Asn Arg Met Phe Val Asp Val Leu Ser

```
                    340                 345                 350
Ser Pro His
        355

<210> SEQ ID NO 12
<211> LENGTH: 357
<212> TYPE: PRT
<213> ORGANISM: Helianthus tuberosus

<400> SEQUENCE: 12

Met Ala Ile Leu Ser Pro Tyr Ser Ser Phe Leu Asp Thr Leu Phe
1               5                   10                  15

Cys Asn Glu Gln Gln Asp His Glu Tyr His Glu Tyr Glu Tyr Glu Asp
                20                  25                  30

Glu Phe Thr Gln Thr Thr Leu Thr Asp Ser Ser Asp Leu His Leu Pro
            35                  40                  45

Pro Leu Asp Gln Leu Asp Leu Ser Trp Glu His Glu Glu Leu Val Ser
50                  55                  60

Leu Phe Thr Lys Glu Gln Glu Gln Gln Lys Gln Thr Pro Cys Thr Leu
65                  70                  75                  80

Ser Phe Gly Lys Thr Ser Pro Ser Val Phe Ala Ala Arg Lys Glu Ala
                85                  90                  95

Val Asp Trp Ile Leu Lys Val Lys Ser Cys Tyr Gly Phe Thr Pro Leu
                100                 105                 110

Thr Ala Ile Leu Ala Ile Asn Tyr Leu Asp Arg Phe Leu Ser Ser Leu
            115                 120                 125

His Phe Gln Glu Asp Lys Pro Trp Met Ile Gln Leu Val Ala Val Ser
        130                 135                 140

Cys Leu Ser Leu Ala Ala Lys Val Glu Glu Thr Gln Val Pro Leu Leu
145                 150                 155                 160

Leu Asp Leu Gln Val Glu Asp Thr Lys Tyr Leu Phe Glu Ala Lys Asn
                165                 170                 175

Ile Gln Lys Met Glu Leu Leu Val Met Ser Thr Leu Lys Trp Arg Met
                180                 185                 190

Asn Pro Val Thr Pro Ile Ser Phe Leu Asp His Ile Val Arg Arg Leu
            195                 200                 205

Gly Leu Thr Asp His Val His Trp Asp Phe Phe Lys Lys Cys Glu Ala
        210                 215                 220

Met Ile Leu Cys Leu Val Ser Asp Ser Arg Phe Val Cys Tyr Lys Pro
225                 230                 235                 240

Ser Val Leu Ala Thr Ala Thr Met Leu His Val Val Asp Glu Ile Asp
                245                 250                 255

Pro Pro Asn Cys Ile Asp Tyr Lys Ser Gln Leu Leu Asp Leu Leu Lys
                260                 265                 270

Thr Thr Lys Asp Asp Ile Asn Glu Cys Tyr Glu Leu Ile Val Glu Leu
            275                 280                 285

Ala Tyr Asp His His Asn Lys Arg Lys His Asp Ala Asn Glu Thr Thr
        290                 295                 300

Thr Asn Pro Val Ser Pro Ala Gly Val Ile Asp Phe Thr Cys Asp Glu
305                 310                 315                 320

Ser Ser Asn Glu Ser Trp Glu Leu Asn Ala His His Phe Arg Glu Pro
                325                 330                 335

Ser Phe Lys Lys Thr Arg Met Asp Ser Thr Ile Arg Val Arg Val Trp
            340                 345                 350
```

```
Phe Thr Tyr Lys Leu
        355

<210> SEQ ID NO 13
<211> LENGTH: 386
<212> TYPE: PRT
<213> ORGANISM: Medicago sativa

<400> SEQUENCE: 13

Met Ala Ile His His His His His Asn His Gln Gln Leu Gln Gln His
1               5                   10                  15

Thr Ser Ser Leu Phe Asp Ala Leu Tyr Cys Asp Glu Glu Glu Lys Trp
            20                  25                  30

Glu Asp Asp Asp Glu Gly Glu Val Val Asp Glu Gly Ala Gln Ser Asp
        35                  40                  45

Val Thr Thr Thr Asn Tyr Asp Ile Leu Asp Ser Thr Ser Leu Leu Pro
    50                  55                  60

Leu Leu Leu Leu Glu Gln Asn Leu Phe Asn Glu Asp Glu Glu Leu Asn
65                  70                  75                  80

Thr Leu Phe Ser Lys Glu Ile Thr Gln Gln Glu Thr Tyr Tyr Glu Asp
                85                  90                  95

Leu Lys Asn Val Ile Asn Phe Asp Ser Leu Ser Gln Pro Arg Arg Glu
            100                 105                 110

Ala Val Glu Trp Met Leu Lys Val Asn Ala His Tyr Gly Phe Ser Ala
        115                 120                 125

Leu Thr Ala Thr Leu Ala Val Asn Tyr Leu Asp Arg Phe Leu Leu Ser
    130                 135                 140

Phe His Phe Gln Lys Glu Lys Pro Trp Met Ile Gln Leu Val Ala Val
145                 150                 155                 160

Thr Cys Ile Ser Leu Ala Ala Lys Val Glu Glu Thr Gln Val Pro Leu
                165                 170                 175

Leu Leu Asp Leu Gln Val Gln Asp Thr Lys Tyr Val Phe Glu Ala Lys
            180                 185                 190

Thr Ile Gln Arg Met Glu Leu Leu Ile Leu Ser Thr Leu Lys Trp Lys
        195                 200                 205

Met His Pro Val Thr Thr His Ser Phe Leu Asp His Ile Ile Arg Arg
    210                 215                 220

Leu Gly Leu Lys Thr Asn Leu His Trp Glu Phe Leu Arg Arg Cys Glu
225                 230                 235                 240

Asn Leu Leu Leu Ser Val Leu Leu Asp Ser Arg Phe Val Gly Cys Val
                245                 250                 255

Pro Ser Val Leu Ala Thr Ala Thr Met Leu His Val Ile Asp Gln Ile
            260                 265                 270

Glu Gln Ser Asp Asp Asn Gly Val Asp Tyr Lys Asn Gln Leu Leu Asn
        275                 280                 285

Val Leu Lys Ile Ser Lys Glu Lys Val Asp Glu Cys Tyr Asn Ala Ile
    290                 295                 300

Leu His Leu Thr Asn Ala Asn Asn Tyr Gly His Lys Arg Lys Tyr Glu
305                 310                 315                 320

Glu Ile Pro Gly Ser Pro Ser Gly Val Ile Asp Ala Val Phe Ser Ser
                325                 330                 335

Asp Gly Ser Asn Asp Ser Trp Thr Val Gly Ala Ser Ser Tyr Ser Thr
            340                 345                 350

Ser Glu Pro Val Phe Lys Lys Thr Lys Asn Gln Gly Gln Asn Met Asn
        355                 360                 365
```

Leu Ser Pro Ile Asn Arg Val Ile Val Gly Ile Leu Ala Thr Ala Thr
        370                 375                 380

Ser Pro
385

<210> SEQ ID NO 14
<211> LENGTH: 373
<212> TYPE: PRT
<213> ORGANISM: Nicotiana tabacum

<400> SEQUENCE: 14

Met Ala Ile Glu His Asn Glu Gln Gln Glu Leu Ser Gln Ser Phe Leu
1               5                  10                  15

Leu Asp Ala Leu Tyr Cys Glu Glu Glu Glu Lys Trp Gly Asp Leu
            20                  25                  30

Val Asp Asp Glu Thr Ile Ile Thr Pro Leu Ser Ser Glu Val Thr Thr
        35                  40                  45

Thr Thr Thr Thr Thr Thr Lys Pro Asn Ser Leu Leu Pro Leu Leu Leu
    50                  55                  60

Leu Glu Gln Asp Leu Phe Trp Glu Asp Glu Leu Leu Ser Leu Phe
65                  70                  75                  80

Ser Lys Glu Lys Glu Thr His Cys Trp Phe Asn Ser Phe Gln Asp Asp
                85                  90                  95

Ser Leu Leu Cys Ser Ala Arg Val Asp Ser Val Glu Trp Ile Leu Lys
            100                 105                 110

Val Asn Gly Tyr Tyr Gly Phe Ser Ala Leu Thr Ala Val Leu Ala Ile
        115                 120                 125

Asn Tyr Phe Asp Arg Phe Leu Thr Ser Leu His Tyr Gln Lys Asp Lys
    130                 135                 140

Pro Trp Met Ile Gln Leu Ala Ala Val Thr Cys Leu Ser Leu Ala Ala
145                 150                 155                 160

Lys Val Glu Glu Thr Gln Val Pro Leu Leu Leu Asp Phe Gln Val Glu
                165                 170                 175

Asp Ala Lys Tyr Val Phe Glu Ala Lys Thr Ile Gln Arg Met Glu Leu
            180                 185                 190

Leu Val Leu Ser Ser Leu Lys Trp Arg Met Asn Pro Val Thr Pro Leu
        195                 200                 205

Ser Phe Leu Asp His Ile Ile Arg Arg Leu Gly Leu Arg Asn Asn Ile
    210                 215                 220

His Trp Glu Phe Leu Arg Arg Cys Glu Asn Leu Leu Ser Ile Met
225                 230                 235                 240

Ala Asp Cys Arg Phe Val Arg Tyr Met Pro Ser Val Leu Ala Thr Ala
                245                 250                 255

Ile Met Leu His Val Ile His Gln Val Glu Pro Cys Asn Ser Val Asp
            260                 265                 270

Tyr Gln Asn Gln Leu Leu Gly Val Leu Lys Ile Asn Lys Glu Lys Val
        275                 280                 285

Asn Asn Cys Phe Glu Leu Ile Ser Glu Val Cys Ser Lys Pro Ile Ser
    290                 295                 300

His Lys Arg Lys Tyr Glu Asn Pro Ser His Ser Pro Ser Gly Val Ile
305                 310                 315                 320

Asp Pro Ile Tyr Ser Ser Glu Ser Ser Asn Asp Ser Trp Asp Leu Glu
                325                 330                 335

Ser Thr Ser Ser Tyr Phe Pro Val Phe Lys Lys Ser Arg Val Gln Glu

```
            340                 345                 350
Gln Gln Met Lys Leu Ala Ser Ser Ile Ser Arg Val Phe Val Glu Ala
        355                 360                 365

Val Gly Ser Pro His
        370

<210> SEQ ID NO 15
<211> LENGTH: 368
<212> TYPE: PRT
<213> ORGANISM: Nicotiana tabacum

<400> SEQUENCE: 15

Met Gly Ile Gln His Asn Glu His Asn Gln Asp Gln Thr Gln Ser Phe
1               5                   10                  15

Leu Leu Asp Ala Leu Tyr Cys Glu Glu Arg Trp Glu Glu Thr Ile
            20                  25                  30

Glu Asp Glu Ile Leu Glu Lys Glu Ala Thr Leu Pro Leu Pro Leu Pro
        35                  40                  45

Leu Leu Glu Gln Asp Leu Phe Trp Glu Asp Glu Leu Leu Ser Leu
    50                  55                  60

Phe Thr Lys Glu Lys Glu Thr Ile Ser Asn Phe Glu Thr Ile Lys Thr
65                  70                  75                  80

Asp Pro Leu Leu Cys Leu Ser Arg Lys Glu Ala Val Lys Trp Ile Leu
                85                  90                  95

Lys Val Asn Ala His Tyr Gly Phe Ser Thr Phe Thr Ala Ile Leu Ala
            100                 105                 110

Ile Asn Tyr Phe Asp Arg Phe Leu Ser Ser Leu His Phe Gln Lys Asp
        115                 120                 125

Lys Pro Trp Met Ile Gln Leu Val Ala Val Thr Cys Leu Ser Leu Ala
    130                 135                 140

Ala Lys Val Glu Glu Thr Gln Val Pro Leu Leu Leu Asp Phe Gln Val
145                 150                 155                 160

Glu Asp Ala Lys Tyr Val Phe Glu Ala Lys Thr Ile Gln Arg Met Glu
                165                 170                 175

Leu Leu Val Leu Ser Ser Leu Lys Trp Arg Met Asn Pro Val Thr Pro
            180                 185                 190

Leu Ser Phe Val Asp His Ile Ile Arg Arg Leu Gly Leu Lys Ser His
        195                 200                 205

Ile His Trp Glu Phe Leu Lys Gln Cys Glu Arg Ile Leu Leu Leu Val
    210                 215                 220

Ile Ala Asp Cys Arg Phe Leu Ser Tyr Met Pro Ser Val Leu Ala Thr
225                 230                 235                 240

Ala Thr Met Leu His Val Ile His Gln Val Glu Pro Cys Asn Ala Ala
                245                 250                 255

Asp Tyr Gln Asn Gln Leu Leu Glu Val Leu Asn Ile Ser Lys Glu Lys
            260                 265                 270

Val Asn Asp Cys Tyr Glu Leu Ile Thr Glu Val Ser Tyr Asn Ser Ile
        275                 280                 285

Ser His Lys Arg Lys Tyr Glu Ser Pro Ile Asn Ser Pro Ser Ala Val
    290                 295                 300

Ile Asp Thr Phe Tyr Ser Ser Glu Asn Ser Asn Glu Ser Trp Asp Leu
305                 310                 315                 320

Gln Thr Ser Ser Ser Ile Pro Ser Thr Tyr Ser Pro Arg Asp Gln Phe
                325                 330                 335
```

```
Leu Pro Leu Phe Lys Lys Ser Arg Val Gln Glu Gln Met Arg Leu
            340                 345                 350

Thr Ser Leu Ser Arg Val Phe Val Asp Tyr Ala Val Gly Ser Pro Arg
            355                 360                 365

<210> SEQ ID NO 16
<211> LENGTH: 384
<212> TYPE: PRT
<213> ORGANISM: Pisum sativum

<400> SEQUENCE: 16

Met Ala Ile His His His His His His Gln Gln Leu His His Asn
1                 5                  10                  15

Ser Leu Leu Asp Ala Leu Tyr Cys Asp Glu Glu Lys Leu Glu Glu
                20                  25                  30

Gln Glu Asp Val Ser Ser Gln Gln Ser Asp Val Thr Thr Asn Asn Asp
                35                  40                  45

Asn Asn Ile Leu Asp Ser Thr Ser Leu Phe Pro Leu Leu Leu Leu Glu
50                  55                  60

Gln Asn Leu Phe Ser Gln Asp Glu Glu Leu Thr Thr Leu Phe Ser Lys
65                  70                  75                  80

Glu Lys Thr Gln Gln Glu Thr Tyr Tyr Glu Asp Leu Lys Asn Val Val
                85                  90                  95

Asp Phe Val Ser Leu Ser Gln Pro Arg Arg Glu Ala Val Gln Trp Met
                100                 105                 110

Leu Lys Val Asn Ala His Tyr Ala Phe Ser Pro Leu Thr Ala Thr Leu
                115                 120                 125

Ala Val Thr Tyr Phe Asp Arg Phe Leu Leu Thr Phe His Phe Gln Lys
                130                 135                 140

Asp Lys Pro Trp Met Ile Gln Leu Val Ala Val Thr Cys Ile Ser Leu
145                 150                 155                 160

Ala Ala Lys Val Glu Glu Thr Gln Val Pro Leu Leu Leu Asp Leu Gln
                165                 170                 175

Val Gln Asp Thr Lys Tyr Val Phe Glu Ala Lys Thr Ile Gln Arg Met
                180                 185                 190

Glu Leu Leu Ile Leu Ser Thr Leu Lys Trp Lys Met His Pro Val Thr
                195                 200                 205

Pro His Ser Phe Leu Asp His Ile Ile Thr Arg Leu Gly Leu Lys Thr
                210                 215                 220

Asn Leu His Trp Glu Phe Leu Arg Arg Cys Glu Asn Leu Leu Leu Ser
225                 230                 235                 240

Val Leu Leu Asp Ser Arg Phe Val Gly Cys Val Pro Ser Val Leu Ala
                245                 250                 255

Thr Ala Thr Met Leu His Val Ile Asp Gln Ile Glu Glu Ser Asp Asp
                260                 265                 270

Asn Gly Val Asp Tyr Lys Asn Gln Leu Leu Ser Ile Leu Lys Ile Asn
                275                 280                 285

Lys Glu Lys Val Asp Glu Cys Tyr Asn Ala Ile Val Glu Val Thr Asn
                290                 295                 300

Glu Asn Asn Tyr Gly His Lys Arg Lys Tyr Glu Gln Ile Pro Gly Ser
305                 310                 315                 320

Pro Ser Gly Val Ile Asp Ala Val Phe Ser Asp Gly Ser Asn Asp
                325                 330                 335

Ser Trp Lys Val Gly Ser Ser Ser Tyr Ser Thr Ser Glu Pro Val Phe
                340                 345                 350
```

```
Lys Lys Thr Lys Thr Gln Gly Gln Asn Arg Asn Leu Ser Pro Leu Asn
        355                 360                 365

Arg Val Ile Val Gly Ile Leu Ala Thr Ala Ser Ala Thr Thr Ser Pro
        370                 375                 380
```

<210> SEQ ID NO 17
<211> LENGTH: 371
<212> TYPE: PRT
<213> ORGANISM: Populus alba

<400> SEQUENCE: 17

```
Met Ser Phe Leu Gln Gln Glu Thr His Asn Gln Ser Pro Ala Leu
 1               5                  10                  15

Ala Leu Asp Gly Leu Tyr Cys Glu Glu Asp Gly Phe Gly Glu Asp Tyr
                20                  25                  30

Ser Cys Gly Leu Asp Asp Glu Thr Ser Gln Val Tyr Asp Gln Asn Val
            35                  40                  45

Lys Lys Glu Gln Asn Leu Ser Ser Val Leu Leu Glu Gln Asp Leu Phe
        50                  55                  60

Trp Glu Asp Ser Glu Leu Leu Ser Leu Ile Ser Lys Glu Lys Glu Thr
 65                  70                  75                  80

His Val Val Phe Asp Ser Val Gly Ser Arg Asp Gly Ser Leu Met Val
                85                  90                  95

Val Arg Arg Glu Ala Val Glu Trp Phe Leu Arg Val Lys Ala His Tyr
                100                 105                 110

Gly Phe Ser Ala Leu Thr Gly Val Leu Ala Val Asn Tyr Phe Asp Arg
            115                 120                 125

Phe Ile Ser Ser Arg Phe Arg Arg Asp Lys Pro Trp Met Gly Gln
        130                 135                 140

Leu Ala Ala Val Ala Cys Leu Ser Leu Ala Ala Lys Val Glu Glu Thr
145                 150                 155                 160

Gln Val Pro Leu Leu Leu Asp Leu Gln Val Glu Asp Ala Lys Tyr Val
                165                 170                 175

Phe Glu Ala Lys Thr Ile Lys Arg Met Glu Leu Trp Val Leu Ser Thr
                180                 185                 190

Leu His Trp Arg Met Asn Pro Val Thr Ser Ile Ser Phe Phe Asp His
            195                 200                 205

Ile Ile Arg Arg Leu Gly Leu Lys Thr His Met His Trp Glu Phe Leu
        210                 215                 220

Trp Arg Cys Glu Arg Leu Leu Leu Ser Val Ile Ser Asp Ser Arg Phe
225                 230                 235                 240

Met Ser Tyr Leu Pro Ser Ile Leu Ala Thr Ala Thr Met Leu His Val
                245                 250                 255

Ile Lys Glu Val Glu Pro Arg Asn Gln Leu Gln Tyr Gln Thr Gln Leu
                260                 265                 270

Met Ala Val Leu Lys Thr Asn Glu Asp Glu Val Asn Glu Cys Tyr Arg
            275                 280                 285

Leu Ile Leu Glu Gln Pro Gly Ser Gln Asn Gln Arg His Lys Arg Lys
        290                 295                 300

Tyr Leu Ser Thr Pro Ser Ser Pro Asn Gly Val Ile Asp Ala Ser Phe
305                 310                 315                 320

Ser Ser Glu Asn Ser Asn Asp Ser Trp Ala Val Ala Ser Ser Ile Ser
                325                 330                 335

Ser Ser Ser Ser Val Pro Gln Phe Lys Arg Ser Arg Ala Gln Val Gln
```

```
                    340                 345                 350
Gln Met Arg Leu Pro Ser Leu Asn Arg Met Cys Val Asp Val Leu Ser
                355                 360                 365
Ser Pro His
        370

<210> SEQ ID NO 18
<211> LENGTH: 343
<212> TYPE: PRT
<213> ORGANISM: Chenopodium rubrum

<400> SEQUENCE: 18

Met Thr Thr Leu Glu Thr Glu Gln Glu Gln Pro Phe Ser Gln Asn
1               5                   10                  15

Ser Pro Leu Phe Leu Asp Cys Leu Tyr Cys Glu Lys Tyr Trp Asp
                20                  25                  30

Tyr Asp Tyr His Asp Glu Asp Phe Gly Ser Leu Asn Ser Ser Lys
                35                  40                  45

Leu His Asp Cys Ser Leu Ile Cys Cys Glu Asp Asp Glu Glu Ile Gln
50                  55                  60

Leu Asn Ala Leu Val Ser Lys Glu Glu Lys Ile Asn Phe Asp Glu Gly
65                  70                  75                  80

Asp Leu Gly Gly Asn Gln Leu Val Met Glu Thr Arg Arg Glu Ala Leu
                85                  90                  95

Glu Trp Met Ile Arg Val Asn Tyr His His Asn Phe Ser Val Ile Thr
                100                 105                 110

Leu Val Leu Gly Val Asn Tyr Phe Asp Arg Phe Met Leu Ser Phe Gly
                115                 120                 125

Phe Gln Lys Glu Met Pro Trp Met Thr His Leu Ala Ala Val Ala Cys
                130                 135                 140

Leu Ser Leu Ala Ser Lys Val Glu Glu Thr His Val Pro Leu Leu Leu
145                 150                 155                 160

Asp Phe Gln Val Glu His Glu Gln Ile Phe Glu Ala Lys Val Val Gln
                165                 170                 175

Arg Met Glu Leu Leu Val Leu Gln His Ser Asn Gly Lys Met Asn Ala
                180                 185                 190

Val Thr Pro Leu Ser Tyr Phe Gly His Leu Ile Arg Lys Leu Lys Leu
                195                 200                 205

Lys Pro His Phe His Cys Lys Ile Leu Thr Arg Cys Glu Asn Ile Ile
                210                 215                 220

Val Ser Val Ile Leu Asp Pro Arg Phe Leu Cys Tyr Val Pro Ser Val
225                 230                 235                 240

Leu Ala Ala Ala Ser Met Val Gln Thr Leu Lys Glu Ile Gly Leu Trp
                245                 250                 255

Ser Ile Leu Glu His Gln Asn Asp Ile Met Asn Thr Leu Lys Leu Asp
                260                 265                 270

Lys Val Lys Val Glu Asp Cys Tyr Asn Phe Ile Gln Glu Val Ser Ser
                275                 280                 285

Asn Glu Lys Ala Arg Lys Arg Lys Trp Tyr Asn Asn Ile Ser Ser Ala
                290                 295                 300

Asn Arg Asn Pro Asn Asn Val Leu Glu Leu Val Val Ser Ser Glu Ser
305                 310                 315                 320

Ser Asn Asn Asp Leu Pro Ser Glu Thr Leu Pro Lys Lys Cys Arg Thr
                325                 330                 335
```

Met Gly Pro Pro Cys Phe Gly
            340

<210> SEQ ID NO 19
<211> LENGTH: 350
<212> TYPE: PRT
<213> ORGANISM: Euphorbia esula

<400> SEQUENCE: 19

Met Ala Asn His Ser Pro Leu Phe Leu Tyr Asp Ala Leu Tyr Cys Ser
1               5                   10                  15

Glu Glu Asp Asn Trp Glu Gly Val Val Asp Ile Phe His Glu Gln
            20                  25                  30

Glu Asp Gln Gly Glu Asn Thr Ser Val Phe Pro Gln Asn Ser Ser Pro
        35                  40                  45

Val Asp Leu Asn Trp Glu Glu Asp Glu Leu Thr Ser Val Phe Ser Lys
    50                  55                  60

Gln Glu Gln Asn Gln Leu Tyr Lys Lys Leu Glu Ile Asn Pro Cys Leu
65                  70                  75                  80

Ala Lys Ser Arg Arg Asp Ala Val Asp Trp Met Met Lys Val Asn Ala
                85                  90                  95

His Tyr Ser Phe Thr Ala Leu Thr Ser Val Leu Ala Val Asn Phe Leu
            100                 105                 110

Asp Arg Phe Leu Phe Ser Phe Asp Leu Gln Thr Glu Lys Pro Trp Met
        115                 120                 125

Thr Gln Leu Thr Ala Val Ala Cys Leu Ser Leu Ala Ala Lys Val Glu
    130                 135                 140

Glu Thr Gln Val Pro Leu Leu Leu Asp Leu Gln Val Val Asp Ser Lys
145                 150                 155                 160

Tyr Val Phe Glu Ala Lys Thr Ile Gln Arg Met Glu Leu Leu Val Leu
                165                 170                 175

Ser Thr Leu Gln Trp Arg Met Asn Pro Val Thr Pro Leu Ser Phe Ile
            180                 185                 190

Asp Tyr Met Thr Arg Arg Leu Gly Phe Lys Asp Tyr Leu Cys Trp Glu
        195                 200                 205

Phe Ile Arg Arg Cys Glu Leu Ile Val Leu Ser Ile Ile Ser Asp Met
    210                 215                 220

Arg Phe Ile Pro Tyr Leu Pro Ser Glu Ile Ala Ser Ala Ile Met Leu
225                 230                 235                 240

His Val Ile Asn Gly Ile Glu Pro Ser Leu Gly Asp Glu Phe Glu Thr
                245                 250                 255

Gln Leu Phe Gly Ile Leu Gly Ile Asp Lys Glu Lys Val Asn Asn Cys
            260                 265                 270

Arg Glu Met Ile Ile Glu Leu Gly Ser Arg Tyr Tyr Gly Asn Gln Ser
        275                 280                 285

Asn Lys Arg Lys Tyr Gly Ser Asp Pro Gly Ser Pro Asn Cys Val Met
    290                 295                 300

Asp Val Ser Phe Ser Ser Asp Asn Ser Asn Asp Ser Trp Ala Val Gly
305                 310                 315                 320

Ser Lys Ser Ser Ser Val Ser Ser Ser Pro Ala Ala Lys Lys Leu Arg
                325                 330                 335

Ala Val Ser Gly Met Asn His Glu Asn Ala Ile Ile Leu Ser
            340                 345                 350

<210> SEQ ID NO 20

```
<211> LENGTH: 308
<212> TYPE: PRT
<213> ORGANISM: Helianthus annuus

<400> SEQUENCE: 20

Met Ala Ile Leu Ser Arg Tyr Ser Ser Asn Thr Leu Phe Cys Ile
1               5                   10                  15

Glu Glu Gln Val His Glu Asp Glu Glu Leu Thr His Gln Asp Ser
                20                  25                  30

Ser Ala Ile His Pro Leu Asp Leu Gln Asp Leu Cys Trp Glu His Glu
        35                  40                  45

Glu Leu Val Ser Leu Phe Thr Lys Glu Glu Gln Gln Lys Gln Thr
    50                  55                  60

Pro Trp Pro Ser Ser Cys Thr Leu Ser Phe Arg Lys Glu Ala Val Asp
65                  70                  75                  80

Trp Ile Leu Lys Val Lys Gly Cys His Gly Phe Thr Pro Leu Thr Ala
                85                  90                  95

Ile Leu Ala Ile Asn Tyr Leu Asp Arg Phe Leu Ser Ser Leu His Phe
                100                 105                 110

Gln Lys Ala Asn Thr Pro Trp Met Ile His Leu Ala Val Thr Cys
        115                 120                 125

Leu Ser Leu Ala Ala Lys Ile Gln Glu Thr His Val Pro Leu Leu
130                 135                 140

Asp Leu Gln Leu Glu Glu Ser Lys Phe Leu Phe Glu Ala Lys Asn Ile
145                 150                 155                 160

Gln Lys Thr Glu Leu Leu Val Met Ser Thr Leu Lys Trp Arg Met Asn
                165                 170                 175

Leu Val Thr Pro Ile Ser Phe Leu Asp His Ile Val Arg Arg Leu Gly
                180                 185                 190

Leu Ser Asn His Leu His Trp Asp Phe Phe Lys Lys Cys Glu Ala Met
        195                 200                 205

Ile Leu Tyr Leu Val Ala Asp Ser Arg Phe Val Cys Tyr Lys Pro Ser
210                 215                 220

Val Leu Ala Thr Ala Thr Met Leu Cys Val Val Glu Glu Ile Asp Pro
225                 230                 235                 240

Thr Asn Ser Ile Gly Tyr Lys Ser Gln Leu Leu Asp Leu Leu Lys Thr
                245                 250                 255

Thr Lys Asp His Ile Asn Glu Cys Tyr Lys Leu Val Met Asp Leu Ser
                260                 265                 270

Tyr Asp Asn His Asn Lys Gly Lys Arg Asp Glu Asn Glu Arg Thr Ile
        275                 280                 285

Tyr Pro Val Ser Pro Ala Gly Phe Ile Gly Phe Met Cys His Glu Ser
    290                 295                 300

Ser Asn Asp Ser
305

<210> SEQ ID NO 21
<211> LENGTH: 352
<212> TYPE: PRT
<213> ORGANISM: Lagenaria siceraria

<400> SEQUENCE: 21

Met Val Pro Pro Tyr Ala Leu Asp Ser Leu Tyr Cys Ser Glu Asp His
1               5                   10                  15

Trp Glu Asn Asp Asp Glu Glu Glu Glu Arg Gly Phe His Glu Gln Pro
                20                  25                  30
```

Tyr Ser Asn Leu Thr Thr Glu Ser Ser Pro Ile Leu Ala Val Ala
            35                  40                  45

Glu Gln Asp Leu Phe Trp Glu Asn Asp Glu Leu Ile Ser Leu Phe Ser
 50                  55                  60

Arg Glu Lys Pro Asn Glu Leu Phe Lys Thr Ile Gln Ile Asp Pro Ser
 65                  70                  75                  80

Leu Ala Ala Ala Arg Arg Ser Ala Val Gly Trp Met Leu Lys Val Asn
                 85                  90                  95

Ala His Tyr Ser Phe Ser Ala Leu Thr Ala Val Leu Ala Val Asp Tyr
                100                 105                 110

Leu Asp Arg Phe Leu Ser Cys Phe His Phe Gln Arg Asp Lys Pro Trp
            115                 120                 125

Met Ser Gln Leu Ala Ala Val Ala Cys Ile Ser Leu Ala Ala Lys Val
            130                 135                 140

Glu Glu Thr Gln Val Pro Leu Leu Leu Asp Leu Gln Val Glu Asp Ser
145                 150                 155                 160

Arg Tyr Leu Phe Glu Ala Lys Thr Ile Lys Lys Met Glu Leu Leu Val
                165                 170                 175

Leu Ser Thr Leu Gln Trp Arg Met Asn Pro Val Thr Pro Phe Ser Phe
            180                 185                 190

Val Asp Tyr Ile Ser Arg Arg Leu Gly Phe Lys Glu His Ile Cys Trp
            195                 200                 205

Glu Ile Leu Trp Gln Cys Glu Arg Thr Ile Leu Ser Val Ile Leu Glu
210                 215                 220

Ser Asp Phe Met Ser Phe Leu Pro Ser Val Met Ala Thr Ala Thr Met
225                 230                 235                 240

Leu His Val Phe Lys Ala Met Glu Glu Pro Thr Leu Ser Val Glu Tyr
                245                 250                 255

Asp Ser Gln Leu Leu Asn Ile Leu Gly Ile Asp Lys Gly Asn Val Glu
            260                 265                 270

Glu Cys Cys Lys Leu Ile Ser Asn Ala Ser Arg Arg Asn Gly Asn Gln
            275                 280                 285

Phe Lys Lys Arg Lys Ile Gly Ser Ile Pro Gly Ser Pro Asn Gly Val
            290                 295                 300

Met Asp Val Ser Phe Ser Ser Asp Ser Asn Asp Ser Trp Ser Val
305                 310                 315                 320

Ala Ser Ser Val Ser Ser Ser Pro Glu Pro Leu Thr Lys Lys Asn Arg
                325                 330                 335

Ala Asn Gly Ser Met Ser Gly Asp Cys Glu Thr Phe Arg Thr Leu Ser
            340                 345                 350

<210> SEQ ID NO 22
<211> LENGTH: 380
<212> TYPE: PRT
<213> ORGANISM: Lagenaria siceraria

<400> SEQUENCE: 22

Met Lys Lys Met Ala Leu His Ser Asn Lys His Arg Thr Gln Arg Leu
1               5                   10                  15

His Asn Ser Leu Phe Phe Phe Asp Phe Leu His Cys Thr Glu Gln Gln
            20                  25                  30

His Leu Gln Thr Glu His Pro Ile Phe Leu Asn Asn Gly Gly Thr Asn
            35                  40                  45

Asp Phe Pro Leu Phe Gln Gln Thr Thr Thr His Phe Leu Val Tyr Glu

```
                50                  55                  60
Asp Glu Glu Leu Asn His Leu Leu Ser Lys Glu Lys Asp Gln Asn Leu
 65                  70                  75                  80

Gln Thr Gly Ala Val Leu Lys Thr Leu Val Gln Thr Asp Asn Ala Leu
                 85                  90                  95

Ser Leu Ala Arg Thr Glu Ala Ile Asp Trp Leu Leu Lys Val Asn Ala
                100                 105                 110

Phe Tyr Gly Phe Ser Ser Leu Thr Ala Leu Leu Ala Ile Asn Tyr Leu
                115                 120                 125

Asp Arg Ile Leu Ser Gly Pro Tyr Phe Gln Arg Asp Lys Pro Trp Met
130                 135                 140

Leu Gln Leu Ala Ala Val Thr Cys Ile Ser Leu Ala Ala Lys Val Glu
145                 150                 155                 160

Glu Ile Arg Val Pro Leu Leu Leu Asp Leu Gln Val Glu Asp Ser Lys
                165                 170                 175

Tyr Ile Phe Glu Ala Lys Thr Ile Gln Arg Met Glu Leu Leu Val Leu
                180                 185                 190

Thr Ala Leu Gln Trp Lys Met His Pro Val Ala Pro Val Ser Phe Leu
                195                 200                 205

Gly Ile Ile Thr Lys Gly Leu Gly Met Lys Asn Gln Tyr Ile Gln Arg
210                 215                 220

Glu Phe Leu Arg Arg Cys Glu Arg Ile Leu Leu Ser Leu Val Ser Asp
225                 230                 235                 240

Ser Arg Ser Val Gly Ile Leu Pro Ser Ile Met Ala Val Ser Ala Met
                245                 250                 255

Val Ser Val Val Glu Glu Met Gly Asn Cys Asn Pro Leu Glu Glu Phe
                260                 265                 270

Gln Asp Gln Leu Leu Asn Ala Leu Lys Ile Asn Lys Gly Arg Val Lys
                275                 280                 285

Glu Cys Cys Lys Val Ile Met Glu Ala Lys Ile Lys Gly Ser Gly Lys
290                 295                 300

Arg Lys His Val Glu Glu Glu Ala Glu Ala Glu Ser Glu Ser
305                 310                 315                 320

Ser Glu Ala Glu Thr Glu Gly Glu Ala Glu Ala Glu Ala Gly Ser Pro
                325                 330                 335

Asn Gly Val Met Glu Ala Asn Phe Ser Cys Glu Ser Ser Asn Asp Ser
                340                 345                 350

Trp Glu Met Gly Thr Ile Val Ser Glu Tyr Thr His Phe Ser Ser Ser
                355                 360                 365

Ser Ser Ser Ser Lys Arg Ile Arg Pro Thr Arg
370                 375                 380

<210> SEQ ID NO 23
<211> LENGTH: 359
<212> TYPE: PRT
<213> ORGANISM: Lycopersicum esculentum

<400> SEQUENCE: 23

Met Val Phe Pro Leu Asp Ser Gln Leu Gln Asn Pro Ile Ser Ala Leu
 1               5                  10                  15

Leu Asp Gly Leu Tyr Cys Glu Glu Asp Arg Phe Leu Asp Asp Asp Leu
                20                  25                  30

Gly Glu Trp Ser Ser Leu Asp Val Gly Asn Glu Asn Val Lys Lys Thr
                35                  40                  45
```

```
Leu Pro Leu Leu Glu Cys Asp Met Phe Trp Glu His Asp Glu Leu Ala
 50                  55                  60

Thr Leu Leu Ser Lys Glu Asn Glu Phe His Leu Gly Phe Gln Ser Leu
 65                  70                  75                  80

Ile Ser Asp Gly Ser Leu Met Gly Ala Arg Lys Glu Ala Leu Asp Trp
                 85                  90                  95

Met Leu Arg Val Ile Ala Tyr Tyr Gly Phe Thr Ala Thr Thr Ala Val
            100                 105                 110

Leu Ala Val Asn Tyr Phe Asp Arg Phe Val Ser Gly Trp Cys Phe Gln
            115                 120                 125

Lys Asp Lys Pro Trp Met Ser Gln Leu Ala Ala Val Ala Cys Leu Ser
130                 135                 140

Ile Ala Ala Lys Val Glu Glu Thr Gln Val Pro Leu Leu Leu Asp Leu
145                 150                 155                 160

Gln Val Ala Asp Ser Arg Phe Val Phe Glu Ala Lys Thr Ile Gln Arg
                165                 170                 175

Met Glu Leu Leu Val Leu Ser Thr Leu Lys Trp Lys Met Asn Leu Val
            180                 185                 190

Thr Pro Leu Ser Phe Ile Asp His Ile Met Arg Arg Phe Gly Phe Met
            195                 200                 205

Ser Asn Leu His Met Asp Phe Leu Lys Lys Cys Glu Arg Leu Ile Leu
210                 215                 220

Asp Ile Ile Thr Asp Ser Arg Leu Leu His Tyr Pro Pro Ser Val Ile
225                 230                 235                 240

Ala Thr Ala Ser Met Phe Tyr Val Ile Asn Asp Ile Glu Pro Ser Asn
                245                 250                 255

Ala Met Glu Tyr Gln Asn Gln Leu Met Ser Val Leu Lys Val Arg Lys
            260                 265                 270

Asp Ile Phe Glu Glu Cys His Asp Leu Ile Leu Glu Leu Met Asp Thr
275                 280                 285

Ala Cys Tyr Lys Leu Cys Gln Ser Leu Lys Arg Lys His His Ser Val
290                 295                 300

Pro Gly Ser Pro Ser Gly Val Ile Asp Ala Tyr Phe Ser Ser Glu Ser
305                 310                 315                 320

Ser Asn Glu Ser Trp Ser Val Ala Ser Ser Ile Ser Ser Ser Pro Glu
                325                 330                 335

Pro Gln Tyr Lys Arg Asn Lys Thr Gln Asp Gln Arg Met Thr Leu Ala
            340                 345                 350

Pro Leu Gly Ser Asn Leu His
            355

<210> SEQ ID NO 24
<211> LENGTH: 364
<212> TYPE: PRT
<213> ORGANISM: Lycopersicum esculentum

<400> SEQUENCE: 24

Met Ala Ile Glu Asn Asn Asp Gln Ser Phe Phe Leu Asp Val Leu Tyr
  1               5                  10                  15

Cys Glu Glu Glu Glu Lys Trp Gly Asp Leu Leu Glu Asp Glu Glu
             20                  25                  30

Gly Val Ile Ile Asn Pro Leu Leu Ser Ser Glu Gly Thr Thr Lys
             35                  40                  45

Thr Asn Ser Leu Leu Leu Leu Pro Leu Leu Leu Glu Gln Asp Leu
 50                  55                  60
```

```
Phe Trp Glu Asp Glu Leu Leu Ser Leu Phe Val Lys Lys Glu
 65                  70                  75                  80

Thr Arg Cys Cys Phe Glu Ser Phe Gly Ser Asp Pro Phe Leu Cys Ser
                85                  90                  95

Ala Arg Val Asp Val Val Glu Trp Ile Leu Lys Val Asn Ala His Tyr
            100                 105                 110

Asp Phe Ser Ala Leu Thr Ala Ile Leu Ala Ile Asn Tyr Leu Asp Arg
                115                 120                 125

Phe Leu Ser Ser Leu Gln Phe Gln Lys Asp Lys Pro Trp Met Thr Gln
    130                 135                 140

Leu Ala Ala Val Thr Cys Leu Ser Leu Ala Ala Lys Val Glu Glu Thr
145                 150                 155                 160

Gln Val Pro Leu Leu Leu Asp Phe Gln Val Glu Asp Ala Lys Tyr Val
                165                 170                 175

Phe Glu Ala Lys Thr Ile Gln Arg Met Glu Leu Leu Val Leu Ser Ser
            180                 185                 190

Leu Lys Trp Arg Met Asn Pro Val Thr Pro Leu Ser Phe Leu Asp His
        195                 200                 205

Ile Ile Arg Arg Leu Gly Leu Lys Asn Asn Val His Trp Glu Phe Leu
210                 215                 220

Arg Arg Cys Glu Ser Leu Leu Leu Ser Val Met Ile Asp Cys Arg Phe
225                 230                 235                 240

Val Arg Tyr Met Pro Ser Val Leu Ala Thr Ala Ile Met Leu His Val
                245                 250                 255

Ile His Gln Ile Glu Pro Cys Asn Ala Ile Asp Tyr Gln Asn Gln Leu
            260                 265                 270

Leu Gly Val Leu Lys Ile Ser Lys Glu Asn Val Asn Asn Cys Tyr Glu
        275                 280                 285

Leu Ile Ser Glu Val Ser Ser Lys Pro Ile Thr Ser His Lys Arg Lys
290                 295                 300

Tyr Asp Glu Asn Pro Ser Ser Pro Ser Gly Val Ile Asp Pro Ile Tyr
305                 310                 315                 320

Thr Ser Glu Ser Ser Asn Asp Ser Trp Asp Leu Asp Leu Pro Ser Phe
                325                 330                 335

Lys Lys Ser Lys Val Gln Glu Gln Gln Met Lys Met Ser Ser Ser Leu
            340                 345                 350

Ser Arg Val Phe Val Glu Ala Val Gly Ser Pro His
        355                 360

<210> SEQ ID NO 25
<211> LENGTH: 336
<212> TYPE: PRT
<213> ORGANISM: Lycopersicum esculentum

<400> SEQUENCE: 25

Met Ser His His Tyr Gln Glu Gln Gln Leu Glu Ala Gln Lys Ile
 1               5                  10                  15

Pro Phe Leu Leu Asp Ser Leu Tyr Cys Glu Glu Asn Asn Ile Leu Thr
                20                  25                  30

Glu Val Ser Ile Glu Thr Glu Ser Phe Ser Ser His Asp Leu Leu Trp
            35                  40                  45

Glu Glu Glu Glu Leu Thr Ser Leu Phe Ser Lys Glu Thr Glu Tyr Glu
        50                  55                  60

Ile Ser Tyr Asn Val Leu Glu Lys Asn Gln Ser Phe Ile Ser Ser Arg
```

```
                65                  70                  75                  80
Arg Glu Ser Val Glu Trp Ile Leu Lys Thr Thr Ala Tyr Tyr Ser Phe
                    85                  90                  95

Ser Ala Gln Thr Gly Phe Leu Ala Val Asn Tyr Phe Asp Arg Phe Leu
                100                 105                 110

Leu Phe Ser Phe Asn Gln Ser Leu Asn His Lys Pro Trp Met Asn Gln
            115                 120                 125

Leu Val Ala Val Thr Cys Leu Ser Leu Ala Ala Lys Val Glu Glu Thr
        130                 135                 140

Asp Val Pro Leu Leu Asp Leu Gln Val Glu Glu Ser Gly Phe Leu
145                 150                 155                 160

Phe Glu Ser Lys Thr Ile Gln Arg Met Glu Met Leu Ile Leu Ser Thr
                165                 170                 175

Leu Lys Trp Lys Met Asn Pro Val Thr Pro Phe Ser Phe Leu Asp Phe
                180                 185                 190

Ile Thr Arg Arg Leu Gly Leu Lys His Cys Leu Ser Leu Glu Phe Leu
            195                 200                 205

Arg Arg Cys Glu Lys Val Leu Leu Tyr Thr Ile Thr Asp Asp Arg Phe
        210                 215                 220

Ile Gly Tyr Leu Pro Ser Ala Met Ala Ser Ala Thr Met Leu His Val
225                 230                 235                 240

Leu Asp Arg Leu Lys Pro Cys Ile Gly Glu Lys Tyr Gln Asp Gln Leu
                245                 250                 255

Leu Gly Ile Leu Gly Ile Val Lys Glu Lys Val Glu Gly Cys Tyr Arg
            260                 265                 270

Leu Ile Gln Glu Val Ala Cys Asn Ile Asp Phe Gly Ser Asn Lys Arg
        275                 280                 285

Lys Phe Gly Thr Leu Pro Gly Ser Pro Thr Gly Val Met Asp Met Ser
    290                 295                 300

Phe Ser Ser Asp Tyr Ser Asn Asp Ser Trp Ser Val Ala Thr Ser Val
305                 310                 315                 320

Thr Ser Ser Pro Glu Pro Leu Ser Lys Lys Ile Arg Glu Ser Asn Glu
                325                 330                 335

<210> SEQ ID NO 26
<211> LENGTH: 367
<212> TYPE: PRT
<213> ORGANISM: Nicotiana tabacum

<400> SEQUENCE: 26

Met Val Phe Pro Leu Asp Thr Gln Leu Leu Asn Pro Ile Phe Asp Val
1               5                   10                  15

Leu Tyr Cys Glu Glu Asp Arg Phe Leu Asp Asp Asp Leu Gly Glu
                20                  25                  30

Trp Ser Ser Thr Leu Glu Gln Val Gly Asn Asn Val Lys Lys Thr Leu
            35                  40                  45

Pro Leu Leu Glu Cys Asp Met Phe Trp Glu Asp Gln Leu Val Thr
50                  55                  60

Leu Leu Thr Lys Glu Lys Glu Ser His Leu Gly Phe Asp Cys Leu Ile
65                  70                  75                  80

Ser Asp Gly Asp Gly Phe Leu Val Glu Val Arg Lys Glu Ala Leu Asp
                85                  90                  95

Trp Met Leu Arg Val Ile Ala His Tyr Gly Phe Thr Ala Met Thr Ala
                100                 105                 110
```

Val Leu Ala Val Asn Tyr Phe Asp Arg Phe Val Ser Gly Leu Cys Phe
            115                 120                 125

Gln Lys Asp Lys Pro Trp Met Ser Gln Leu Ala Ala Val Ala Cys Leu
        130                 135                 140

Ser Ile Ala Ala Lys Val Glu Glu Thr Gln Val Pro Leu Leu Leu Asp
145                 150                 155                 160

Leu Gln Val Ala Asp Ser Arg Phe Val Phe Glu Ala Lys Thr Ile Gln
                165                 170                 175

Arg Met Glu Leu Leu Val Leu Ser Thr Leu Lys Trp Lys Met Asn Pro
            180                 185                 190

Val Thr Pro Leu Ser Phe Ile Asp His Ile Met Arg Arg Phe Gly Phe
        195                 200                 205

Met Thr Asn Leu His Leu Asp Phe Leu Arg Arg Cys Glu Arg Leu Ile
    210                 215                 220

Leu Gly Ile Ile Thr Asp Ser Arg Leu Leu His Tyr Pro Pro Ser Val
225                 230                 235                 240

Ile Ala Thr Ala Val Val Tyr Phe Val Ile Asn Glu Ile Glu Pro Cys
                245                 250                 255

Asn Ala Met Glu Tyr Gln Asn Gln Leu Met Thr Val Leu Lys Val Lys
            260                 265                 270

Gln Asp Ser Phe Glu Glu Cys His Asp Leu Ile Leu Glu Leu Met Gly
        275                 280                 285

Thr Ser Gly Tyr Asn Ile Cys Gln Ser Leu Lys Arg Lys His Gln Ser
    290                 295                 300

Val Pro Gly Ser Pro Ser Gly Val Ile Asp Ala Tyr Phe Ser Cys Asp
305                 310                 315                 320

Ser Ser Asn Asp Ser Trp Ser Val Ala Ser Ile Ser Ser Ser Pro
                325                 330                 335

Glu Pro Gln Tyr Lys Arg Ile Lys Thr Gln Asp Gln Thr Met Thr Leu
            340                 345                 350

Ala Pro Leu Ser Ser Val Ser Val Val Gly Ser Ser Pro Arg
        355                 360                 365

<210> SEQ ID NO 27
<211> LENGTH: 364
<212> TYPE: PRT
<213> ORGANISM: Oryza sativa

<400> SEQUENCE: 27

Met Ala Phe Ala Thr Leu Phe Asp Ser Leu Tyr Cys Pro Glu Glu His
1               5                   10                  15

Leu Asp Leu Phe His Asp Thr Ala Ala Asp Asp Leu His Leu Asp
            20                  25                  30

Leu His Leu His Gln Pro Pro Pro Pro Leu Leu Asp Asp Asp
            35                  40                  45

Leu Pro Ala Leu Phe His Ala Leu Arg Gly Lys Glu Asp Pro Leu Arg
        50                  55                  60

Pro Ala Ala Asp Asp Gly Tyr Gly Gly Val Ser Ala Arg Glu Ala
65                  70                  75                  80

Ala Val Gly Trp Ala Leu Arg Ala Val Ala Arg Leu Gly Phe Ser Ala
                85                  90                  95

Leu Thr Ala Ala Leu Ala Val Ala Tyr Leu Asp Arg Cys Phe Leu Gly
            100                 105                 110

Gly Ala Leu Arg Leu Gly Asp Arg Pro Trp Met Ala Arg Leu Ala Ala
        115                 120                 125

Val Ala Cys Val Ala Leu Ala Lys Val Glu Glu Thr Arg Val Pro
    130                 135                 140

Val Leu Leu Asp Leu Gln Leu Cys Ala Ala Glu Arg Ala Asp Pro Asn
145                 150                 155                 160

Glu Ala Tyr Val Phe Glu Asp Lys Thr Val Arg Arg Met Glu Leu Leu
                165                 170                 175

Val Leu Ser Ala Leu Gly Trp Arg Met His Pro Val Thr Pro Leu Ser
            180                 185                 190

Tyr Leu Gln Pro Leu Leu Gly Thr Ala His Ala Arg Leu His His
        195                 200                 205

Cys Asp Thr Ala Leu Leu Ala Leu Met Pro Asp Trp Arg Trp Pro Arg
    210                 215                 220

His Arg Pro Ser Ala Trp Ala Ala Ala Leu Ala Thr Ala Gly
225                 230                 235                 240

Trp Cys Gly Gly Gly Gly Asp Asp Ala Glu Leu Leu Ala Leu Ile
                245                 250                 255

Asp Ala Pro Lys Asp Glu Met Ala Glu Cys Ala Lys Ile Ile Ser Glu
            260                 265                 270

Glu Ala Ala Ala Ala Ala Gly Gly Ile Val Ile Gly Gly Glu Asn
        275                 280                 285

Lys Arg Lys Gly Ala Ala Gly Leu Tyr Ser Ala Pro Ala Ser Pro Ser
    290                 295                 300

Gly Val Ile Gly Ala Ser Ala Cys Phe Ser Cys Asp Ser Ser Ser Ser
305                 310                 315                 320

Ser Val Asp Ser Leu Phe Ala Ala Leu Glu Pro Pro Gly Arg Pro Ile
                325                 330                 335

Lys Arg Gly Ala Ala Ala Ala Thr Thr Ala Asp Pro Leu Pro Ala Asp
            340                 345                 350

Glu Glu Ser Arg Asp Ala Trp Pro Pro Tyr Ala Ala
        355                 360

<210> SEQ ID NO 28
<211> LENGTH: 376
<212> TYPE: PRT
<213> ORGANISM: Populus trichocarpa

<400> SEQUENCE: 28

Met Ala Ser Met Tyr Asn Pro Glu Thr Ser Ala Val Gln Asp Gln Gln
1               5                   10                  15

Gln Asn Pro Thr Leu Leu Tyr Asp Ala Leu Tyr Cys Ser Glu Glu Asn
            20                  25                  30

Trp Val Glu Glu Val Arg Glu Asp Trp Phe Gln Asp Glu Leu Glu Gly
        35                  40                  45

Glu Ser Tyr Cys Ser Asn Asn Ser Asn Lys Leu Asn Thr Phe Pro Ile
    50                  55                  60

Leu Leu Glu Gln Asp Leu Ser Trp Glu Asp Glu Leu Ser Ser Leu
65                  70                  75                  80

Phe Ala Lys Glu Glu Gln Asn Gln Leu Cys Lys Asp Leu Glu Thr Asn
                85                  90                  95

Pro Ser Leu Ala Arg Ala Arg Cys Glu Ala Val Glu Trp Ile Leu Lys
            100                 105                 110

Val Asn Glu His Tyr Ser Phe Thr Ala Leu Thr Ala Val Leu Ala Val
        115                 120                 125

Asn Tyr Leu Asp Arg Phe Leu Phe Ser Val His Leu Gln Lys Glu Lys

```
                130                 135                 140
Pro Trp Met Ala Gln Leu Ala Ala Val Ser Cys Leu Ser Leu Ala Ala
145                 150                 155                 160

Lys Val Glu Glu Thr Gln Val Pro Leu Leu Leu Asp Phe Gln Val Glu
                165                 170                 175

Asp Ser Lys Tyr Val Phe Glu Ala Lys Thr Ile Gln Arg Met Glu Ile
                180                 185                 190

Leu Val Leu Ser Thr Leu Lys Trp Lys Met Asn Pro Val Thr Pro Ile
                195                 200                 205

Ser Phe Leu Asp Tyr Ile Thr Arg Arg Leu Gly Leu Glu His Tyr Leu
        210                 215                 220

Cys Leu Glu Phe Leu Lys Arg Cys Glu Arg Met Val Leu Ser Ile Leu
225                 230                 235                 240

Ala Asp Ser Arg Ser Met Pro Tyr Val Pro Ser Val Met Ala Ala Ala
                245                 250                 255

Thr Met Leu Tyr Val Ile Asp Asn Ile Glu Pro Ser Leu Ala Ala Glu
                260                 265                 270

Tyr Gln Ser Gln Leu Leu Ser Ile Leu Gly Ile Asp Lys Asp Lys Val
        275                 280                 285

Glu Asp Cys Ser Lys Phe Leu Met Glu Phe Ala Leu Arg Asp His Phe
    290                 295                 300

Lys Leu Leu Ser Asn Lys Arg Lys Phe Cys Ser Leu Pro Gly Ser Pro
305                 310                 315                 320

Ser Gly Val Val Asp Val Ser Phe Ser Ser Asp Ser Ser Asn Asp Ser
                325                 330                 335

Trp Ser Val Ala Ser Ser Val Ser Ser Ser Pro Lys Pro Leu Ser Lys
                340                 345                 350

Lys Ser Arg Ala Leu Gln Ser Leu Asn Asn Ala Thr Thr Ser Asp Phe
        355                 360                 365

Ser Gln His Ser Ser Pro Val Pro
        370                 375

<210> SEQ ID NO 29
<211> LENGTH: 335
<212> TYPE: PRT
<213> ORGANISM: Arabidopsis thaliana

<400> SEQUENCE: 29

Met Arg Ser Tyr Arg Phe Ser Asp Tyr Leu His Met Ser Val Ser Phe
1               5                   10                  15

Ser Asn Asp Met Asp Leu Phe Cys Gly Glu Asp Ser Gly Val Phe Ser
                20                  25                  30

Gly Glu Ser Thr Val Asp Phe Ser Ser Glu Val Asp Ser Trp Pro
            35                  40                  45

Gly Asp Ser Ile Ala Cys Phe Ile Glu Asp Glu Arg His Phe Val Pro
        50                  55                  60

Gly His Asp Tyr Leu Ser Arg Phe Gln Thr Arg Ser Leu Asp Ala Ser
65                  70                  75                  80

Ala Arg Glu Asp Ser Val Ala Trp Ile Leu Lys Val Gln Ala Tyr Tyr
                85                  90                  95

Asn Phe Gln Pro Leu Thr Ala Tyr Leu Ala Val Asn Tyr Met Asp Arg
                100                 105                 110

Phe Leu Tyr Ala Arg Arg Leu Pro Glu Thr Ser Gly Trp Pro Met Gln
        115                 120                 125
```

```
Leu Leu Ala Val Ala Cys Leu Ser Leu Ala Ala Lys Met Glu Glu Ile
    130                 135                 140

Leu Val Pro Ser Leu Phe Asp Phe Gln Val Ala Gly Val Lys Tyr Leu
145                 150                 155                 160

Phe Glu Ala Lys Thr Ile Lys Arg Met Glu Leu Leu Val Leu Ser Val
                165                 170                 175

Leu Asp Trp Arg Leu Arg Ser Val Thr Pro Phe Asp Phe Ile Ser Phe
            180                 185                 190

Phe Ala Tyr Lys Ile Asp Pro Ser Gly Thr Phe Leu Gly Phe Phe Ile
        195                 200                 205

Ser His Ala Thr Glu Ile Ile Leu Ser Asn Ile Lys Glu Ala Ser Phe
    210                 215                 220

Leu Glu Tyr Trp Pro Ser Ser Ile Ala Ala Ala Ile Leu Cys Val
225                 230                 235                 240

Ala Asn Glu Leu Pro Ser Leu Ser Ser Val Val Asn Pro His Glu Ser
                245                 250                 255

Pro Glu Thr Trp Cys Asp Gly Leu Ser Lys Glu Lys Ile Val Arg Cys
            260                 265                 270

Tyr Arg Leu Met Lys Ala Met Ala Ile Glu Asn Asn Arg Leu Asn Thr
        275                 280                 285

Pro Lys Val Ile Ala Lys Leu Arg Val Ser Val Arg Ala Ser Ser Thr
    290                 295                 300

Leu Thr Arg Pro Ser Asp Glu Ser Ser Ser Pro Cys Lys Arg Arg Lys
305                 310                 315                 320

Leu Ser Gly Tyr Ser Trp Val Gly Asp Glu Thr Ser Thr Ser Asn
                325                 330                 335

<210> SEQ ID NO 30
<211> LENGTH: 361
<212> TYPE: PRT
<213> ORGANISM: Arabidopsis thaliana

<400> SEQUENCE: 30

Met Ala Glu Asn Leu Ala Cys Gly Glu Thr Ser Glu Ser Trp Ile Ile
1               5                   10                  15

Asp Asn Asp Asp Asp Asp Ile Asn Tyr Gly Gly Gly Phe Thr Asn Glu
                20                  25                  30

Ile Asp Tyr Asn His Gln Leu Phe Ala Lys Asp Asp Asn Phe Gly Gly
            35                  40                  45

Asn Gly Ser Ile Pro Met Met Gly Ser Ser Ser Ser Leu Ser Glu
    50                  55                  60

Asp Arg Ile Lys Glu Met Leu Val Arg Glu Ile Glu Phe Cys Pro Gly
65                  70                  75                  80

Thr Asp Tyr Val Lys Arg Leu Leu Ser Gly Asp Leu Asp Leu Ser Val
                85                  90                  95

Arg Asn Gln Ala Leu Asp Trp Ile Leu Lys Val Cys Ala His Tyr His
            100                 105                 110

Phe Gly His Leu Cys Ile Cys Leu Ser Met Asn Tyr Leu Asp Arg Phe
        115                 120                 125

Leu Thr Ser Tyr Glu Leu Pro Lys Asp Lys Asp Trp Ala Ala Gln Leu
    130                 135                 140

Leu Ala Val Ser Cys Leu Ser Leu Ala Ser Lys Met Glu Glu Thr Asp
145                 150                 155                 160

Val Pro His Ile Val Asp Leu Gln Val Glu Asp Pro Lys Phe Val Phe
                165                 170                 175
```

```
Glu Ala Lys Thr Ile Lys Arg Met Glu Leu Leu Val Val Thr Thr Leu
                180                 185                 190

Asn Trp Arg Leu Gln Ala Leu Thr Pro Phe Ser Phe Ile Asp Tyr Phe
            195                 200                 205

Val Asp Lys Ile Ser Gly His Val Ser Glu Asn Leu Ile Tyr Arg Ser
        210                 215                 220

Ser Arg Phe Ile Leu Asn Thr Thr Lys Ala Ile Glu Phe Leu Asp Phe
225                 230                 235                 240

Arg Pro Ser Glu Ile Ala Ala Ala Ala Val Ser Val Ser Ile Ser
                245                 250                 255

Gly Glu Thr Glu Cys Ile Asp Glu Glu Lys Ala Leu Ser Ser Leu Ile
                260                 265                 270

Tyr Val Lys Gln Glu Arg Val Lys Arg Cys Leu Asn Leu Met Arg Ser
                275                 280                 285

Leu Thr Gly Glu Glu Asn Val Arg Gly Thr Ser Leu Ser Gln Glu Gln
                290                 295                 300

Ala Arg Val Ala Val Arg Ala Val Pro Ala Ser Pro Val Gly Val Leu
305                 310                 315                 320

Glu Ala Thr Cys Leu Ser Tyr Arg Ser Glu Glu Arg Thr Val Glu Ser
                325                 330                 335

Cys Thr Asn Ser Ser Gln Ser Ser Pro Asp Asn Asn Asn Asn Asn Asn
                340                 345                 350

Asn Ser Asn Lys Arg Arg Arg Lys Gln
            355                 360

<210> SEQ ID NO 31
<211> LENGTH: 308
<212> TYPE: PRT
<213> ORGANISM: Arabidopsis thaliana

<400> SEQUENCE: 31

Met Ala Glu Glu Asn Leu Glu Leu Ser Leu Leu Cys Thr Glu Ser Asn
1               5                   10                  15

Val Asp Asp Glu Gly Met Ile Val Asp Glu Thr Pro Ile Glu Ile Ser
                20                  25                  30

Ile Pro Gln Met Gly Phe Ser Gln Ser Glu Ser Glu Glu Ile Ile Met
            35                  40                  45

Glu Met Val Glu Lys Glu Lys Gln His Leu Pro Ser Asp Asp Tyr Ile
        50                  55                  60

Lys Arg Leu Arg Ser Gly Asp Leu Asp Leu Asn Val Gly Arg Arg Asp
65                  70                  75                  80

Ala Leu Asn Trp Ile Trp Lys Ala Cys Glu Val His Gln Phe Gly Pro
                85                  90                  95

Leu Cys Phe Cys Leu Ala Met Asn Tyr Leu Asp Arg Phe Leu Ser Val
                100                 105                 110

His Asp Leu Pro Ser Gly Lys Gly Trp Ile Leu Gln Leu Leu Ala Val
            115                 120                 125

Ala Cys Leu Ser Leu Ala Ala Lys Ile Glu Glu Thr Glu Val Pro Met
        130                 135                 140

Leu Ile Asp Leu Gln Val Gly Asp Pro Gln Phe Val Phe Glu Ala Lys
145                 150                 155                 160

Ser Val Gln Arg Met Glu Leu Leu Val Leu Asn Lys Leu Lys Trp Arg
                165                 170                 175

Leu Arg Ala Ile Thr Pro Cys Ser Tyr Ile Arg Tyr Phe Leu Arg Lys
```

-continued

```
                    180                 185                 190
Met Ser Lys Cys Asp Gln Glu Pro Ser Asn Thr Leu Ile Ser Arg Ser
            195                 200                 205

Leu Gln Val Ile Ala Ser Thr Thr Lys Gly Ile Asp Phe Leu Glu Phe
        210                 215                 220

Arg Pro Ser Glu Ala Ala Ala Val Ala Leu Ser Val Ser Gly Glu
225                 230                 235                 240

Leu Gln Arg Val His Phe Asp Asn Ser Ser Phe Ser Pro Leu Phe Ser
                245                 250                 255

Leu Leu Gln Lys Glu Arg Val Lys Lys Ile Gly Glu Met Ile Glu Ser
            260                 265                 270

Asp Gly Ser Asp Leu Cys Ser Gln Thr Pro Asn Gly Val Leu Glu Val
        275                 280                 285

Ser Ala Cys Cys Phe Ser Phe Lys Thr His Asp Ser Ser Ser Ser Tyr
    290                 295                 300

Thr His Leu Ser
305

<210> SEQ ID NO 32
<211> LENGTH: 260
<212> TYPE: PRT
<213> ORGANISM: Arabidopsis thaliana

<400> SEQUENCE: 32

Met Ala Glu Phe Met Glu Pro Asn Leu Val Ser Asn Phe Asp Asp Glu
1               5                   10                  15

Lys Ser Asn Ser Val Asp Thr Arg Ser Ile Phe Gln Met Gly Phe Pro
            20                  25                  30

Leu Glu Ser Glu Glu Ile Val Arg Glu Met Ile Glu Lys Glu Arg Gln
        35                  40                  45

His Ser Pro Arg Asp Asp Tyr Leu Lys Arg Leu Arg Asn Gly Asp Leu
    50                  55                  60

Asp Phe Asn Val Arg Ile Gln Ala Leu Gly Trp Ile Trp Lys Ala Cys
65                  70                  75                  80

Glu Glu Leu Gln Phe Gly Pro Leu Cys Ile Cys Leu Ala Met Asn Tyr
                85                  90                  95

Leu Asp Arg Phe Leu Ser Val His Asp Leu Pro Ser Gly Lys Ala Trp
            100                 105                 110

Thr Val Gln Leu Leu Ala Val Ala Cys Leu Ser Leu Ala Ala Lys Ile
        115                 120                 125

Glu Glu Thr Asn Val Pro Glu Leu Met Gln Leu Gln Val Gly Ala Pro
    130                 135                 140

Met Phe Val Phe Glu Ala Lys Ser Val Gln Arg Met Glu Leu Leu Val
145                 150                 155                 160

Leu Asn Val Leu Arg Trp Arg Leu Arg Ala Val Thr Pro Cys Ser Tyr
                165                 170                 175

Val Arg Tyr Phe Leu Ser Lys Ile Asn Gly Tyr Asp Gln Glu Pro His
            180                 185                 190

Ser Arg Leu Val Thr Arg Ser Leu Gln Val Ile Ala Ser Thr Thr Lys
        195                 200                 205

Gly Ile Asp Phe Leu Glu Phe Arg Ala Ser Glu Ile Ala Ala Ala Val
    210                 215                 220

Ala Leu Ser Val Ser Gly Glu His Phe Asp Lys Phe Ser Phe Ser Ser
225                 230                 235                 240
```

Ser Phe Ser Ser Leu Glu Lys Val Arg Glu Val Thr Lys Ser Leu Leu
                245                 250                 255

His Leu Gln Lys
            260

<210> SEQ ID NO 33
<211> LENGTH: 323
<212> TYPE: PRT
<213> ORGANISM: Arabidopsis thaliana

<400> SEQUENCE: 33

Met Gly Glu Pro Lys Asp Ser Leu Ala Leu Phe Leu Cys His Glu Ser
1               5                   10                  15

Glu Ser Ser Leu Asn Glu Asp Asp Glu Thr Ile Glu Arg Ser Asp
            20                  25                  30

Lys Gln Glu Pro His Phe Thr Thr Ile Asp Asp Glu Asp Tyr Val
        35                  40                  45

Ala Asp Leu Val Leu Lys Glu Asn Leu Arg Phe Glu Thr Leu Pro Ser
    50                  55                  60

Lys Thr Thr Ser Ser Asp Arg Leu Ile Ala Ile Asp Trp Ile Leu
65                  70                  75                  80

Thr Thr Arg Thr Arg Phe Gly Phe Gln His Gln Thr Ala Tyr Ile Ala
                85                  90                  95

Ile Ser Tyr Phe Asp Leu Phe Leu His Lys Arg Phe Ile Gly Leu Gln
                100                 105                 110

Lys Asp Glu Thr Trp Ala Met Arg Leu Leu Ser Val Ala Cys Leu Ser
            115                 120                 125

Leu Ala Ala Lys Met Glu Glu Arg Ile Val Pro Gly Leu Ser Gln Tyr
    130                 135                 140

Pro Gln Asp His Asp Phe Val Phe Lys Pro Asp Val Ile Arg Lys Thr
145                 150                 155                 160

Glu Leu Leu Ile Leu Ser Thr Leu Asp Trp Lys Met Asn Leu Ile Thr
                165                 170                 175

Pro Phe His Tyr Phe Asn Tyr Phe Leu Ala Lys Ile Ser Gln Asp Asn
            180                 185                 190

His Ser Val Ser Lys Asp Leu Val Leu Arg Ser Ser Asp Ser Leu
        195                 200                 205

Leu Ala Leu Thr Lys Glu Ile Ser Phe Thr Glu Tyr Arg Gln Phe Val
    210                 215                 220

Val Ala Ala Val Thr Thr Leu Leu Ala Ser Ser Ser Thr Ser Ser Asp
225                 230                 235                 240

Ile Arg Leu Thr Arg Glu Glu Ile Ala Asn Lys Phe Gly Ser Ile Ser
                245                 250                 255

Trp Trp Thr Ser Asn Glu Asn Glu Asn Val Tyr Leu Cys Tyr Gln Arg
            260                 265                 270

Thr Leu Glu Ile Glu Glu Arg Lys His Met Thr Pro Pro Glu Ile
        275                 280                 285

Ala Val Ser Arg Glu Pro Pro Ala Ser Gly Ser Gly Ala Lys Arg Arg
    290                 295                 300

Leu Ser Phe Asp Asp Ser Asp Gln Ser Ser Pro Pro Ala Lys Arg Met
305                 310                 315                 320

Arg Arg Leu

<210> SEQ ID NO 34
<211> LENGTH: 302

```
<212> TYPE: PRT
<213> ORGANISM: Arabidopsis thaliana

<400> SEQUENCE: 34

Met Glu Phe His Leu Glu His Pro Leu Ser His Ser Leu His Asn
1               5                   10                  15

Asn Phe Asn Asp Asp Thr Asp Tyr Glu Thr Leu Pro His Ser Leu Phe
            20                  25                  30

Leu Val Glu Phe Gln His Met Pro Ser Ser His Tyr Phe His Ser Leu
        35                  40                  45

Lys Ser Ser Ala Phe Leu Leu Ser Asn Arg Asn Gln Ala Ile Ser Ser
    50                  55                  60

Ile Thr Gln Tyr Ser Arg Lys Phe Asp Asp Pro Ser Leu Thr Tyr Leu
65                  70                  75                  80

Ala Val Asn Tyr Leu Asp Arg Phe Leu Ser Ser Glu Asp Met Pro Gln
                85                  90                  95

Ser Lys Pro Trp Ile Leu Lys Leu Ile Ser Leu Ser Cys Val Ser Leu
            100                 105                 110

Ser Ala Lys Met Arg Lys Pro Asp Met Ser Val Ser Asp Leu Pro Val
        115                 120                 125

Glu Gly Glu Phe Phe Asp Ala Gln Met Ile Glu Arg Met Glu Asn Val
130                 135                 140

Ile Leu Gly Ala Leu Lys Trp Arg Met Arg Ser Val Thr Pro Phe Ser
145                 150                 155                 160

Phe Leu Ala Phe Phe Ile Ser Leu Phe Glu Leu Lys Glu Glu Asp Pro
                165                 170                 175

Leu Leu Leu Lys His Ser Leu Lys Ser Gln Thr Ser Asp Leu Thr Phe
            180                 185                 190

Ser Leu Gln His Asp Ile Ser Phe Leu Glu Phe Lys Pro Ser Val Ile
        195                 200                 205

Ala Gly Ala Ala Leu Leu Phe Ala Ser Phe Glu Leu Cys Pro Leu Gln
    210                 215                 220

Phe Pro Cys Phe Ser Asn Arg Ile Asn Gln Cys Thr Tyr Val Asn Lys
225                 230                 235                 240

Asp Glu Leu Met Glu Cys Tyr Lys Ala Ile Gln Glu Arg Asp Ile Ile
                245                 250                 255

Val Gly Glu Asn Glu Gly Ser Thr Glu Thr Ala Val Asn Val Leu Asp
            260                 265                 270

Gln Gln Phe Ser Ser Cys Glu Ser Asp Lys Ser Ile Thr Ile Thr Ala
        275                 280                 285

Ser Ser Ser Pro Lys Arg Arg Lys Thr Ser Thr Arg Arg Tyr
    290                 295                 300

<210> SEQ ID NO 35
<211> LENGTH: 341
<212> TYPE: PRT
<213> ORGANISM: Arabidopsis thaliana

<400> SEQUENCE: 35

Met Asp Asn Leu Leu Cys Glu Glu Ser Trp Pro Ala Ser Pro Leu Thr
1               5                   10                  15

Pro Glu Pro Leu Pro Asn Phe Arg His Arg Ser His Asp Asn Asp Val
            20                  25                  30

Val Lys Met Tyr Pro Glu Ile Asp Ala Ala Thr Met Glu Glu Ala Ile
        35                  40                  45
```

Ala Met Asp Leu Glu Lys Glu Leu Cys Phe Asn Asn His Gly Asp Lys
 50                  55                  60

Phe Val Glu Phe Val Ser Lys Lys Leu Thr Asp Tyr Arg Phe His
 65                  70                  75                  80

Ala Phe Gln Trp Leu Ile Gln Thr Arg Ser Arg Leu Asn Leu Ser Tyr
                     85                  90                  95

Glu Thr Val Phe Ser Ala Ala Asn Cys Phe Asp Arg Phe Val Tyr Met
                    100                 105                 110

Thr Cys Cys Asp Glu Trp Thr Asn Trp Met Val Glu Leu Val Ala Val
                    115                 120                 125

Thr Ser Leu Ser Ile Ala Ser Lys Phe Asn Glu Val Thr Thr Pro Leu
        130                 135                 140

Leu Glu Glu Leu Glu Met Glu Gly Leu Thr His Met Phe His Val Asn
145                 150                 155                 160

Thr Val Ala Gln Met Glu Leu Ile Ile Leu Lys Ala Leu Glu Trp Arg
                    165                 170                 175

Val Asn Ala Val Thr Ser Tyr Thr Phe Ser Gln Thr Leu Val Ser Lys
                    180                 185                 190

Ile Gly Met Val Gly Asp His Met Ile Met Asn Arg Ile Thr Asn His
            195                 200                 205

Leu Leu Asp Val Ile Cys Asp Leu Lys Met Leu Gln Tyr Pro Pro Ser
210                 215                 220

Val Val Ala Thr Ala Ala Ile Trp Ile Leu Met Glu Asp Lys Val Cys
225                 230                 235                 240

Arg Glu Ser Ile Met Asn Leu Phe Glu Gln Asn His Lys Glu Lys Ile
                    245                 250                 255

Val Lys Cys Val Asp Gly Met Lys Asn Arg Asp Ile Asp His Gln Ser
            260                 265                 270

Ser Arg Arg Arg Tyr Ser Glu Gly Arg Ser Ile Leu Ser Leu Leu Gln
        275                 280                 285

Arg Gly Asp Val Met Asn Met Asn Gly Asp Tyr Asn Val Glu Asp Leu
        290                 295                 300

Ser Lys Ile Phe Gln Ile Phe Arg Tyr Glu Lys Lys Arg Asp Arg
305                 310                 315                 320

Gly Asn His Gln Asp Asn Ile Arg Pro Ala Lys Arg Met Thr Ile Glu
                    325                 330                 335

Met Ser Asn Tyr Ile
            340

<210> SEQ ID NO 36
<211> LENGTH: 315
<212> TYPE: PRT
<213> ORGANISM: Helianthus tuberosus

<400> SEQUENCE: 36

Met Ser Ile Ser Cys Ser Asp Cys Phe Ser Asp Leu Leu Cys Cys Glu
 1                   5                  10                  15

Asp Ser Gly Ile Leu Ser Gly Asp Asp Arg Pro Glu Cys Ser Tyr Asp
                 20                  25                  30

Phe Glu Tyr Ser Gly Asp Phe Asp Ser Ile Ala Glu Phe Ile Glu
            35                  40                  45

Gln Glu Arg Lys Phe Val Pro Gly Ile Asp Tyr Val Glu Arg Phe Gln
     50                  55                  60

Ser Gln Val Leu Asp Ala Ser Ala Arg Glu Glu Ser Val Ala Trp Ile
 65                  70                  75                  80

```
Leu Lys Val Gln Arg Phe Tyr Gly Phe Gln Pro Leu Thr Ala Tyr Leu
                85                  90                  95

Ser Val Asn Tyr Leu Asp Arg Phe Ile Tyr Cys Arg Gly Phe Pro Val
            100                 105                 110

Ala Asn Gly Trp Pro Leu Gln Leu Leu Ser Val Ala Cys Leu Ser Leu
        115                 120                 125

Ala Ala Lys Met Glu Glu Thr Leu Ile Pro Ser Ile Leu Asp Leu Gln
    130                 135                 140

Val Glu Gly Ala Lys Tyr Ile Phe Glu Pro Lys Thr Ile Arg Arg Met
145                 150                 155                 160

Glu Phe Leu Val Leu Ser Val Leu Asp Trp Arg Leu Arg Ser Val Thr
                165                 170                 175

Pro Phe Ser Phe Ile Gly Phe Phe Ser His Lys Ile Asp Pro Ser Gly
            180                 185                 190

Met Tyr Thr Gly Phe Leu Ile Ser Arg Ala Thr Gln Ile Ile Leu Ser
        195                 200                 205

Asn Ile Gln Glu Ala Ser Leu Leu Glu Tyr Trp Pro Ser Cys Ile Ala
    210                 215                 220

Ala Ala Thr Ile Leu Cys Ala Ala Ser Asp Leu Ser Lys Phe Ser Leu
225                 230                 235                 240

Ile Asn Ala Asp His Ala Glu Ser Trp Cys Asp Gly Leu Ser Lys Glu
                245                 250                 255

Lys Ile Thr Lys Cys Tyr Arg Leu Val Gln Ser Pro Lys Ile Leu Pro
            260                 265                 270

Val His Val Arg Val Met Thr Ala Arg Val Ser Thr Glu Ser Gly Asp
        275                 280                 285

Ser Ser Ser Ser Ser Ser Pro Ser Pro Tyr Lys Arg Lys Leu
    290                 295                 300

Asn Asn Tyr Ser Trp Ile Glu Glu Asp Lys Arg
305                 310                 315

<210> SEQ ID NO 37
<211> LENGTH: 354
<212> TYPE: PRT
<213> ORGANISM: Nicotiana tabacum

<400> SEQUENCE: 37

Met Ala Ala Asp Asn Ile Tyr Asp Phe Val Ala Ser Asn Leu Leu Cys
1               5                   10                  15

Thr Glu Thr Lys Ser Leu Cys Phe Asp Asp Val Asp Ser Leu Thr Ile
                20                  25                  30

Ser Gln Gln Asn Ile Glu Thr Lys Ser Lys Asp Leu Ser Phe Asn Asn
            35                  40                  45

Gly Ile Arg Ser Glu Pro Leu Ile Asp Leu Pro Ser Leu Ser Glu Glu
        50                  55                  60

Cys Leu Ser Phe Met Val Gln Arg Glu Met Glu Phe Leu Pro Lys Asp
65                  70                  75                  80

Asp Tyr Val Glu Arg Leu Arg Ser Gly Asp Leu Asp Leu Ser Val Arg
                85                  90                  95

Lys Glu Ala Leu Asp Trp Ile Leu Lys Ala His Met His Tyr Gly Phe
            100                 105                 110

Gly Glu Leu Ser Phe Cys Leu Ser Ile Asn Tyr Leu Asp Arg Phe Leu
        115                 120                 125

Ser Leu Tyr Glu Leu Pro Arg Ser Lys Thr Trp Thr Val Gln Leu Leu
```

```
                130                 135                 140
Ala Val Ala Cys Leu Ser Leu Ala Ala Lys Met Glu Glu Ile Asn Val
145                 150                 155                 160

Pro Leu Thr Val Asp Leu Gln Val Gly Asp Pro Lys Phe Val Phe Glu
                165                 170                 175

Gly Lys Thr Ile Gln Arg Met Glu Leu Leu Val Leu Ser Thr Leu Lys
                180                 185                 190

Trp Arg Met Gln Ala Tyr Thr Pro Tyr Thr Phe Ile Asp Tyr Phe Met
                195                 200                 205

Arg Lys Met Asn Gly Asp Gln Ile Pro Ser Arg Pro Leu Ile Ser Gly
                210                 215                 220

Ser Met Gln Leu Ile Leu Ser Ile Ile Arg Ser Ile Asp Phe Leu Glu
225                 230                 235                 240

Phe Arg Ser Ser Glu Ile Ala Ala Ser Val Ala Met Ser Val Ser Gly
                245                 250                 255

Glu Ile Gln Ala Lys Asp Ile Asp Lys Ala Met Pro Cys Phe Phe Ile
                260                 265                 270

His Leu Asp Lys Gly Arg Val Gln Lys Cys Val Glu Leu Ile Gln Asp
                275                 280                 285

Leu Thr Thr Ala Thr Ile Thr Thr Ala Ala Ala Ser Leu Val Pro
                290                 295                 300

Gln Ser Pro Ile Gly Val Leu Glu Ala Ala Cys Leu Ser Tyr Lys
305                 310                 315                 320

Ser Gly Asp Glu Arg Thr Val Gly Ser Cys Thr Thr Ser His Thr
                325                 330                 335

Lys Arg Arg Lys Leu Asp Thr Ser Ser Leu Glu His Gly Thr Ser Glu
                340                 345                 350

Lys Leu

<210> SEQ ID NO 38
<211> LENGTH: 345
<212> TYPE: PRT
<213> ORGANISM: Oryza sativa

<400> SEQUENCE: 38

Met Gly Asp Ala Ser Ala Ser Thr Ser Ala Pro Ala Thr Pro Thr Ser
1               5                   10                  15

Thr Leu Ile Cys Arg Glu Asp Gly Asn Asp Leu Phe Ser Ala Asp Pro
                20                  25                  30

Ala Asp Asp Gly Gly Gly Ser Gly Gly Asp Trp Glu Leu Ser
                35                  40                  45

Ile Ala Asp Asp His Val Leu Leu Met Asp Arg Asp Asp Glu Tyr
                50                  55                  60

Leu Ala Leu Met Leu Ser Lys Glu Arg Cys Ala Gly Gly Gly Gly
65                  70                  75                  80

Gly Glu Arg Gly Asp Glu Glu Glu Glu Met Val Glu Glu Trp Met
                85                  90                  95

Lys Asn Ala Arg Ser Trp Cys Val Gly Trp Ile Val Lys Thr Asn Ala
                100                 105                 110

Gly Phe Arg Phe Ser Leu Lys Thr Ala Tyr Val Ala Val Ser Tyr Leu
                115                 120                 125

Asp Arg Phe Leu Ala Arg Arg Cys Val Asp Arg Asp Lys Glu Trp Ala
                130                 135                 140

Leu Gln Leu Leu Ser Val Ala Cys Leu Ser Leu Ala Ala Lys Val Glu
```

```
            145                 150                 155                 160
Glu Arg Arg Pro Pro Arg Leu Pro Glu Phe Lys Leu Asp Met Tyr Asp
                165                 170                 175

Cys Ala Ser Leu Met Arg Met Glu Leu Leu Val Leu Thr Thr Leu Lys
            180                 185                 190

Trp Gln Met Ile Thr Glu Thr Pro Phe Ser Tyr Leu Asn Cys Phe Thr
            195                 200                 205

Ala Lys Phe Arg His Asp Glu Arg Lys Ala Ile Val Leu Arg Ala Ile
        210                 215                 220

Glu Cys Ile Phe Ala Ser Ile Lys Val Ile Ser Ser Val Gly Tyr Gln
225                 230                 235                 240

Pro Ser Thr Ile Ala Leu Ala Ala Ile Leu Ile Ala Arg Asn Lys Glu
                245                 250                 255

Thr Ala Pro Asn Leu Asp Glu Leu Lys Ser Val Val Gly Ser Leu Trp
            260                 265                 270

Gln Gln Leu Asp Thr Gly His Val Tyr Ser Cys Tyr Asn Lys Met Met
        275                 280                 285

Ile Gln Glu Asp Arg Ser Met Gln Ser Thr Thr Glu Val Ala Ser Ser
290                 295                 300

Gly Val Ser Val Ala His Ile Gly Gly Ser Glu Asp Ser Ala Met Gly
305                 310                 315                 320

Gly Ala Asn Asn Ala Thr Thr Leu Glu Ala Thr Pro Asp Lys Lys Arg
                325                 330                 335

Lys Arg Leu His Ser Pro Gln Arg Gln
            340                 345

<210> SEQ ID NO 39
<211> LENGTH: 353
<212> TYPE: PRT
<213> ORGANISM: Triticum aestivum

<400> SEQUENCE: 39

Met Val Pro Ser Gly Tyr Asp Cys Ala Ala Ser Val Leu Leu Cys Ala
1               5                   10                  15

Glu Asp Asn Ala Ala Ile Leu Gly Leu Asp Asp Asp Glu Glu Asp Cys
            20                  25                  30

Ser Trp Ala Ala Ala Ala Ala Thr Pro Pro Arg Ile Ala Ala Asp Ala
        35                  40                  45

Ala Ala Ala Ala Glu Gly Phe Leu Val Asp His Pro Val Gln Ser Asp
    50                  55                  60

Glu Cys Val Ala Ala Leu Val Glu Thr Glu Lys Glu His Met Pro Ala
65                  70                  75                  80

Asp Gly Tyr Pro Gln Met Leu Leu Arg Arg Pro Gly Ala Leu Asp Leu
                85                  90                  95

Ala Ala Val Arg Arg Asp Ala Ile Asp Trp Ile Trp Glu Val Ile Glu
            100                 105                 110

His Phe Asn Phe Ala Pro Leu Thr Ala Val Leu Ser Val Asn Tyr Leu
        115                 120                 125

Asp Arg Phe Leu Ser Val Tyr Pro Leu Pro Glu Gly Lys Ala Trp Val
    130                 135                 140

Thr Gln Leu Leu Ala Val Ala Cys Leu Ser Leu Ala Ser Lys Met Glu
145                 150                 155                 160

Glu Thr Tyr Val Pro Leu Pro Val Asp Leu Gln Val Val Glu Ala Asn
                165                 170                 175
```

```
Ser Ala Phe Glu Gly Arg Thr Ile Lys Arg Met Glu Leu Leu Val Leu
                180                 185                 190

Ser Thr Leu Lys Trp Arg Met Gln Ala Val Thr Ala Cys Ser Phe Ile
        195                 200                 205

Asp Tyr Phe Leu Arg Lys Phe Asn Asp His Asp Ala Pro Ser Met Leu
    210                 215                 220

Ala Phe Ser Arg Ser Thr Asp Leu Ile Leu Ser Thr Ala Lys Gly Ala
225                 230                 235                 240

Asp Phe Leu Val Phe Arg Pro Ser Glu Ile Ala Ala Ser Val Ala Leu
                245                 250                 255

Ala Ala Phe Gly Glu Arg Asn Thr Ser Val Val Glu Arg Ala Thr Thr
                260                 265                 270

Thr Cys Lys Phe Ile Asn Lys Glu Arg Val Leu Arg Cys Tyr Glu Leu
        275                 280                 285

Ile Gln Asp Lys Val Ala Met Gly Thr Ile Val Leu Lys Ser Ala Gly
    290                 295                 300

Ser Ser Met Phe Ser Val Pro Gln Ser Pro Ile Gly Val Ser Asp Ala
305                 310                 315                 320

Ala Ala Cys Leu Ser Gln Gln Ser Asp Asp Thr Ala Val Gly Ser Pro
                325                 330                 335

Ala Thr Cys Tyr Gln Ala Ser Ser Ala Ser Lys Arg Arg Arg Ile Gly
                340                 345                 350

Arg

<210> SEQ ID NO 40
<211> LENGTH: 358
<212> TYPE: PRT
<213> ORGANISM: Zea mays

<400> SEQUENCE: 40

Met Val Pro Gly Tyr Asp Cys Ala Ala Ser Val Leu Leu Cys Ala Glu
1               5                   10                  15

Asp Asn Ala Ala Ile Leu Gly Leu Asp Asp Asp Gly Glu Glu Ser Ser
                20                  25                  30

Trp Ala Ala Ala Thr Pro Pro Arg Asp Thr Val Ala Ala Ala Ala
            35                  40                  45

Ala Thr Gly Val Ala Val Asp Gly Ile Leu Thr Glu Phe Pro Leu Leu
    50                  55                  60

Ser Asp Asp Cys Val Ala Thr Leu Val Glu Lys Glu Val Glu His Met
65                  70                  75                  80

Pro Ala Glu Gly Tyr Leu Gln Lys Leu Gln Arg Arg His Gly Asp Leu
                85                  90                  95

Asp Leu Ala Ala Val Arg Lys Asp Ala Ile Asp Trp Ile Trp Lys Val
            100                 105                 110

Ile Glu His Tyr Asn Phe Ala Pro Leu Thr Ala Val Leu Ser Val Asn
        115                 120                 125

Tyr Leu Asp Arg Phe Leu Ser Thr Tyr Glu Phe Pro Glu Gly Arg Ala
    130                 135                 140

Trp Met Thr Gln Leu Leu Ala Val Ala Cys Leu Ser Leu Ala Ser Lys
145                 150                 155                 160

Ile Glu Glu Thr Phe Val Pro Leu Pro Leu Asp Leu Gln Val Ala Glu
                165                 170                 175

Ala Lys Phe Val Phe Glu Gly Arg Thr Ile Lys Arg Met Glu Leu Leu
                180                 185                 190
```

```
Val Leu Ser Thr Leu Lys Trp Arg Met His Ala Val Thr Ala Cys Ser
            195                 200                 205

Phe Val Glu Tyr Phe Leu His Lys Leu Ser Asp His Gly Ala Pro Ser
210                 215                 220

Leu Leu Ala Arg Ser Arg Ser Ser Asp Leu Val Leu Ser Thr Ala Lys
225                 230                 235                 240

Gly Ala Glu Phe Val Val Phe Arg Pro Ser Glu Ile Ala Ala Ser Val
                245                 250                 255

Ala Leu Ala Ala Ile Gly Glu Cys Arg Ser Val Ile Glu Arg Ala
            260                 265                 270

Ala Ser Ser Cys Lys Tyr Leu Asp Lys Glu Arg Val Leu Arg Cys His
        275                 280                 285

Glu Met Ile Gln Glu Lys Ile Thr Ala Gly Ser Ile Val Leu Lys Ser
290                 295                 300

Ala Gly Ser Ser Ile Ser Ser Val Pro Gln Ser Pro Ile Gly Val Leu
305                 310                 315                 320

Asp Ala Ala Ala Cys Leu Ser Gln Gln Ser Asp Asp Ala Thr Val Gly
                325                 330                 335

Ser Pro Ala Val Cys Tyr His Ser Ser Thr Ser Lys Arg Arg Arg
                340                 345                 350

Ile Thr Arg Arg Leu Leu
        355

<210> SEQ ID NO 41
<211> LENGTH: 359
<212> TYPE: PRT
<213> ORGANISM: Medicago sativa

<400> SEQUENCE: 41

Met Ile Glu Glu Glu Gln Leu Pro Ala Ile Leu Met Pro Ser Asp Cys
1               5                   10                  15

Glu Leu Leu Cys Gly Glu Asp Ser Ser Glu Val Leu Thr Gly Asp Leu
                20                  25                  30

Pro Glu Cys Ser Ser Asp Leu Asp Ser Ser Ser Ser Gln Leu Pro
            35                  40                  45

Ser Ser Ser Leu Phe Ala Glu Glu Glu Asp Ser Ile Ala Val Phe
50                  55                  60

Ile Glu His Glu Phe Lys Phe Val Pro Gly Phe Asp Tyr Val Ser Arg
65                  70                  75                  80

Phe Gln Ser Arg Ser Leu Glu Ser Ser Thr Arg Glu Glu Ala Ile Ala
                85                  90                  95

Trp Ile Leu Lys Val His Glu Tyr Tyr Gly Phe Gln Pro Leu Thr Ala
            100                 105                 110

Tyr Leu Ser Val Asn Tyr Met Asp Arg Phe Leu Asp Ser Arg Pro Leu
        115                 120                 125

Pro Gly Ile Lys Trp Met Ala Thr Ala Thr Phe Ile Cys Cys Met Phe
130                 135                 140

Val Phe Ser Ser Lys Asp Gly Gly Pro Leu Val Pro Ser Leu Leu Asp
145                 150                 155                 160

Phe Gln Ile Glu Gly Ala Lys Tyr Ile Phe Gln Pro Arg Thr Met Leu
                165                 170                 175

Ile Met Glu Leu Leu Val Leu Thr Ile Leu Asp Trp Arg Leu Arg Ser
            180                 185                 190

Ile Thr His Leu Val Ser Ser Val Ser Leu Arg Ala Thr Arg Phe Thr
        195                 200                 205
```

Gly Thr Phe Asn His Phe Ile Ile Ser Arg Ala Thr Glu Ile Ile Leu
            210                 215                 220

Ser Asn Ile Arg Asp Ala Ser Phe Leu Thr Tyr Arg Pro Ser Cys Ile
225                 230                 235                 240

Ala Ala Ala Ala Ile Leu Ser Ala Ala Asn Glu Ile Pro Asn Trp Ser
                245                 250                 255

Phe Val Asn Pro Glu His Ala Glu Ser Trp Cys Glu Gly Leu Ser Lys
            260                 265                 270

Glu Lys Ile Ile Gly Cys Tyr Glu Leu Ile Gln Glu Ile Val Ser Ser
        275                 280                 285

Asn Asn Arg Arg Asn Ala Pro Lys Val Leu Pro Gln Leu Arg Val Thr
    290                 295                 300

Ala Arg Thr Thr Arg Trp Ser Thr Val Ser Ser Leu Ser Ser Ser Pro
305                 310                 315                 320

Ser Ser Ser Ser Ser Pro Ser Tyr Ser Leu Ser Tyr Lys Lys Arg Lys
                325                 330                 335

Leu Asn Ser Cys Phe Trp Val Asp Val Asp Lys Gly Asn Ser Glu Gly
            340                 345                 350

Arg Glu Lys Lys Gln Thr Arg
        355

<210> SEQ ID NO 42
<211> LENGTH: 356
<212> TYPE: PRT
<213> ORGANISM: Oryza sativa

<400> SEQUENCE: 42

Met Ala Ala Leu Thr Ser Tyr Glu Met Ala Ala Ser Ile Leu Leu Cys
1               5                   10                  15

Ala Glu Asp Ser Ser Val Leu Gly Phe Gly Gly Glu Glu Glu
            20                  25                  30

Glu Glu Glu Asp Val Val Ala Gly Lys Arg Ala Arg Cys Ala Gly Pro
        35                  40                  45

Pro Pro Pro Cys Val Asp Val Ala Gly Val Asp Phe Ala Val Pro
    50                  55                  60

Ser Glu Glu Cys Val Ala Arg Leu Val Glu Thr Glu Ala Asp His Met
65                  70                  75                  80

Pro Arg Glu Asp Tyr Ala Glu Arg Leu Arg Ala Gly Gly Asp Gly
            85                  90                  95

Asp Leu Asp Leu Arg Val Arg Met Asp Ala Ile Asp Trp Ile Trp Lys
            100                 105                 110

Val His Ser Tyr Tyr Ser Phe Ala Pro Leu Thr Ala Cys Leu Ala Val
        115                 120                 125

Asn Tyr Leu Asp Arg Phe Leu Ser Leu Tyr Gln Leu Pro Asp Gly Lys
    130                 135                 140

Asp Trp Met Thr Gln Leu Leu Ala Val Ala Cys Leu Ser Leu Ala Ala
145                 150                 155                 160

Lys Met Glu Glu Thr Asp Val Pro Gln Ser Leu Asp Leu Gln Val Gly
                165                 170                 175

Glu Glu Arg Tyr Val Phe Glu Ala Lys Thr Ile Gln Arg Met Glu Leu
            180                 185                 190

Leu Val Leu Ser Thr Leu Lys Trp Arg Met Gln Ala Val Thr Pro Phe
        195                 200                 205

Ser Tyr Val Asp Tyr Phe Leu Arg Glu Leu Asn Gly Gly Asp Pro Pro

```
                  210                 215                 220
Ser Gly Arg Ser Ala Leu Leu Ser Glu Leu Ile Leu Cys Ile Ala
225                 230                 235                 240

Arg Gly Thr Glu Cys Leu Gly Phe Arg Pro Ser Glu Ile Ala Ala Ala
                    245                 250                 255

Val Ala Ala Val Val Gly Glu Glu His Ala Ala Phe Ser His Val
                260                 265                 270

Asn Lys Glu Arg Met Ser His Cys Gln Glu Val Ile Gln Ala Met Glu
                275                 280                 285

Leu Ile His Pro Lys Pro Ala Ser Pro Ser Arg Val Phe Val Ser Ser
                290                 295                 300

Ser Ile Pro Arg Ser Pro Thr Gly Val Leu Asp Ala Ala Gly Cys Leu
305                 310                 315                 320

Ser Tyr Arg Ser Asp Asp Ser Ala Val Ala Ser His Tyr Ala Ala Ser
                325                 330                 335

Ser Trp Gly Tyr Glu His Asp Ser Pro Val Ser Ser Lys Arg Arg
                340                 345                 350

Lys Ile Ser Arg
        355

<210> SEQ ID NO 43
<211> LENGTH: 383
<212> TYPE: PRT
<213> ORGANISM: Oryza sativa

<400> SEQUENCE: 43

Met Ala Pro Ser Ser Ser Ser Cys His Asp Ala Ala Ala Ser Met Leu
1               5                   10                  15

Leu Cys Ala Glu Asp Asn Ser Ser Ile Leu Trp Leu Glu Asp Glu Glu
                20                  25                  30

Gly Glu Val Gly Glu Arg Arg Ser Gly Gly Cys Arg Ser Met Val Gly
                35                  40                  45

Asp Leu Ala Ala Gly Gly Gly Gly Ser Gly Gly Gly Val Glu
        50                  55                  60

Glu Glu Glu Asp Met Phe Pro Arg Gln Ser Glu Glu Cys Val Ala Ser
65                  70                  75                  80

Leu Val Glu Arg Glu Gln Ala His Met Pro Arg Ala Asp Tyr Gly Glu
                85                  90                  95

Arg Leu Arg Gly Gly Gly Gly Asp Val Asp Leu Arg Val Arg Ser Glu
                100                 105                 110

Ala Ile Gly Trp Ile Trp Glu Val Tyr Thr Tyr Tyr Asn Phe Ser Ser
                115                 120                 125

Val Thr Ala Tyr Leu Ala Val Asn Tyr Leu Asp Arg Phe Leu Ser Gln
                130                 135                 140

Tyr Glu Leu Pro Glu Gly Arg Asp Trp Met Thr Gln Leu Leu Ser Val
145                 150                 155                 160

Ala Cys Leu Ser Ile Ala Ala Lys Met Glu Glu Thr Val Val Pro Gln
                165                 170                 175

Cys Leu Asp Leu Gln Ile Gly Glu Pro Arg Phe Leu Phe Glu Val Glu
                180                 185                 190

Thr Ile His Arg Met Glu Leu Leu Val Leu Thr Asn Leu Asn Trp Arg
                195                 200                 205

Met Gln Ala Val Thr Pro Phe Ser Tyr Ile Asp Tyr Phe Leu Arg Glu
    210                 215                 220
```

-continued

```
Leu Asn Ser Gly Asn Ala Ala Pro Arg Ser Trp Leu Leu Arg Ser Ser
225                 230                 235                 240

Glu Leu Ile Leu Arg Ile Ala Ala Gly Thr Gly Phe Leu Glu Phe Arg
            245                 250                 255

Pro Ser Glu Ile Ala Ala Val Ala Ala Thr Val Ala Gly Glu Ala
        260                 265                 270

Thr Gly Val Val Glu Glu Asp Ile Ala Glu Ala Phe Thr His Val Asp
    275                 280                 285

Lys Gly Arg Val Leu Gln Cys Gln Glu Ala Ile Gln Asp His His Tyr
290                 295                 300

Ser Met Ala Thr Ile Asn Thr Val Gln Pro Lys Pro Ala Ser Thr Arg
305                 310                 315                 320

Arg Gly Ser Ala Ser Ala Ser Ser Ser Val Pro Glu Ser Pro Val
            325                 330                 335

Ala Val Leu Asp Ala Gly Cys Leu Ser Tyr Lys Ser Asp Asp Thr Asp
            340                 345                 350

Ala Ala Thr Ile Ala Ser His Gly Gly Arg Arg Lys Ser Cys Phe
        355                 360                 365

Asp Ser Ser Pro Val Thr Ser Lys Lys Arg Arg Lys Leu Ser Arg
    370                 375                 380

<210> SEQ ID NO 44
<211> LENGTH: 356
<212> TYPE: PRT
<213> ORGANISM: Oryza sativa

<400> SEQUENCE: 44

Met Gly Val Leu Cys Phe Gly Ala Ser Asn Ile Leu Leu Cys Ala Glu
1               5                   10                  15

Asp Ser Ser Val Leu Gly Leu Gly Gly Phe Gly Gly Gly Gly Gly
            20                  25                  30

Glu Val Ala Ala Glu Leu Gly Cys Gly Gly Gly Gly Phe Asp Phe
        35                  40                  45

Phe Gly Phe Gly Gly Ala Val Phe Pro Ile Asp Ser Asp Glu Phe
    50                  55                  60

Val Ala Leu Leu Val Glu Lys Glu Met Asp His Gln Pro Gln Arg Gly
65                  70                  75                  80

Tyr Leu Glu Lys Leu Glu Leu Gly Gly Leu Glu Cys Ser Trp Arg Lys
            85                  90                  95

Asp Ala Ile Asp Trp Ile Cys Lys Val His Ser Tyr Tyr Asn Phe Gly
            100                 105                 110

Pro Leu Ser Leu Tyr Leu Ala Val Asn Tyr Leu Asp Arg Phe Leu Ser
        115                 120                 125

Ser Phe Asn Leu Pro His Asp Glu Ser Trp Met Gln Gln Leu Leu Ser
130                 135                 140

Val Ser Cys Leu Ser Leu Ala Thr Lys Met Glu Glu Thr Val Val Pro
145                 150                 155                 160

Leu Pro Met Asp Leu Gln Val Phe Asp Ala Glu Tyr Val Phe Glu Ala
            165                 170                 175

Arg His Ile Lys Arg Met Glu Leu Ile Val Met Lys Thr Leu Lys Trp
        180                 185                 190

Arg Leu Gln Ala Val Thr Pro Phe Ser Phe Ile Gly Tyr Phe Leu Asp
    195                 200                 205

Lys Phe Asn Glu Gly Lys Pro Pro Ser Tyr Thr Leu Ala Ser Trp Cys
210                 215                 220
```

```
Ser Asp Leu Thr Val Gly Thr Leu Lys Asp Ser Arg Phe Leu Ser Phe
225                 230                 235                 240

Arg Pro Ser Glu Ile Ala Ala Val Val Leu Ala Val Leu Ala Glu
            245                 250                 255

Asn Gln Phe Leu Val Phe Asn Ser Ala Leu Gly Glu Ser Glu Ile Pro
            260                 265                 270

Val Asn Lys Glu Met Val Met Arg Cys Tyr Glu Leu Met Val Glu Lys
                275                 280                 285

Ala Leu Val Lys Lys Ile Arg Asn Ser Asn Ala Ser Ser Ser Val Pro
            290                 295                 300

His Ser Pro Ile Thr Val Leu Asp Ala Ala Cys Phe Ser Phe Arg Ser
305                 310                 315                 320

Asp Asp Thr Thr Leu Gly Ser Ser Gln Ser Asn Ser Asn Asn Lys Asp
                325                 330                 335

Tyr Asn Ser Gln Asp Ser Ala Pro Ala Ser Lys Arg Arg Arg Leu Asn
            340                 345                 350

Thr Thr Pro Ile
            355

<210> SEQ ID NO 45
<211> LENGTH: 342
<212> TYPE: PRT
<213> ORGANISM: Oryza sativa

<400> SEQUENCE: 45

Met Ala Pro Ser Phe Asp Phe Ala Ala Ser Ile Leu Leu Cys Ala Glu
1               5                   10                  15

Asp Asn Thr Ala Ile Leu Asp Leu Gly Glu Glu Ser Glu Glu Ile Ser
                20                  25                  30

Trp Val Val Gly Val Asp Ala Ser Leu Gly Asp Leu Ser Met Asp Phe
            35                  40                  45

Pro Leu Gln Ser Asp Asp Cys Ile Glu Ala Leu Leu Gly Arg Glu Glu
    50                  55                  60

Gln Gln His Ile Pro Met Glu Gly Tyr Leu Gln Arg Leu Leu Leu Gln
65                  70                  75                  80

Pro Asp Gly Leu Asp Leu Val Ala Val Arg Ser Asp Ala Ile Asp Trp
                85                  90                  95

Ile Trp Lys Val His Glu Leu Tyr Lys Phe Gly Pro Leu Thr Ala Val
            100                 105                 110

Leu Ser Val Asn Tyr Leu Asp Arg Phe Leu Ser Val Phe Asp Leu Pro
        115                 120                 125

Gln Glu Glu Ala Cys Met Thr Gln Leu Leu Ala Val Ala Ser Leu Ser
    130                 135                 140

Leu Ala Ala Lys Met Glu Glu Thr Val Val Pro His Pro Leu Asp Leu
145                 150                 155                 160

Gln Val Cys Asp Ala Lys Tyr Val Phe Glu Thr Arg Thr Ile Lys Arg
                165                 170                 175

Met Glu Leu Ala Val Leu Asn Ala Leu Lys Trp Arg Met Gln Ala Val
            180                 185                 190

Thr Ala Cys Ser Phe Ile Asp Tyr Tyr Leu His Lys Phe Asn Asp Asp
        195                 200                 205

Asp Thr Pro Ser Thr Ser Ala Leu Ser Arg Ser Val Asp Leu Ile Leu
    210                 215                 220

Ser Thr Cys Lys Val Ala Glu Phe Leu Val Phe Arg Pro Ser Glu Ile
```

```
                   225                 230                 235                 240
Ala Ala Ser Val Ala Leu Val Ala Leu Glu Glu His Glu Thr Ser Met
                245                 250                 255

Phe Glu Arg Val Ala Thr Cys Tyr Lys Asn Leu Lys Lys Glu Arg Val
            260                 265                 270

Leu Arg Cys Tyr Glu Met Ile Gln Asp Lys Ile Ile Met Arg Asn Ile
        275                 280                 285

Met Arg Gln Ser Ala Gly Ser Val Phe Ser Ile Pro Lys Ser Pro Ile
    290                 295                 300

Gly Val Leu Asp Ala Ala Ala Cys Ile Ser Gln Gln Ser Glu Asp Thr
305                 310                 315                 320

Phe Val Gly Ser Pro Ala Thr Asn Tyr Glu Ser Ser Ala Ser Ser Lys
                325                 330                 335

Arg Arg Arg Ile Cys Arg
                340

<210> SEQ ID NO 46
<211> LENGTH: 322
<212> TYPE: PRT
<213> ORGANISM: Oryza sativa

<400> SEQUENCE: 46

Met Gly Ala Pro Ala Thr Ala Ala Ser Gly Gly Gly Asp Asp Asp
1               5                   10                  15

Arg Asp Val Val Phe Glu Tyr Leu Leu Cys Thr Glu Glu Asp Ala Ala
            20                  25                  30

Ser Ala Gly Ser Phe Phe Gln Gln Leu Gln Gly Pro Ala Pro Ala Val
        35                  40                  45

Ser Ser Ser Pro Ser Thr Thr Thr Ala Thr Ala Pro Ala Ala Ala Gly
    50                  55                  60

Ser Cys Asp Asp Gly Gly Glu Glu Glu Glu Glu Val Trp Thr Val
65                  70                  75                  80

Asp Val Val Ala Glu Leu Ile Gly Gly Glu Ala Glu Arg Ser His Ser
                85                  90                  95

Pro Arg Ala Asp Tyr Pro Gly Arg Leu Arg Ser Gly Arg Pro Ala Asp
            100                 105                 110

Leu Ala Ala Arg Ala Asp Ser Val Ala Trp Ile Leu Lys Val Arg Glu
        115                 120                 125

Leu Tyr Gly Met Leu Pro Val Thr Ala Tyr Leu Ala Val Ser Tyr Met
    130                 135                 140

Asp Arg Phe Leu Ser Leu His Arg Leu Pro Met Glu Asp Ala Arg Tyr
145                 150                 155                 160

Ile Phe Glu His Arg Thr Ile Phe Arg Met Glu Leu Leu Val Leu Asp
                165                 170                 175

Ala Leu Asp Trp Arg Leu Arg Ser Ile Thr Pro Phe Thr Phe Met Tyr
            180                 185                 190

Leu Phe Ala Asp Lys Val Asp Pro Asn Gly Lys His Ile Arg Glu Leu
        195                 200                 205

Ile His Gln Ala Thr Gln Val Thr Leu Ala Thr Ile His Asp Thr Glu
    210                 215                 220

Phe Leu Asp His Cys Pro Ser Ile Ala Ala Ala Val Leu Cys
225                 230                 235                 240

Ala Ser Ser Glu Ile Met Gln Leu Val Ser Ile Asp His Gly Thr Leu
                245                 250                 255
```

```
Val Ser Trp Arg Ile Ile Gly Leu Asp Glu Glu Ala Ile Ile Arg Cys
            260                 265                 270

Tyr Arg Leu Met Gln Gln Leu Ile Ser Ser Asn Asn Val Gly Arg Glu
            275                 280                 285

Ser Thr Glu Ile Thr Met Ala Thr Thr Thr Thr Ala Thr Thr Ala
            290                 295                 300

Val Ser Ser Glu Glu Val Val Ser Ser Pro Pro Ser Lys Arg Arg
305                 310                 315                 320

Lys Met

<210> SEQ ID NO 47
<211> LENGTH: 365
<212> TYPE: PRT
<213> ORGANISM: Oryza sativa

<400> SEQUENCE: 47

Met Ser Met Glu Glu Ala Glu Glu Cys Ser Ala Ala Cys Gly Phe Ser
1               5                   10                  15

Leu Thr Cys Gln Glu Asp Gly Ala Asp Leu Gly Asp Gly Val Val Asp
            20                  25                  30

Asp Asp Asp Asp Gly Asp Val Phe Leu Phe Tyr Asn Ala Val Ala Ala
        35                  40                  45

Ala Asp Glu Glu Glu Glu Glu Glu Tyr Val Glu Gln Met Val Ser
    50                  55                  60

Lys Glu Ala Ser Phe Cys Cys Ser Ser Ser Ser Leu Phe Asp Ala
65                  70                  75                  80

Ala Ala Gly Asp Gly Tyr Gly Asp Gly Asp Gly Asp Gly Asp Trp Phe
                85                  90                  95

Arg Gln Ala Arg Leu Ala Ala Ile Lys Trp Ile Leu Glu Thr Arg Gly
            100                 105                 110

Tyr Phe Gly Phe Gly His Arg Thr Ala Tyr Leu Ala Ile Ala Tyr Phe
        115                 120                 125

Asp Arg Phe Cys Leu Arg Arg Val Asp Arg Glu Ala Met Pro Trp
    130                 135                 140

Ala Ala Arg Leu Leu Ser Ile Ala Cys Val Ser Val Ala Ala Lys Met
145                 150                 155                 160

Glu Glu Tyr Gln Ser Pro Ala Leu Ser Glu Phe Asp Ala Gly Gly Gly
                165                 170                 175

Arg Val Phe Cys Ser Asp Ser Ile Arg Arg Met Glu Leu Leu Val Leu
            180                 185                 190

Ser Thr Leu Gly Trp Arg Met Gly Ala Val Thr Pro Phe Asp Phe Leu
        195                 200                 205

Pro Cys Phe Ser Ser Arg Leu His Arg His His Gly Gly Ala Gly
    210                 215                 220

Ala Ala Gly His Gly Ala Ala Ala Ala Arg Val Ala Leu Asn Ala
225                 230                 235                 240

Val Gly Phe Thr Phe Ala Thr Ala Glu Ala Gly Ser Val Leu Asp Tyr
                245                 250                 255

Arg Pro Ser Thr Val Ala Ala Ala Ile Leu Ala Ala Ser Tyr Gly
            260                 265                 270

Ala Pro Leu Thr Lys Glu Ala Leu Glu Ser Lys Met Ser Asn Leu Ser
        275                 280                 285

Pro Ser Cys Leu Ile Asp Lys Glu Asn Val His Ala Cys Tyr Ser Met
    290                 295                 300
```

Met Val Gly Asp Met Asn Asn Arg Arg Ser Ser Lys Arg Pro Leu
305                 310                 315                 320

Gln Cys Ser Asp Ser Asn Glu Ile Thr Thr Thr Ser Thr Tyr Asp Ser
            325                 330                 335

Val Leu Val Asp Asp Val Thr Asp Thr Ala Ala Phe Ala Ala Thr Ala
            340                 345                 350

Met Asn Lys Arg Leu Arg Pro Glu Pro Pro Arg Ile Arg
        355                 360                 365

<210> SEQ ID NO 48
<211> LENGTH: 367
<212> TYPE: PRT
<213> ORGANISM: Oryza sativa

<400> SEQUENCE: 48

Met Glu Ala Glu Asp Glu Tyr Ser Ala Gly Cys Ser Phe Ser Leu Met
1               5                   10                  15

Cys Gln Glu Asp Ser Thr Asp Leu Asp Asp Asp Gly Gly Gly Gly Gly
            20                  25                  30

Cys Phe Ala Gly Asp Gly Arg Ala Asp Leu Leu Leu Val Tyr Asn Ala
        35                  40                  45

Ala Ala Ala Ala Asp Asp Glu Asp Glu Glu Glu Val Glu Glu Tyr Met
    50                  55                  60

Asp His Leu Val Ser Lys Glu Ser Ser Phe Cys Ser Ser Ser Ser Ser
65                  70                  75                  80

Thr Ser Ser Ser Ser Cys Cys Phe Ser Asp Ala Gly Gly Glu Ser Ala
                85                  90                  95

Ala Ala Ala Ala Pro Met Asp Trp Phe Ala Leu Ala Arg Arg Ala Thr
            100                 105                 110

Val Lys Trp Ile Leu Glu Thr Arg Gly Cys Phe Gly Phe Cys His Arg
        115                 120                 125

Thr Ala Tyr Leu Ala Ile Ala Tyr Phe Asp Arg Phe Cys Leu Arg Arg
    130                 135                 140

Cys Ile Asp Arg Ser Val Met Pro Trp Ala Ala Arg Leu Leu Ala Val
145                 150                 155                 160

Ala Cys Val Ser Leu Ala Ala Lys Met Glu Glu Tyr Arg Ala Pro Ala
                165                 170                 175

Leu Ser Glu Phe Arg Ala Gly Val Gly Asp Asp Gly Tyr Glu Phe Ser
            180                 185                 190

Cys Val Cys Ile Arg Arg Met Glu Leu Leu Val Leu Ser Thr Leu Asp
        195                 200                 205

Trp Arg Met Ala Ala Val Thr Pro Phe Asp Tyr Leu Pro Cys Leu Ser
    210                 215                 220

Ser Arg Leu Arg Arg His Val Gly Gly Gly Gly Ala Gly Ala Ser
225                 230                 235                 240

Ala Ala Leu Ile Phe Ser Ala Ala Glu Ala Ala Ser Val Leu Asp His
                245                 250                 255

Arg Pro Ser Thr Val Ala Ala Ala Val Leu Ala Ala Thr His Gly
            260                 265                 270

Ala Leu Thr Arg Glu Ala Leu Glu Ser Lys Met Ser Gly Leu Ser Pro
        275                 280                 285

Ser Phe Leu Leu Asp Lys Glu Asp Val Phe Ala Cys Tyr Ser Ala Met
    290                 295                 300

Leu Ser Gln Pro Thr Ser Pro Ala Ser Lys Ser Thr Thr Thr Thr Thr
305                 310                 315                 320

```
Gly Lys Arg Ser Ser Ser Ser Cys Ser Glu Ser Thr Asp Ala Ala
            325                 330                 335

Ser Ser Tyr Asp Ala Thr Ala Ala Ser Phe Pro Ala Ala Ser Cys
            340                 345                 350

Gly Ser Lys Arg Met Arg Leu Glu Leu Pro Gly Gly Ile Leu Arg
            355                 360                 365

<210> SEQ ID NO 49
<211> LENGTH: 320
<212> TYPE: PRT
<213> ORGANISM: Oryza sativa

<400> SEQUENCE: 49

Met Asp Met Ala Thr Gly Ala Lys Glu Val Val Val Glu Ala Tyr
1               5                   10                  15

Glu Tyr Glu Phe Asp Leu Glu Asn Pro Phe Thr Ser Pro Ala Asp Glu
                20                  25                  30

Pro Ile Ala Ser Leu Leu Asp Ala Glu Gly His His Ser Pro Ser Val
                35                  40                  45

Ser Ala Ala Ala Ser Ala Ala Arg Arg Glu Ala Ala Gly Phe Ile Ser
            50                  55                  60

Lys Val Arg Tyr Asp Gly Glu Leu Asp Val His Pro Arg Val Ala Tyr
65                  70                  75                  80

Leu Ala Leu Asn Tyr Val Asp Arg Tyr Leu Ser Lys Arg Gln Leu Ala
                85                  90                  95

Cys Glu Arg Asn Pro Trp Ala Pro Arg Leu Leu Ala Ile Ser Cys Leu
            100                 105                 110

Thr Leu Ala Ala Lys Met Gln Arg Ala Ala Ala Ile Ser Ala Ala Asp
            115                 120                 125

Ile Gln Arg Gly Glu Glu Phe Met Phe Asp Glu Ala Lys Ile Gln Arg
            130                 135                 140

Met Glu Gln Met Val Leu Asn Ala Leu Glu Trp Arg Thr Arg Ser Val
145                 150                 155                 160

Thr Pro Leu Ala Phe Leu Gly Phe Phe Leu Ser Ala Cys Phe Pro Gln
                165                 170                 175

Pro Arg His Pro Ala Leu Leu Asp Ala Ile Lys Ala Arg Ala Val Asp
                180                 185                 190

Leu Leu Leu Arg Val Gln Pro Glu Val Lys Met Ala Glu Phe Ser Pro
            195                 200                 205

Ser Val Ala Ala Ala Ala Leu Leu Ala Ala Gly Glu Val Ala
            210                 215                 220

Gly Ala His Leu Leu Gly Phe Glu Ala Gly Val Ala Ala Cys Pro Phe
225                 230                 235                 240

Val Asn Ser Glu Lys Leu Arg Glu Cys Gly Glu Val Met Ala Ala Ala
                245                 250                 255

Cys Gly Val Gly Pro Ser Trp Ala Ala Ala Thr Ser Ala Glu Thr
            260                 265                 270

Pro Val Thr Val Leu Gly His His Arg Ser Ala Ser Ser Glu Ser Glu
            275                 280                 285

Arg Thr Thr Thr Val Gly Ser Ala Ala Asn Ser Ala Asp Ala Lys Arg
            290                 295                 300

Arg Cys Met Gly Pro Pro Arg Gln Trp Gly Val Gly Gly Pro Asp Glu
305                 310                 315                 320
```

<210> SEQ ID NO 50
<211> LENGTH: 359
<212> TYPE: PRT
<213> ORGANISM: Saccharum officinarum
<220> FEATURE:
<221> NAME/KEY: misc_feature
<222> LOCATION: (188)..(189)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid

<400> SEQUENCE: 50

Met Thr Pro Arg Phe Asp Phe Ala Ala Ser Val Leu Leu Cys Ser Glu
1               5                   10                  15

Asp Ser Thr Thr Ile Phe Asp Leu Glu Glu Glu Arg Glu Gly Ile
            20                  25                  30

Leu Cys Val Leu Arg Pro Ser Ser Arg His Ala Ser Ala Pro Ser Gly
        35                  40                  45

Ala Leu Ser Ile Asp Phe Pro Leu Gln Ser Asp Ser Cys Ile Glu Ala
    50                  55                  60

Phe Leu Gly Arg Glu Glu Asp His Leu Pro Met Glu Gly Tyr Ala Glu
65                  70                  75                  80

Arg Leu Leu Leu Gln Gln Pro Gly Gly Ser Asp Leu Val Ala Ile Arg
                85                  90                  95

Asn Tyr Ala Ile Asp Trp Ile Trp Lys Val His Asp Tyr Tyr Lys Leu
            100                 105                 110

Gly Pro Leu Thr Val Val Leu Ser Val Asn Tyr Met Asp Arg Phe Leu
        115                 120                 125

Ser Val Tyr His Asn Ala Leu Glu Lys Asp Trp Met Thr Gln Leu Leu
    130                 135                 140

Thr Val Ala Cys Leu Ser Leu Ala Val Lys Met Glu Glu Thr Ile Val
145                 150                 155                 160

Phe Asn Pro Leu Asn Leu Gln Val Val Asp Ala Glu Tyr Val Phe Glu
                165                 170                 175

Pro Ser Thr Ile His Arg Met Glu Val Leu Val Xaa Xaa Lys His Arg
            180                 185                 190

Met Glu Val Leu Val Leu His Thr Xaa Ser Trp Arg Met Gln Ala Val
        195                 200                 205

Thr Pro Cys Ser Phe Ile Asp Tyr Tyr Leu His Gln Phe Ser Asp Gly
    210                 215                 220

Asp Val Val Ser Glu Ile Ile Leu Ser Arg Thr Val Glu Leu Ile Leu
225                 230                 235                 240

Xaa Ala His Leu Lys Leu Leu Ser Phe Trp Phe Ser Lys Pro Ser Glu
                245                 250                 255

Ile Ala Ala Ser Ile Ala Leu Val Ala Leu Gly Lys Arg Asp Ser Ser
            260                 265                 270

Val Leu Glu Ser Val Ala Thr Cys Arg Lys Glu Leu Arg Lys Glu Arg
        275                 280                 285

Val Leu Gly Cys Tyr Glu Met Val Gln Asp Lys Ile Val Thr Gly Asp
    290                 295                 300

Ile Val Ile Lys Ser Asp Gly Ser Ser Val Phe Pro Lys Gln His Ser
305                 310                 315                 320

```
                                    -continued

Pro Thr Gly Val Leu Ala Val Val Ala Cys Glu Ser Gln Gln Ser Glu
                325                 330                 335

Asp Thr Ser Ala Gly Ala Thr Val Cys Asn Glu Ser Ser Ser Ala Arg
            340                 345                 350

Lys Arg Arg Arg Ile Cys Arg
        355

<210> SEQ ID NO 51
<211> LENGTH: 5
<212> TYPE: PRT
<213> ORGANISM: Artificial Sequence
<220> FEATURE:
<223> OTHER INFORMATION: Consensus sequence motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 51

Leu Xaa Cys Xaa Glu
1               5

<210> SEQ ID NO 52
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Xaa can be Lys, Met, Thr, or Arg

<400> SEQUENCE: 52

Xaa Pro Trp Met
1
```